United States Patent
Szczepanski et al.

(10) Patent No.: US 6,211,381 B1
(45) Date of Patent: Apr. 3, 2001

(54) THIAZOLE COMPOUNDS

(75) Inventors: Henry Szczepanski, Wallbach (CH); Thomas Göbel; Ottmar Franz Hüter, both of Lörrach (DE); Anthony Cornelius O'Sullivan, Basel (CH); Marcel Senn, Blonay (CH); Thomas Rapold, Wallbach (CH); Peter Maienfisch, Rodersdorf (CH); Thomas Pitterna, Basel (CH)

(73) Assignee: Novartis Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/077,569

(22) PCT Filed: Dec. 2, 1996

(86) PCT No.: PCT/IB96/01329

§ 371 Date: Jun. 1, 1998

§ 102(e) Date: Jun. 1, 1998

(87) PCT Pub. No.: WO97/20829

PCT Pub. Date: Jun. 12, 1997

(30) Foreign Application Priority Data

Dec. 1, 1995 (CH) .................................................. 3412/95

(51) Int. Cl.$^7$ ................................................ C07D 277/32
(52) U.S. Cl. .......................................... 548/182; 548/202
(58) Field of Search ............................................... 548/182

(56) References Cited

U.S. PATENT DOCUMENTS 5,185,354 * 2/1993 Natsume .............................. 514/369

* cited by examiner

Primary Examiner—Robert Gerstl
(74) Attorney, Agent, or Firm—John Peabody; William A. Teoli, Jr.

(57) ABSTRACT

The invention relates to a process for preparing a compound of formula (I), in which X is CH or N, Y is $NO_2$ or CN, Z is $CHR_3$, O, $NR_3$ or S, $R_1$ and $R_2$ are either each, independently of the other, hydrogen or unsubstituted or $R_4$-substituted alkyl or together a two- or three-membered alkylene bridge or a two- or three-membered alkylene bridge in which one member is replaced by a hetero member selected from the group, consisting of $NR_5$, O and S, $R_3$ is H or unsubstituted or $R_4$-substituted alkyl, $R_4$ is an unsubstituted or substituted aryl or heteroaryl group, and $R_5$ is H or alkyl, which comprises a) reacting a compound of formula (II) with a chlorinating agent or b1) initially reacting a compound of formula (IV) with a compound of formula (V) and b2) further reacting the compound of formula (II) obtainable thereby, with or without intermediate isolation, with a chlorinating agent, to intermediates used in this process, to the use of these intermediates and to a process for the preparation of these intermediates.

1 Claim, No Drawings

THIAZOLE COMPOUNDS

The invention relates to a process for preparing a compound of the formula

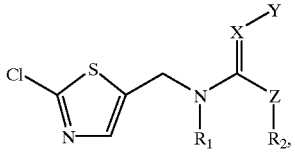

(I)

in which
X is CH or N,
Y is $NO_2$ or CN,
Z is $CHR_3$, O, $NR_3$ or S,
$R_1$ and $R_2$ are either each, independently of the other, hydrogen or unsubstituted or $R_4$-substituted alkyl or together a two- or three-membered alkylene bridge or a two- or three-membered alkylene bridge in which one member is replaced by a hetero member selected from the group, consisting of $NR_5$, O and S,
$R_3$ is H or unsubstituted or $R_4$-substituted alkyl,
$R_4$ is an unsubstituted or substituted aryl or heteroaryl group, and
$R_5$ is H or alkyl,
which comprises
a) reacting a compound of the formula

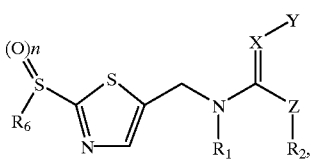

(II)

in which X, Y, Z, $R_1$ and $R_2$ are as defined for the formula I,
n is 0, 1 or 2,
$R_6$ is unsubstituted or $R_8$-substituted alkyl, unsubstituted or $R_8$-substituted alkenyl, unsubstituted or $R_8$-substituted alkynyl, cycloalkyl, unsubstituted or substituted aryl, heteroaryl, $SR_7$, (alkylene)SH or (alkylene)$SR_7$,
$R_7$ is unsubstituted or $R_4$-substituted alkyl, unsubstituted or $R_4$-substituted alkenyl, unsubstituted or $R_4$-substituted alkynyl, cycloalkyl, unsubstituted or substituted aryl, heteroaryl or a group of the formula

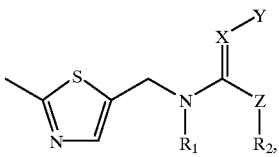

(III)

in which X, Y, Z, $R_1$ and $R_2$ are as defined for the formula II, and
$R_8$ is an unsubstituted or substituted aryl or heteroaryl group, —COOH, COOM, wherein M is an alkali metal, or —COO-$C_1$-$C_8$-alkyl,
with a chlorinating agent, or b1) initially reacting a compound of the formula

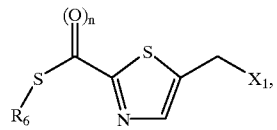

(IV)

in the free form or the form of a salt,
in which $R_6$ and n are as defined for the formula II and $X_1$ is a leaving group, in the presence or absence of a base, with a compound of the formula

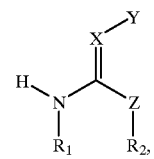

(V)

which is known or which can be prepared by methods known per se and in which $R_1$, $R_2$, X, Y and Z are as defined for the formula I, and b2) further reacting the compound of the formula II obtainable thereby, with or without intermediate isolation, with a chlorinating agent,
to intermediates used in this process, to the use of these intermediates and to a process for the preparation of these intermediates.

The existing processes for preparing the compounds of the formula I require as starting material inter alia 2-chloro-5-chloromethylthiazole. The latter, however, is harmful on direct contact, and there is therefore a need to replace this compound by harmless compounds. This object is achieved by the preparative process according to the invention.

The general terms used hereinbefore and hereinafter have, unless defined otherwise, the meanings listed below:

Carbon-containing groups and compounds each contain, unless defined otherwise, 1 up to and including 8, preferably 1 up to and including 6, in particular 1 up to and including 4, especially 1 or 2 carbon atoms.

Halogen is preferably chlorine or bromine.

Alkyl—as a group per se and also as a structural element of other groups and compounds, for example alkoxy and alkylthio—is, in each case with due regard to the number of carbon atoms contained in the respective group or compound, either straight-chain, i.e. methyl, ethyl, propyl, butyl, pentyl or hexyl, or branched, for example isopropyl, isobutyl, sec-butyl, tert-butyl, isopentyl, neopentyl or isohexyl.

Alkenyl and alkynyl are straight-chain or branched and each contain two or preferably one unsaturated carbon-carbon bond(s). The double or triple bonds of these substituents are separated from the remainder of the compound II preferably by at least one saturated carbon atom. Examples include allyl, methallyl, but-2-enyl, but-3-enyl, propargyl, but-2-ynyl and but-3-ynyl.

Cycloalkyl is cyclopropyl, cyclobutyl, cyclopentyl or cyclohexyl, preferably cyclopropyl.

Alkylene—as a group per se and also as a structural element of other groups and compounds, such as (alkylene)$SR_7$- is, in each case with due regard to the number of carbon atoms contained in the respective group or compound, either straight-chain, for example —CH$_2$CH$_2$—, —CH$_2$CH$_2$CH$_2$— or —CH$_2$CH$_2$CH$_2$CH$_2$—, or branched, for example —CH(CH$_3$)—, —CH(C$_2$H$_5$)—, —C(CH$_3$)$_2$—, —CH(CH$_3$)CH$_2$— or —CH(CH$_3$)CH(CH$_3$)—, and it can also be methylene.

Aryl is phenyl or naphthyl, in particular phenyl.

Heteroaryl is a 5- to 7-membered aromatic ring with one to up to three hetero atoms selected from the group consisting of N, O and S. Preference is given to aromatic 5- and 6-membered rings which have a nitrogen atom as hetero atom and which can, if desired, also contain a further hetero atom, preferably nitrogen or sulfur, in particular nitrogen.

Substituted aryl and heteroaryl are preferably substituted with one to three substituents selected from the group consisting of halogen, NO$_2$, CN, C$_1$–C$_4$alkyl, C$_1$–C$_4$alkoxy, halogenC$_1$–C$_4$alkyl and halogenC$_1$–C$_4$alkoxy. Preferred are unsubstituted or monosubstituted, especially unsubstituted aryl and heteroaryl.

Preferred starting materials for preparing the corresponding compounds of the formula I according to the invention are:

(1) a compound of the formula II where
   X is N;

(2) a compound of the formula II where
   Y is NO$_2$;

(3) a compound of the formula II where
   Z is CHR$_3$ or NR$_3$, preferably NR$_3$;

(4) a compound of the formula II where
   R$_1$ and R$_2$ are together a two- or three-membered alkylene bridge with or without a hetero member selected from the group consisting of NR$_5$, O and S;

(5) a compound of the formula II where
   R$_3$ is unsubstituted or R$_4$-substituted C$_1$–C$_4$alkyl,
preferably unsubstituted C$_1$–C$_2$alkyl;

(6) a compound of the formula II where
   R$_4$ is unsubstituted or substituted aryl or heteroaryl, the substituents being selected from the group consisting of halogen, NO$_2$, CN, C$_1$–C$_4$alkyl, C$_3$–C$_6$cycloalkyl, C$_1$–C$_4$alkoxy and C$_1$–C$_4$alkylthio,
preferably unsubstituted aryl;

(7) a compound of the formula II wherein
   R$_6$ is unsubstituted or R$_8$-substituted C$_1$–C$_4$alkyl, aryl, heteroaryl, SR$_7$, (alkylen)SH or (alkylene)SR$_7$, preferably aryl, R$_8$-substituted C$_1$–C$_4$alkyl or SR$_7$,
   in particular R$_8$-substituted C$_1$–C$_2$alkyl or especially aryl;

(8) a compound of the formula II wherein
   R$_7$ is unsubstituted or R$_4$-substituted alkyl, aryl, heteroaryl or a group of the formula

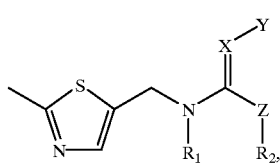

(III)

in which X, Y, Z, R$_1$ and R$_2$ are as defined for the formula II,
in particular a group of the formula III;

(9) a compound of the formula II wherein
   R$_8$ is aryl or heteroaryl, which are either unsubstituted or substituted, the substituents being selected from the group consisting of halogen, NO$_2$, CN, C$_1$–C$_4$-alkyl, C$_3$–C$_6$-cycloalkyl, C$_1$–C$_4$-alkoxy and C$_1$–C$_4$-alkylthio;
in particular unsubstituted aryl.

Especially preferred according to the invention are the compounds of the formula II mentioned in the Examples.

The reactions described hereinbefore and hereinafter are carried out in a customary manner, for example in the absence or usually in the presence of a suitable solvent or diluent or a mixture thereof, working as the occasion demands with cooling, at room temperature or with heating, for example at a temperature in the range of from about −80° C. to the boiling point of the reaction medium, preferably at about −20° C. to about +150° C., and, if necessary, in a closed vessel, at elevated pressure, in an inert-gas atmosphere and/or under anhydrous conditions. Especially advantageous reaction conditions are discernible from the Examples.

The starting materials listed hereinbefore and hereinafter used for preparing the compounds I, as the case may be in their free form or as salts, are known or, if they are novel, can be prepared by known methods, for example according to the following specifications.

Variant a)

Suitable halogenating agents are for example elemental chlorine, Javelle water, polysulfur dichloride, sulfur dichloride, phosphorus trichloride, phosphorus pentachloride or mixtures of two or more than two of these compounds, preferably elemental chlorine, Javelle water, sulfur dichloride or a mixture of these two compounds, particularly preferably elemental chlorine of Javelle water.

The reaction partners can be reacted with each other without the addition of a solvent or diluent. It may, however, be advantageous to add a solvent or a diluent or a mixture thereof, in which case the amount thereof is not critical. Examples of such solvents or diluents are: water; alcohols, such as methanol, ethanol, propanol, isopropanol, butanol, ethylene glycol or glycerol; aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, carbon tetrachloride, dichloroethane, trichloroethene or tetrachioroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; amides, such as N,N-dimethylformamide, N,N-diethylformamide, N,N-dimethylacetamide, N-methylpyrrolidone or hexamethylphosphoric triamide; nitriles, such as acetonitrile or propionitrile; and sulphoxides, such as dimethyl sulphoxide. The reaction is preferably carried out in the presence of a halogenated hydrocarbon, in particular dichloromethane or chlorobenzene.

The reaction is advantageously carried out at a temperature in the range of from about −20° C. to about +180° C., preferably from about 0° C. to about +80° C., in many instances in the range between room temperature and the reflux temperature of the reaction mixture.

In a preferred embodiment of variant a), a compound II is reacted at −10° C. to 40° C., preferably 0° C., with a chlorinating agent, preferably Javelle water.

The reaction is preferably carried out at atmospheric pressure.

The reaction time is not critical; preference is given to a reaction time of 0.1 to 48 hours, in particular 0.5 to 24 hours.

The product is isolated by customary methods, for example filtration, crystallization, distillation or chromatography or any suitable combination of these procedures.

The yields obtained are generally good.

Variant b1)

Suitable leaving groups $X_1$ in the compounds IV are for example hydroxy, $C_1$-$C_8$alkoxy, halo-$C_1$-$C_8$alkoxy, $C_1$-$C_8$alkanoyloxy, mercapto, $C_1$-$C_8$alkylthio, halo-$C_1$-$C_8$alkylthio, $C_1$-$C_8$alkanesulfonyloxy, halo-$C_1$-$C_8$alkanesulfonyloxy, benzenesulfonyloxy, toluenesulfonyloxy and halogen, preferably toluenesulfonyloxy, tri-fluoromethanesulfonyloxy and halogen, in-particular halogen.

Bases suitable for facilitating the reaction are for example alkali metal or alkaline earth metal hydroxides, hydrides, amides, alkanolates, acetates, carbonates, dialkylamides or alkylsilylamides, alkylamines, alkylenediamines, free or N-alkylated, saturated or unsaturated cycloalkylamines, basic heterocycles, ammonium hydroxides and also carbocyclic amines. Examples are sodium hydroxide, sodium hydride, sodium amide, sodium methanolate, sodium acetate, sodium carbonate, potassium tert-butanolate, potassium hydroxide, potassium carbonate, potassium hydride, lithium diisopropylamide, potassium bis(trimethylsilyl)amide, calciumhydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and also 1,5-diazabicyclo[5.4.0]undec-5-ene (DBU).

The reaction partners can be reacted with each other as such, i.e. without the addition of a solvent or diluent, for example in the melt. In most instances, however, the addition of a solvent or diluent or a mixture thereof is advantageous. Examples of such solvents or diluents are: water; aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, carbon tetrachloride, dichloroethene, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric triamide; nitriles, such as acetonitrile or propionitrile; and sulphoxides, such as dimethyl sulphoxide. If the reaction is carried out in the presence of a base then bases such as triethylamine, pyridine, N-methylmorpholine or N,N-diethylaniline employed in excess may also serve as solvents or diluents.

The reaction can also be carried out in a heterogeneous two-phase mixture, for example a mixture of an organic solvent and an aqueous solution of a base, if necessary in the presence of a phase-transfer catalyst such as a crown ether or a tetraalkylammonium salt.

The reaction is advantageously carried out at a temperature in the range of from about 0° C. to about +180° C., preferably from about +10° C. to about +80° C., in many instances in the range between room temperature and the reflux temperature of the reaction mixture.

In a preferred embodiment of variant b1), a compound IV is reacted at 0° C. to 120° C., preferably 20° C. to 80° C., in particular 60° C. to 80° C., in an amide, preferably N,N-dimethylformamide, with a compound V.

The reaction is preferably carried out at atmospheric pressure.

The reaction time is not critical; preference is given to a reaction time of 0.1 to 48 hours, in particular 0.5 to 24 hours.

The product is isolated by customary methods, for example filtration, crystallization, distillation or chromatography or any suitable combination of these procedures.

The yields obtained are generally good.

Variant b2)

Suitable halogenating agents are for example of the kind stated under variant a).

The reaction partners can be reacted with each other as such, i.e. without the addition of a solvent or diluent, for example in the melt. In most instances, however, the addition of a solvent or diluent or a mixture thereof is advantageous. Suitable solvents or diluents are for example of the kind stated under variant a).

The reaction is advantageously carried out at a temperature in the range of from about −20° C. to about +180° C., preferably from about 0° C. to about +80° C., in many instances between room temperature and the reflux temperature of the reaction mixture.

In a preferred embodiment of variant b2), a compound II is reacted with a chlorinating agent, preferably elemental chlorine or Javelle water, at −10° C. to 40° C., preferably 0° C.

The reaction is preferably carried out at atmospheric pressure.

The reaction time is not critical; preference is given to a reaction time of 0.1 to 48 hours, in particular 0.5 to 24 hours.

The product is isolated by customary methods, for example filtration, crystallization, distillation or chromatography or any suitable combination of these procedures.

The yields obtained are generally good.

Novel starting materials or intermediates, in each case either in their free form or as salts, that are used according to the invention for preparing compounds of the formulae I, II, IV or VII or their salts, respectively, a process for their preparation and their use as starting materials or intermediates for preparing the compounds I, II, IV or VII also form part of the subject-matter of the invention.

The compounds II can be prepared for example as described under variant b1).

Compounds of the formula IV can be prepared for example by reacting a compound of the formula

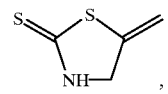

(VI)

which is known, with a compound of the formula $R_6X_2$ in which $R_6$ has the meanings stated for the formula II and $X_2$ is a leaving group, and subsequently reacting with a compound of the formula $QX_1$ in which Q is an acidic group, for example a preferably inorganic acid function such as in particular $SO_2X_1$, and $X_1$ has the meanings stated for the formula IV, to give compounds of the formula IV in which n is 0 which can, if desired, be converted further to compounds of the formula IV in which n is 1 or 2 by using an oxidizing agent such as in particular hydrogen peroxide.

The compounds of the formula IV can—for instance—also be obtained by reacting a compound of the formula

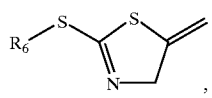

(VII)

wherein R₆ has the meanings given for formula II, with a compound of the formula QX₁, wherein Q is an acidic group, preferably an inorganic acidic group, such as $SO_2X_1$, and X₁ has the meanings given for formula II, in order to obtain a compound of the formula IV, wherein n 0 ist, and—if desired—further reacting the compound of the formula IV, wherein n is 0, with an oxidizing agent, such as hydrogenperoxid, in order to obtain a compound of the formula IV, wherein n is 1 or 2.

The compounds of the formula VII can for instance be obtained by reacting a compound of the formula VI with a compound of the formula R₆X₂, wherein R₆ has the meaning as given for formula II and X₂ is a leaving group, preferably in the presence of a base.

The invention relates to all those embodiments of the process which are based on starting materials or intermediates obtainable from any stage of the process and in which all or some of the missing steps are carried out or in which a starting material is used or, in particular, formed under the reaction conditions in the form of a derivative or salt and/or its racemates or enantiomers.

The invention relates in particular to the processes described in Examples H1 to H8.

The Examples that follow more particularly describe the invention. They do not limit the invention. Temperatures are stated in degrees centigrade. Percentages represent "percent by weight", unless indicated otherwise.

EXAMPLES

Example H1
2-Benzylthio-5-chloromethyl-thiazole (Compound No. 1.9 in Table 1)

3.2 g of 2-benzylthio-5-methylene-4H-thiazoline are dissolved in 50 ml of dichloromethane, and 0.9 g of pulverulent sodium bicarbonate are added with stirring. The mixture is subsequently cooled in an ice bath, 1.92 g of sulfuryl chloride in 5 ml of dichloromethane are added dropwise, and stirring is then continued for a further 45 minutes. The reaction mixture is filtered, the filtrate is evaporated, and the residue is recrystallized from petroleum ether, yielding 1.4 g of the title compound in the form of crystals melting at 57 to 58°.

Example H2
3-(2-Benzylthiothiazol-5-ylmethyl)-5-methyl-4-nitroimino-perhydro-1,3,5-oxadiazine (Compound No. 2.9 in Table 2)

0.8 g of 2-benzylthio-5-chloromethyl-thiazole, 0.35 g of 3 methyl-4 nitroimino-perhydro-1,3,5-oxadiazine and 0.8 g of pulverulent potassium carbonate are mixed in 40 ml of N,N-dimethylformamide, and the mixture is stirred at 60° for 2 hours. The reaction mixture is filtered, the filtrate is evaporated under reduced pressure, and the residue is digested in diethyl etherlisopropanol (5:1), yielding 0.6 g of the title compound in the form of crystals melting at 140 to 145° (decomposition).

Example H3
3-(2-Chlorothiazol-5-ylmethyl)-5-methyl-4-nitroimino-perhydro-1,3,5-oxadiazine (Compound No. 11.1 in Table 11)

2 g of 3-(2-benzylthiothiazol-5-ylmethyl)-5-methyl-4-nitroimino-perhydro-1,3,5-oxadiazine are dissolved in a mixture of 10 ml of 4N aqueous hydrochloric acid, 20 g of ice and 30 ml of dichloromethane, and 30 g of Javelle water are added dropwise with stirring to the solution. After stirring for a further 30 minutes, the organic phase is separated off, the aqueous phase is extracted repeatedly with a little dichloromethane, and the combined organic phases are subsequently dried with sodium sulphate and evaporated under reduced pressure. The oily residue is dissolved in tetrahydrofuran and precipitated with hexane, whereby the product deposits on the walls of the vessel as a sticky material. The solvent is decanted, the residue is redissolved in tetrahydrofuran, and the solution is slowly concentrated, yielding 0.84 g of the title compound in the form of a semi-crystalline resin. A sample of this resin is purified by chromatography [silica gel; dichloromethane/methanol (95:5)], yielding crystals melting at 132 to 135°.

Example H4
3-(2-Chlorothiazol-5-ylmethyl)-5-methyl-4-nitroimino-perhydro-1,3,5-oxadiazine (Compound No. 11.1 in Table 11)

To a mixture of 300 g of aqueous hydrochloric acid (32%) and 150 g of chlorobenzene are added with stirring 183 g of 5-methyl-4-nitroimino-3-(2-phenylthiothiazol-5-ylmethyl)-perhydro-1,3,5-oxadiazine within 5 minutes. 124 g of chlorine are then passed into the mixture at 20 to 25° over a period of 4 hours. After stirring for a further 2 hours, the excess of chlorine is removed by introduction of nitrogen, and the aqueous phase (containing the title compound in hydrochloride form) is separated off and adjusted to pH 5 with aqueous sodium hydroxide solution (30%). The crystalline precipitate is filtered off, washed with water and dried at 50° in vacuo, yielding 132 g of the title compound (purity: 97%) melting at 132 to 135°.

Example H5
3-(2-Chlorothiazol-5-ylmethyl)-5-methyl-4-nitroimino-perhydro-1,3,5-oxadiazine (Compound No. 11.1 in Table 11)

To a mixture of 300 g of aqueous hydrochloric acid (32%) and 150 g of chlorobenzene are added with stirring 186 g of 3-(2-cyclohexylthiothiazol-5-ylmethyl)-5-methyl-4-nitroimino-perhydro-1,3,5-oxadiazine within 5 minutes. 124 g of chlorine are then passed into the mixture at 20 to 25° over a period of 4 hours. After stirring for a further 2 hours, the excess of chlorine is removed by introduction of nitrogen, and the aqueous phase (containing the title compound in hydrochloride form) is separated off and adjusted to pH 5 with aqueous sodium hydroxide solution (30%). The crystalline precipitate is filtered off, washed with water and dried at 50° in vacuo, yielding 135 g of the title compound (purity: 97%) melting at 132 to 135°.

Example H6
3-(2-Chlorothiazol-5-ylmethyl)-5-methyl-4-nitroimino-perhydro-1,3,5-oxadiazine (Compound No. 11.1 in Table 11)

To a mixture of 300 g of aqueous hydrochloric acid (32%) and 150 g of chlorobenzene are added with stirring 190 g of 3-(2-benzylthiothiazol-5-ylmethyl)-5-methyl-4 -nitroimino-perhydro-1,3,5-oxadiazine within 5 minutes. 124 g of chlorine are then passed into the mixture at 20 to 25° over a period of 4 hours. After stirring for a further 2 hours, the excess of chlorine is removed by introduction of nitrogen, and the aqueous phase (containing the title compound in hydrochloride form) is separated off and adjusted to pH 5 with aqueous sodium hydroxide solution (30%). The crystalline precipitate is filtered off, washed with water and dried at 50° in vacuo, yielding 120 g of the title compound (purity: 97%) melting at 132 to 135°.

Example H7
2-Benzylthio-5-methylene-4H-thiazoline (Compound No. 1.8 in Table 1a)

A mixture of 6.5 g of 5-methylene-2-thioxo-thiazolidine, 17.3 g of pulverulent potassium carbonate, 9.4 g of benzyl bromide and 200 ml of acetonitrile is stirred for 1 hour at 65°. The mixture is allowed to cool to room temperature and is then filtered, and the filtrate is evaporated to dryness in vacuo. The residue is purified by chromatography [silica gel; hexane/diethyl ether (1:1)], yielding 7.7 g of the title compound in the form of a colourless oil.

Example H8

Analogously to the procedures described in Examples H1 to H7, also the other compounds listed in Tables 1 to 13 can be prepared. The temperatures stated in the column "Physical data" of these tables in each case denote the melting point of the respective compound; "decomp." means decomposition.

TABLE 1

$$R_6\overset{(O)_n}{\underset{\|}{S}}{-}\underset{N}{\overset{S}{\diagup\!\!\!\diagdown}}{-}CH_2{-}X_1$$

| Compound No. | n | $X_1$ | $R_5$ | Physical data |
|---|---|---|---|---|
| 1.1 | 0 | Cl | $CH_3$ | |
| 1.2 | 0 | Cl | $C_2H_5$ | |
| 1.3 | 0 | Cl | $n\text{-}C_3H_7$ | |
| 1.4 | 0 | Cl | $i\text{-}C_3H_7$ | |
| 1.5 | 0 | Cl | $n\text{-}C_4H_9$ | |
| 1.6 | 0 | Cl | $t\text{-}C_4H_9$ | |
| 1.7 | 0 | Cl | $cyclo\text{-}C_3H_5$ | |
| 1.8 | 0 | Cl | $CH_2C_6H_5$ | 57–58° (hydrochloride: 129–131°) |
| 1.9 | 0 | Cl | $CH_2C_6H_4\text{-}4\text{-}CH_3$ | |
| 1.10 | 0 | Cl | $CH_2C_6H_4\text{-}4\text{-}OCH_3$ | |
| 1.11 | 0 | Cl | $CH_2C_6H_4\text{-}4\text{-}Cl$ | |
| 1.12 | 0 | Cl | $CH_2C_6H_4\text{-}4\text{-}NO_2$ | |
| 1.13 | 0 | Cl | $CH_2\text{-}2\text{-furyl}$ | |
| 1.14 | 0 | Cl | $CH_2\text{-}2\text{-thienyl}$ | |
| 1.15 | 0 | Cl | $C_6H_5$ | |
| 1.16 | 0 | Cl | $C_6H_4\text{-}4\text{-}CH_3$ | |
| 1.17 | 0 | Cl | $C_6H_4\text{-}4\text{-}OCH_3$ | |
| 1.18 | 0 | Cl | $C_6H_4\text{-}4\text{-}Cl$ | |
| 1.19 | 0 | Cl | $C_6H_4\text{-}4\text{-}NO_2$ | |
| 1.20 | 0 | Cl | $CH_2CH{=}CH_2$ | |
| 1.21 | 0 | Cl | $CH_2C{\equiv}CH$ | |
| 1.22 | 0 | Cl | $CH_2CH{=}CHC_6H_5$ | |
| 1.23 | 0 | Cl | $CH_2C{\equiv}CC_6H_5$ | |
| 1.24 | 0 | Cl | $SCH_3$ | |
| 1.25 | 0 | Cl | $SC_2H_5$ | |
| 1.26 | 0 | Cl | $S\text{-}n\text{-}C_3H_7$ | |
| 1.27 | 0 | Cl | $S\text{-}i\text{-}C_3H_7$ | |
| 1.28 | 0 | Cl | $S\text{-}n\text{-}C_4H_9$ | |
| 1.29 | 0 | Cl | $S\text{-}t\text{-}C_4H_9$ | |
| 1.30 | 0 | Cl | $S\text{-}cyclo\text{-}C_3H_5$ | |
| 1.31 | 0 | Cl | $SCH_2C_6H_5$ | |
| 1.32 | 0 | Cl | $SCH_2C_6H_4\text{-}4\text{-}CH_3$ | |
| 1.33 | 0 | Cl | $SCH_2C_6H_4\text{-}4\text{-}OCH_3$ | |
| 1.34 | 0 | Cl | $SCH_2C_6H_4\text{-}4\text{-}Cl$ | |
| 1.35 | 0 | Cl | $SCH_2C_6H_4\text{-}4\text{-}NO_2$ | |
| 1.36 | 0 | Cl | $SCH_2\text{-}2\text{-furyl}$ | |
| 1.37 | 0 | Cl | $SCH_2\text{-}2\text{-thienyl}$ | |
| 1.38 | 0 | Cl | $SC_6H_5$ | |
| 1.39 | 0 | Cl | $SC_6H_4\text{-}4\text{-}CH_3$ | |
| 1.40 | 0 | Cl | $SC_6H_4\text{-}4\text{-}OCH_3$ | |
| 1.41 | 0 | Cl | $SC_6H_4\text{-}4\text{-}Cl$ | |
| 1.42 | 0 | Cl | $SC_6H_4\text{-}4\text{-}NO_2$ | |
| 1.43 | 0 | Cl | $SCH_2CH{=}CH_2$ | |
| 1.44 | 0 | Cl | $SCH_2C{\equiv}CH$ | |
| 1.45 | 0 | Cl | $SCH_2CH{=}CHC_6H_5$ | |
| 1.46 | 0 | Cl | $SCH_2C{\equiv}CC_6H_5$ | |

TABLE 1-continued

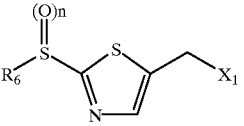

| Compound No. | n | X₁ | R₅ | Physical data |
|---|---|---|---|---|
| 1.47 | 0 | Cl | | |

[Structure shown for 1.47]

| | | | | |
|---|---|---|---|---|
| 1.48 | 1 | Cl | $CH_3$ | |
| 1.49 | 1 | Cl | $C_2H_5$ | |
| 1.50 | 1 | Cl | $n\text{-}C_3H_7$ | |
| 1.51 | 1 | Cl | $i\text{-}C_3H_7$ | |
| 1.52 | 1 | Cl | $n\text{-}C_4H_9$ | |
| 1.53 | 1 | Cl | $t\text{-}C_4H_9$ | |
| 1.54 | 1 | Cl | cyclo-$C_3H_5$ | |
| 1.55 | 1 | Cl | $CH_2C_6H_5$ | |
| 1.56 | 1 | Cl | $CH_2C_6H_4\text{-}4\text{-}CH_3$ | |
| 1.57 | 1 | Cl | $CH_2C_6H_4\text{-}4\text{-}OCH_3$ | |
| 1.58 | 1 | Cl | $CH_2C_6H_4\text{-}4\text{-}Cl$ | |
| 1.59 | 1 | Cl | $CH_2C_6H_4\text{-}4\text{-}NO_2$ | |
| 1.60 | 1 | Cl | $CH_2\text{-}2\text{-furyl}$ | |
| 1.61 | 1 | Cl | $CH_2\text{-}2\text{-thienyl}$ | |
| 1.62 | 1 | Cl | $C_6H_5$ | |
| 1.63 | 1 | Cl | $C_6H_4\text{-}4\text{-}CH_3$ | |
| 1.64 | 1 | Cl | $C_6H_4\text{-}4\text{-}OCH_3$ | |
| 1.65 | 1 | Cl | $C_6H_4\text{-}4\text{-}Cl$ | |
| 1.66 | 1 | Cl | $C_6H_4\text{-}4\text{-}NO_2$ | |
| 1.67 | 1 | Cl | $CH_2CH{=}CH_2$ | |
| 1.68 | 1 | Cl | $CH_2C{\equiv}CH$ | |
| 1.69 | 1 | Cl | $CH_2CH{=}CHC_6H_5$ | |
| 1.70 | 1 | Cl | $CH_2C{\equiv}CC_6H_5$ | |
| 1.71 | 2 | Cl | $CH_3$ | |
| 1.72 | 2 | Cl | $C_2H_5$ | |
| 1.73 | 2 | Cl | $n\text{-}C_3H_7$ | |
| 1.74 | 2 | Cl | $i\text{-}C_3H_7$ | |
| 1.75 | 2 | Cl | $n\text{-}C_4H_9$ | |
| 1.76 | 2 | Cl | $t\text{-}C_4H_9$ | |
| 1.77 | 2 | Cl | cyclo-$C_3H_5$ | |
| 1.78 | 2 | Cl | $CH_2C_6H_5$ | |
| 1.79 | 2 | Cl | $CH_2C_6H_4\text{-}4\text{-}CH_3$ | |
| 1.80 | 2 | Cl | $CH_2C_6H_4\text{-}4\text{-}OCH_3$ | |
| 1.81 | 2 | Cl | $CH_2C_6H_4\text{-}4\text{-}Cl$ | |
| 1.82 | 2 | Cl | $CH_2C_6H_4\text{-}4\text{-}NO_2$ | |
| 1.83 | 2 | Cl | $CH_2\text{-}2\text{-furyl}$ | |
| 1.84 | 2 | Cl | $CH_2\text{-}2\text{-thienyl}$ | |
| 1.85 | 2 | Cl | $C_6H_5$ | |
| 1.86 | 2 | Cl | $C_6H_4\text{-}4\text{-}CH_3$ | |
| 1.87 | 2 | Cl | $C_6H_4\text{-}4\text{-}OCH_3$ | |
| 1.88 | 2 | Cl | $C_6H_4\text{-}4\text{-}Cl$ | |
| 1.89 | 2 | Cl | $C_6H_4\text{-}4\text{-}NO_2$ | |
| 1.90 | 2 | Cl | $CH_2CH{=}CH_2$ | |
| 1.91 | 2 | Cl | $CH_2C{\equiv}CH$ | |
| 1.92 | 2 | Cl | $CH_2CH{=}CHC_6H_5$ | |
| 1.93 | 2 | Cl | $CH_2C{\equiv}CC_6H_5$ | |
| 1.94 | 0 | Cl | $CH_2SCH_3$ | |
| 1.95 | 0 | Cl | $CH_2SC_2H_5$ | |
| 1.96 | 0 | Cl | $CH_2S\text{-}n\text{-}C_3H_7$ | |
| 1.97 | 0 | Cl | $CH_2S\text{-}i\text{-}C_3H_7$ | |
| 1.98 | 0 | Cl | $CH_2S\text{-}n\text{-}C_4H_9$ | |
| 1.99 | 0 | Cl | $CH_2S\text{-}t\text{-}C_4H_9$ | |
| 1.100 | 0 | Cl | $CH_2S\text{-cyclo-}C_3H_5$ | |
| 1.101 | 0 | Cl | $CH_2SCH_2C_6H_5$ | |
| 1.102 | 0 | Cl | $CH_2SCH_2C_6H_4\text{-}4\text{-}CH_3$ | |
| 1.103 | 0 | Cl | $CH_2SCH_2C_6H_4\text{-}4\text{-}OCH_3$ | |
| 1.104 | 0 | Cl | $CH_2SCH_2C_6H_4\text{-}4\text{-}Cl$ | |
| 1.105 | 0 | Cl | $CH_2SCH_2C_6H_4\text{-}4\text{-}NO_2$ | |
| 1.106 | 0 | Cl | $CH_2SCH_2\text{-}2\text{-furyl}$ | |
| 1.107 | 0 | Cl | $CH_2SCH_2\text{-}2\text{-thienyl}$ | |

TABLE 1-continued $$R_6-\overset{(O)_n}{\underset{\|}{S}}-\underset{N}{\overset{S}{\langle}}-CH_2-X_1$$

| Compound No. | n | X$_1$ | R$_5$ | Physical data |
|---|---|---|---|---|
| 1.108 | 0 | Cl | CH$_2$SC$_6$H$_5$ | |
| 1.109 | 0 | Cl | CH$_2$SC$_6$H$_4$-4-CH$_3$ | |
| 1.110 | 0 | Cl | CH$_2$SC$_6$H$_4$-4-OCH$_3$ | |
| 1.111 | 0 | Cl | CH$_2$SC$_6$H$_4$-4-Cl | |
| 1.112 | 0 | Cl | CH$_2$SC$_6$H$_4$-4-NO$_2$ | |
| 1.113 | 0 | Cl | CH$_2$SCH$_2$CH=CH$_2$ | |
| 1.114 | 0 | Cl | CH$_2$SCH$_2$C≡CH | |
| 1.115 | 0 | Cl | CH$_2$SCH$_2$CH=CHC$_6$H$_5$ | |
| 1.116 | 0 | Cl | CH$_2$SCH$_2$C≡CC$_6$H$_5$ | |
| 1.117 | 0 | Cl | | |

[Structure: CH$_3$S-thiazole-CH$_2$-N(cyclic tetrahydropyrimidine with =N-NO$_2$ and NH)]

| Compound No. | n | X$_1$ | R$_5$ | Physical data |
|---|---|---|---|---|
| 1.118 | 0 | Br | CH$_3$ | |
| 1.119 | 0 | Br | C$_2$H$_5$ | |
| 1.120 | 0 | Br | n-C$_3$H$_7$ | |
| 1.121 | 0 | Br | i-C$_3$H$_7$ | |
| 1.122 | 0 | Br | n-C$_4$H$_9$ | |
| 1.123 | 0 | Br | t-C$_4$H$_9$ | |
| 1.124 | 0 | Br | cyclo-C$_3$H$_5$ | |
| 1.125 | 0 | Br | CH$_2$C$_6$H$_5$ | |
| 1.126 | 0 | Br | CH$_2$C$_6$H$_4$-4-CH$_3$ | |
| 1.127 | 0 | Br | CH$_2$C$_6$H$_4$-4-OCH$_3$ | |
| 1.128 | 0 | Br | CH$_2$C$_6$H$_4$-4-Cl | |
| 1.129 | 0 | Br | CH$_2$C$_6$H$_4$-4-NO$_2$ | |
| 1.130 | 0 | Br | CH$_2$-2-furyl | |
| 1.131 | 0 | Br | CH$_2$-2-thienyl | |
| 1.132 | 0 | Br | C$_6$H$_5$ | 99–102° |
| 1.133 | 0 | Br | C$_6$H$_4$-4-CH$_3$ | |
| 1.134 | 0 | Br | C$_6$H$_4$-4-OCH$_3$ | |
| 1.135 | 0 | Br | C$_6$H$_4$-4-Cl | |
| 1.136 | 0 | Br | C$_6$H$_4$-4-NO$_2$ | |
| 1.137 | 0 | Br | CH$_2$CH=CH$_2$ | |
| 1.138 | 0 | Br | CH$_2$C≡CH | |
| 1.139 | 0 | Br | CH$_2$CH=CHC$_6$H$_5$ | |
| 1.140 | 0 | Br | CH$_2$C≡CC$_6$H$_5$ | |
| 1.141 | 0 | Br | SCH$_3$ | |
| 1.142 | 0 | Br | SC$_2$H$_5$ | |
| 1.143 | 0 | Br | S-n-C$_3$H$_7$ | |
| 1.144 | 0 | Br | S-i-C$_3$H$_7$ | |
| 1.145 | 0 | Br | S-n-C$_4$H$_9$ | |
| 1.146 | 0 | Br | S-t-C$_4$H$_9$ | |
| 1.147 | 0 | Br | S-cyclo-C$_3$H$_5$ | |
| 1.148 | 0 | Br | SCH$_2$C$_6$H$_5$ | |
| 1.149 | 0 | Br | SCH$_2$C$_6$H$_4$-4-CH$_3$ | |
| 1.150 | 0 | Br | SCH$_2$C$_6$H$_4$-4-OCH$_3$ | |
| 1.151 | 0 | Br | SCH$_2$C$_6$H$_4$-4-Cl | |
| 1.152 | 0 | Br | SCH$_2$C$_6$H$_4$-4-NO$_2$ | |
| 1.153 | 0 | Br | SCH$_2$-2-furyl | |
| 1.154 | 0 | Br | SCH$_2$-2-thienyl | |
| 1.155 | 0 | Br | SC$_6$H$_5$ | |
| 1.156 | 0 | Br | SC$_6$H$_4$-4-CH$_3$ | |
| 1.157 | 0 | Br | SC$_6$H$_4$-4-OCH$_3$ | |
| 1.158 | 0 | Br | SC$_6$H$_4$-4-Cl | |
| 1.159 | 0 | Br | SC$_6$H$_4$-4-NO$_2$ | |
| 1.160 | 0 | Br | SCH$_2$CH=CH$_2$ | |
| 1.161 | 0 | Br | SCH$_2$C≡CH | |
| 1.162 | 0 | Br | SCH$_2$CH=CHC$_6$H$_5$ | |
| 1.163 | 0 | Br | SCH$_2$C≡CC$_6$H$_5$ | |

TABLE 1-continued $$R_6-\underset{\underset{N}{\overset{(O)_n}{\underset{\|}{S}}}}{\overset{S}{\bigtriangleup}}-CH_2-X_1$$

| Compound No. | n | $X_1$ | $R_5$ | Physical data |
|---|---|---|---|---|
| 1.164 | 0 | Br | (structure shown below) | |

(structure for 1.164: 2-mercapto-thiazol-5-ylmethyl attached to N of tetrahydropyrimidine bearing =N-NO₂ and NH)

| Compound No. | n | $X_1$ | $R_5$ |
|---|---|---|---|
| 1.165 | 1 | Br | $CH_3$ |
| 1.166 | 1 | Br | $C_2H_5$ |
| 1.167 | 1 | Br | $n\text{-}C_3H_7$ |
| 1.168 | 1 | Br | $i\text{-}C_3H_7$ |
| 1.169 | 1 | Br | $n\text{-}C_4H_9$ |
| 1.170 | 1 | Br | $t\text{-}C_4H_9$ |
| 1.171 | 1 | Br | cyclo-$C_3H_5$ |
| 1.172 | 1 | Br | $CH_2C_6H_5$ |
| 1.173 | 1 | Br | $CH_2C_6H_4\text{-}4\text{-}CH_3$ |
| 1.174 | 1 | Br | $CH_2C_6H_4\text{-}4\text{-}OCH_3$ |
| 1.175 | 1 | Br | $CH_2C_6H_4\text{-}4\text{-}Cl$ |
| 1.176 | 1 | Br | $CH_2C_6H_4\text{-}4\text{-}NO_2$ |
| 1.177 | 1 | Br | $CH_2\text{-}2\text{-}furyl$ |
| 1.178 | 1 | Br | $CH_2\text{-}2\text{-}thienyl$ |
| 1.179 | 1 | Br | $C_6H_5$ |
| 1.180 | 1 | Br | $C_6H_4\text{-}4\text{-}CH_3$ |
| 1.181 | 1 | Br | $C_6H_4\text{-}4\text{-}OCH_3$ |
| 1.182 | 1 | Br | $C_6H_4\text{-}4\text{-}Cl$ |
| 1.183 | 1 | Br | $C_6H_4\text{-}4\text{-}NO_2$ |
| 1.184 | 1 | Br | $CH_2CH{=}CH_2$ |
| 1.185 | 1 | Br | $CH_2C{\equiv}CH$ |
| 1.186 | 1 | Br | $CH_2CH{=}CHC_6H_5$ |
| 1.187 | 1 | Br | $CH_2C{\equiv}CC_6H_5$ |
| 1.188 | 2 | Br | $CH_3$ |
| 1.189 | 2 | Br | $C_2H_5$ |
| 1.190 | 2 | Br | $n\text{-}C_3H_7$ |
| 1.191 | 2 | Br | $i\text{-}C_3H_7$ |
| 1.192 | 2 | Br | $n\text{-}C_4H_9$ |
| 1.193 | 2 | Br | $t\text{-}C_4H_9$ |
| 1.194 | 2 | Br | cyclo-$C_3H_5$ |
| 1.195 | 2 | Br | $CH_2C_6H_5$ |
| 1.196 | 2 | Br | $CH_2C_6H_4\text{-}4\text{-}CH_3$ |
| 1.197 | 2 | Br | $CH_2C_6H_4\text{-}4\text{-}OCH_3$ |
| 1.198 | 2 | B r | $CH_2C_6H_4\text{-}4\text{-}Cl$ |
| 1.199 | 2 | Br | $CH_2C_6H_4\text{-}4\text{-}NO_2$ |
| 1.200 | 2 | Br | $CH_2\text{-}2\text{-}furyl$ |
| 1.201 | 2 | Br | $CH_2\text{-}2\text{-}thienyl$ |
| 1.202 | 2 | Br | $C_6H_5$ |
| 1.203 | 2 | Br | $C_6H_4\text{-}4\text{-}CH_3$ |
| 1.204 | 2 | Br | $C_6H_4\text{-}4\text{-}OCH_3$ |
| 1.205 | 2 | Br | $C_6H_4\text{-}4\text{-}Cl$ |
| 1.206 | 2 | Br | $C_6H_4\text{-}4\text{-}NO_2$ |
| 1.207 | 2 | Br | $CH_2CH{=}CH_2$ |
| 1.208 | 2 | Br | $CH_2C{\equiv}CH$ |
| 1.209 | 2 | Br | $CH_2CH{=}CHC_6H_5$ |
| 1.210 | 2 | Br | $CH_2{\equiv}CC_6H_5$ |
| 1.211 | 0 | Br | $CH_2SCH_3$ |
| 1.212 | 0 | Br | $CH_2SC_2H_5$ |
| 1.213 | 0 | Br | $CH_2S\text{-}n\text{-}C_3H_7$ |
| 1.214 | 0 | Br | $CH_2S\text{-}i\text{-}C_3H_7$ |
| 1.215 | 0 | Br | $CH_2S\text{-}n\text{-}C_4H_9$ |
| 1.216 | 0 | Br | $CH_2S\text{-}t\text{-}C_4H_9$ |
| 1.217 | 0 | Br | $CH_2S\text{-}cyclo\text{-}C_3H_5$ |
| 1.218 | 0 | Br | $CH_2SCH_2C_6H_5$ |
| 1.219 | 0 | Br | $CH_2SCH_2C_6H_4\text{-}4\text{-}CH_3$ |
| 1.220 | 0 | Br | $CH_2SCH_2C_6H_4\text{-}4\text{-}OCH_3$ |
| 1.221 | 0 | Br | $CH_2SCH_2C_6H_4\text{-}4\text{-}Cl$ |
| 1.222 | 0 | Br | $CH_2SCH_2C_6H_4\text{-}4\text{-}NO_2$ |
| 1.223 | 0 | Br | $CH_2SCH_2\text{-}2\text{-}furyl$ |
| 1.224 | 0 | Br | $CH_2SCH_2\text{-}2\text{-}thienyl$ |

TABLE 1-continued

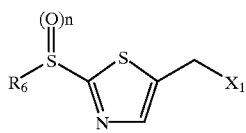

| Compound No. | n | X₁ | R₅ | Physical data |
|---|---|---|---|---|
| 1.225 | 0 | Br | $CH_2SC_6H_5$ | |
| 1.226 | 0 | Br | $CH_2SC_6H_4$-4-$CH_3$ | |
| 1.227 | 0 | Br | $CH_2SC_6H_4$-4-$OCH_3$ | |
| 1.228 | 0 | Br | $CH_2SC_6H_4$-4-Cl | |
| 1.229 | 0 | Br | $CH_2SC_6H_4$-4-$NO_2$ | |
| 1.230 | 0 | Br | $CH_2SCH_2CH=CH_2$ | |
| 1.231 | 0 | Br | $CH_2SCH_2C\equiv CH$ | |
| 1.232 | 0 | Br | $CH_2SCH_2CH=CHC_6H_5$ | |
| 1.233 | 0 | Br | $CH_2SCH_2C\equiv CC_6H_5$ | |
| 1.234 | 0 | Br | (structure) | |
| 1.235 | 0 | Cl | $CH_2CO_2C_2H_5$ | |
| 1.236 | 0 | Cl | cyclo-$C_6H_{11}$ | |
| 1.237 | 0 | Cl | $CH_2$—$CH_2$—$CH_2$—$CH_2$—$CH_2$—SH | |
| 1.238 | 0 | Cl | $CH_2CO_2Na$ | |
| 1.239 | 0 | Br | $CH_2CO_2C_2H_5$ | |
| 1.240 | 0 | Br | cyclo-$C_6H11$ | |
| 1.241 | 0 | Br | $CH_2$—$CH_2$—$CH_2$—$CH_2$—$CH_2$—SH | |
| 1.242 | 0 | Br | $CH_2CO_2Na$ | |
| 1.243 | 0 | Cl | (structure) | |
| 1.244 | 0 | Cl | (structure) | |
| 1.245 | 0 | Cl | (structure) | |
| 1.246 | 0 | Cl | (structure) | |

TABLE 1-continued
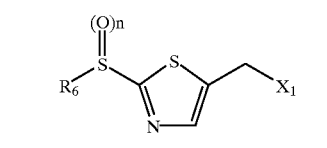
| Compound No. | n | $X_1$ | $R_5$ | Physical data |
|---|---|---|---|---|
| 1.247 | 0 | Cl | 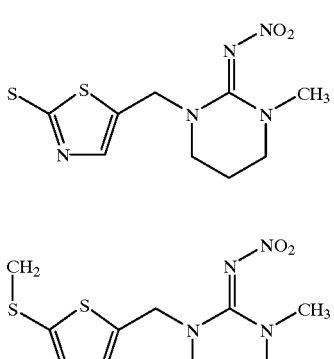 | |
| 1.248 | 0 | Cl | 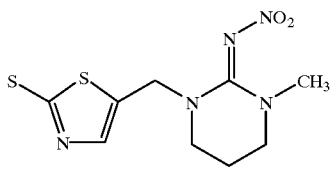 | |
| 1.249 | 0 | Cl | 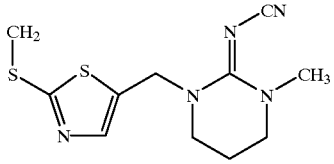 | |
| 1.250 | 0 | Cl | 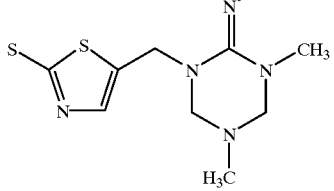 | |
| 1.251 | 0 | Cl | 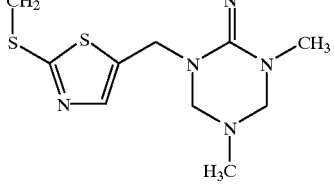 | |
| 1.252 | 0 | Cl | | |

TABLE 1-continued

| Compound No. | n | X₁ | R₅ | Physical data |
|---|---|---|---|---|
| 1.253 | 0 | Cl | (thiazol-SH with CH₂ to triazinane N-CH₃, N-CH₃, =N-CN) | |
| 1.254 | 0 | Cl | (2-(methylthiomethyl)thiazole-CH₂-triazinane with N-CH₃, N-CH₃, =N-CN) | |
| 1.255 | 0 | Cl | (thiazol-SH-CH₂-piperidine =N-NO₂) | |
| 1.256 | 0 | Cl | (2-(methylthiomethyl)thiazole-CH₂-piperidine =N-NO₂) | |
| 1.257 | 0 | Cl | (thiazol-SH-CH₂-piperidine =N-CN) | |
| 1.258 | 0 | Cl | (2-(methylthiomethyl)thiazole-CH₂-piperidine =N-CN) | |
| 1.259 | 0 | Cl | (thiazol-SH-CH₂-oxazinane =N-NO₂) | |

TABLE 1-continued
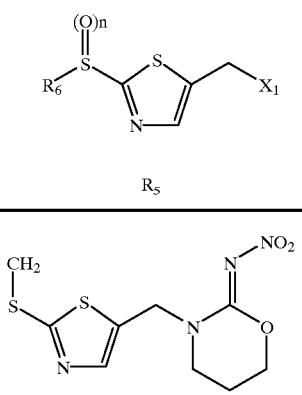
| Compound No. | n | $X_1$ | $R_5$ | Physical data |
|---|---|---|---|---|
| 1.260 | 0 | Cl | 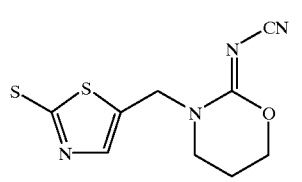 | |
| 1.261 | 0 | Cl | 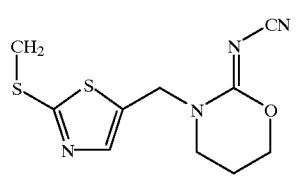 | |
| 1.262 | 0 | Cl | 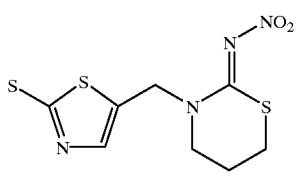 | |
| 1.263 | 0 | Cl | 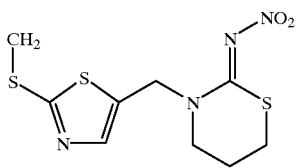 | |
| 1.264 | 0 | Cl | 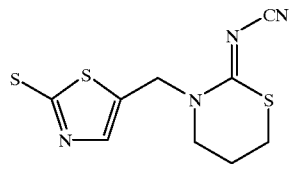 | |
| 1.265 | 0 | Cl | 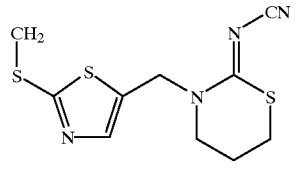 | |
| 1.266 | 0 | Cl | | |

TABLE 1-continued

| Compound No. | n | X₁ | R₅ | Physical data |
|---|---|---|---|---|
| 1.267 | 0 | Cl | | |
| 1.268 | 0 | Cl | | |
| 1.269 | 0 | Br | | |
| 1.270 | 0 | Br | | |
| 1.271 | 0 | Br | | |
| 1.272 | 0 | Br | | |
| 1.273 | 0 | Br | | |

TABLE 1-continued
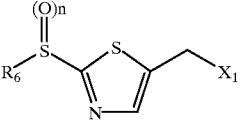
| Compound No. | n | $X_1$ | $R_5$ | Physical data |
|---|---|---|---|---|
| 1.274 | 0 | Br | 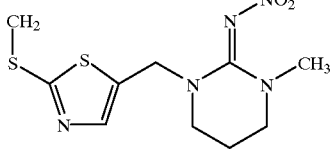 | |
| 1.275 | 0 | Br | | |
| 1.276 | 0 | Br | | |
| 1.277 | 0 | Br | 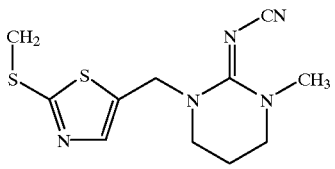 | |
| 1.278 | 0 | Br | | |
| 1.279 | 0 | Br | | |

TABLE 1-continued
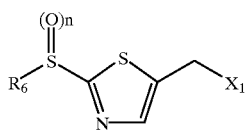
| Compound No. | n | X₁ | R₅ | Physical data |
|---|---|---|---|---|
| 1.280 | 0 | Br | 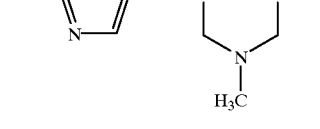 | |
| 1.281 | 0 | Br | 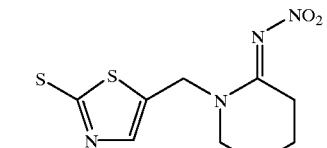 | |
| 1.282 | 0 | Br |  | |
| 1.283 | 0 | Br | 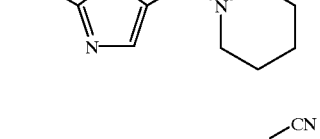 | |
| 1.284 | 0 | Br | 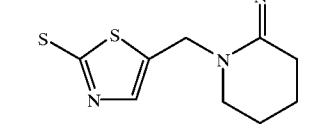 | |
| 1.285 | 0 | Br | 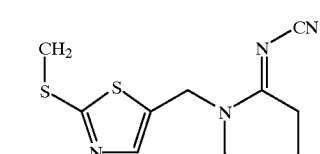 | |
| 1.286 | 0 | Br |  | |

TABLE 1-continued

| Compound No. | n | X₁ | R₅ | Physical data |
|---|---|---|---|---|
| 1.287 | 0 | Br | (2-thiazolyl-S-)-CH₂-N-ring(O,CH₂,CH₂,CH₂)-C=N-CN | |
| 1.288 | 0 | Br | (CH₃-S-CH₂-thiazolyl)-CH₂-N-ring(O)-C=N-CN | |
| 1.289 | 0 | Br | (2-thiazolyl-S-)-CH₂-N-ring(S)-C=N-NO₂ | |
| 1.290 | 0 | Br | (CH₃-S-CH₂-thiazolyl)-CH₂-N-ring(S)-C=N-NO₂ | |
| 1.291 | 0 | Br | (2-thiazolyl-S-)-CH₂-N-ring(S)-C=N-CN | |
| 1.292 | 0 | Br | (CH₃-S-CH₂-thiazolyl)-CH₂-N-ring(S)-C=N-CN | |
| 1.293 | 0 | Br | (2-thiazolyl-S-)-CH₂-N-ring(NH)-C=N-CN | |

TABLE 1-continued

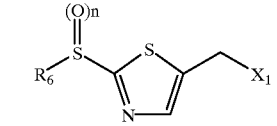

| Compound No. | n | $X_1$ | $R_5$ | Physical data |
|---|---|---|---|---|
| 1.294 | 0 | Br | 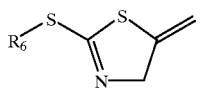 | |

TABLE 1a

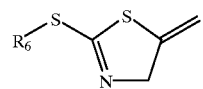

| Compound No. | $R_6$ | Physical data |
|---|---|---|
| 1.1a | $CH_3$ | oil |
| 1.2a | $C_2H_5$ | |
| 1.3a | $n-C_3H_7$ | |
| 1.4a | $i-C_3H_7$ | |
| 1.5a | $n-C_4H_9$ | |
| 1.6a | $t-C_4H_9$ | |
| 1.7a | $cyclo-C_3H_5$ | |
| 1.8a | $CH_2C_6H_5$ | oil |
| 1.9a | $CH_2C_6H_4-4-CH_3$ | |
| 1.10a | $CH_2C_6H_4-4-OCH_3$ | |
| 1.11a | $CH_2C_6H_4-4-Cl$ | |
| 1.12a | $CH_2C_6H_4-4-NO_2$ | |
| 1.13a | $CH_2-2-furyl$ | |
| 1.14a | $CH_2-2-thienyl$ | |
| 1.15a | $C_6H_5$ | |
| 1.16a | $C_6H_4-4-CH_3$ | |
| 1.17a | $C_6H_4-4-OCH_3$ | |
| 1.18a | $C_6H_4-4-Cl$ | |
| 1.19a | $C_6H_4-4-NO_2$ | |
| 1.20a | $CH_2CH=CH_2$ | $n_D^{21}$: 1.5924 |
| 1.21a | $CH_2C\equiv CH$ | |
| 1.22a | $CH_2CH=CHC_6H_5$ | |
| 1.23a | $CH_2C\equiv CC_6H_5$ | |
| 1.24a | $SCH_3$ | |
| 1.25a | $SC_2H_5$ | |
| 1.26a | $S-n-C_3H_7$ | |
| 1.27a | $S-i-C_3H_7$ | |
| 1.28a | $S-n-C_4H_9$ | |
| 1.29a | $S-t-C_4H_9$ | |
| 1.30a | $S-cyclo-C_3H_5$ | |
| 1.31a | $SCH_2C_6H_5$ | |
| 1.32a | $SCH_2C_6H_4-4-CH_3$ | |
| 1.33a | $SCH_2C_6H_4-4-OCH_3$ | |
| 1.34a | $SCH_2C_6H_4-4-Cl$ | |
| 1.35a | $SCH_2C_6H_4-4-NO_2$ | |
| 1.36a | $SCH_2-2-furyl$ | |
| 1.37a | $SCH_2-2-thienyl$ | |
| 1.38a | $SC_6H_5$ | |
| 1.39a | $SC_6H_4-4-CH_3$ | |
| 1.40a | $SC_6H_4-4-OCH_3$ | |
| 1.41a | $SC_6H_4-4-Cl$ | |
| 1.42a | $SC_6H_4-4-NO_2$ | |
| 1.43a | $SCH_2CH=CH_2$ | |
| 1.44a | $SCH_2C\equiv CH$ | |
| 1.45a | $SCH_2CH=CHC_6H_5$ | |

TABLE 1a-continued

| Compound No. | $R_6$ | Physical data |
|---|---|---|
| 1.46a | $SCH_2C\equiv CC_6H_5$ | |
| 1.47a | 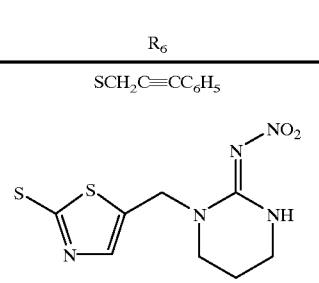 | |
| 1.48a | $CH_2SCH_3$ | |
| 1.49a | $CH_2SC_2H_5$ | |
| 1.50a | $CH_2S-n-C_3H_7$ | |
| 1.51a | $CH_2S-i-C_3H_7$ | |
| 1.52a | $CH_2S-n-C_4H_9$ | |
| 1.53a | $CH_2S-t-C_4H_9$ | |
| 1.54a | $CH_2S-cyclo-C_3H_5$ | |
| 1.55a | $CH_2SCH_2C_6H_5$ | |
| 1.56a | $CH_2SCH_2C_6H_4-4-CH_3$ | |
| 1.57a | $CH_2SCH_2C_6H_4-4-OCH_3$ | |
| 1.58a | $CH_2SCH_2C_6H_4-4-Cl$ | |
| 1.59a | $CH_2SCH_2C_6H_4-4-NO_2$ | |
| 1.60a | $CH_2SCH_2-2-furyl$ | |
| 1.61a | $CH_2SCH_2-2-thienyl$ | |
| 1.62a | $CH_2SC_6H_5$ | |
| 1.63a | $CH_2SC_6H_4-4-CH_3$ | |
| 1.64a | $CH_2SC_6H_4-4-OCH_3$ | |
| 1.65a | $CH_2SC_6H_4-4-Cl$ | |
| 1.66a | $CH_2SC_6H_4-4-NO_2$ | |
| 1.67a | $CH_2SCH_2CH=CH_2$ | |
| 1.68a | $CH_2SCH_2C\equiv CH$ | |
| 1.69a | $CH_2SCH_2CH=CHC_6H_5$ | |
| 1.70a | $CH_2SCH_2C\equiv CC_6H_5$ | |
| 1.71a | 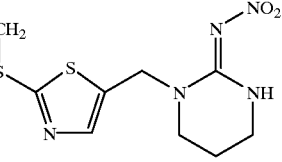 | |
| 1.72a | $CH_2CO_2C_2H_5$ | |
| 1.73a | $cyclo-C_6H_{11}$ | |

TABLE 1a-continued $$R_6-S-\underset{N}{\overset{S}{\bigvee}}=CH_2$$

| Compound No. | R$_6$ | Physical data |
|---|---|---|
| 1.74a | CH$_2$—CH$_2$—CH$_2$—CH$_2$—CH$_2$—SH | |
| 1.75a | CH$_2$CO$_2$Na | |
| 1.76a | (2-thio-thiazol-5-yl)methyl-N-methyl-N'-nitro-1,3,5-oxadiazinan-2-imine | |
| 1.77a | (2-methylthio-thiazol-5-yl)methyl-N-methyl-N'-nitro-1,3,5-oxadiazinan-2-imine | |
| 1.78a | (2-thio-thiazol-5-yl)methyl-N-methyl-N'-cyano-1,3,5-oxadiazinan-2-imine | |
| 1.79a | (2-methylthio-thiazol-5-yl)methyl-N-methyl-N'-cyano-1,3,5-oxadiazinan-2-imine | |
| 1.80a | (2-thio-thiazol-5-yl)methyl-N-methyl-N'-nitro-tetrahydropyrimidin-2-imine | |
| 1.81a | (2-methylthio-thiazol-5-yl)methyl-N-methyl-N'-nitro-tetrahydropyrimidin-2-imine | |
| 1.82a | (2-thio-thiazol-5-yl)methyl-N-methyl-N'-nitro-tetrahydropyrimidin-2-imine | |
| 1.83a | (2-methylthio-thiazol-5-yl)methyl-N-methyl-N'-cyano-tetrahydropyrimidin-2-imine | |
| 1.84a | (2-thio-thiazol-5-yl)methyl-N,N''-dimethyl-N'-nitro-1,3,5-triazinan-2-imine | |
| 1.85a | (2-methylthio-thiazol-5-yl)methyl-N,N''-dimethyl-N'-nitro-1,3,5-triazinan-2-imine | |
| 1.86a | (2-thio-thiazol-5-yl)methyl-N,N''-dimethyl-N'-cyano-1,3,5-triazinan-2-imine | |
| 1.87a | (2-methylthio-thiazol-5-yl)methyl-N,N''-dimethyl-N'-cyano-1,3,5-triazinan-2-imine | |
| 1.88a | (2-thio-thiazol-5-yl)methyl-N'-nitro-piperidin-2-imine | |

TABLE 1a-continued
| Compound No. | R₆ | Physical data |
|---|---|---|
| 1.89a | 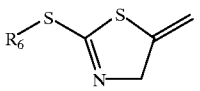 | |
| 1.90a | 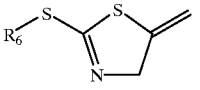 | |
| 1.91a | 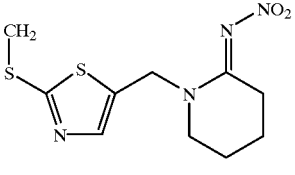 | |
| 1.92a | 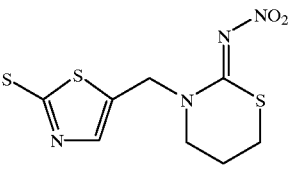 | |
| 1.93a | 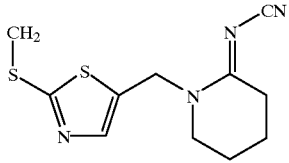 | |
| 1.94a | 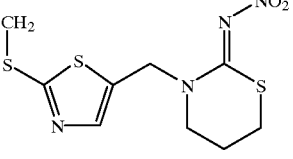 | |
| 1.95a | 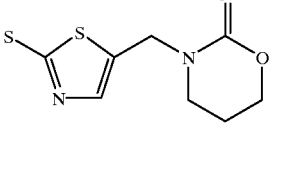 | |
| 1.96a | 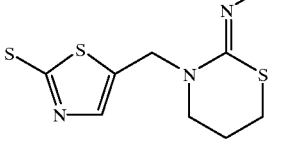 | |
| 1.97a | 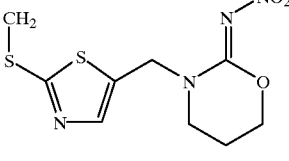 | |
| 1.98a | 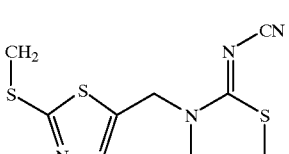 | |
| 1.99a | 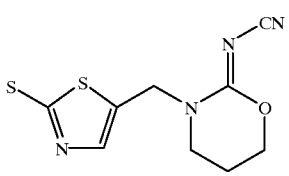 | |
| 1.100a | 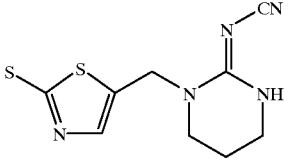 | |
| 1.101a | 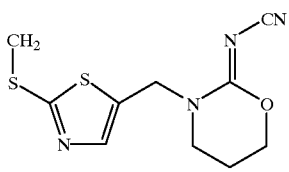 | |

TABLE 2

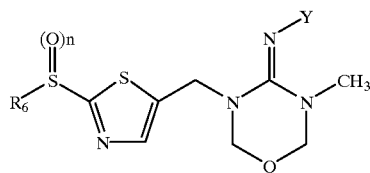

| Compound No. | n | Y | R₆ | Physical data |
| --- | --- | --- | --- | --- |
| 2.1 | 0 | NO₂ | CH₃ | 135–137° |
| 2.2 | 0 | NO₂ | C₂H₅ | |
| 2.3 | 0 | NO₂ | n-C₃H₇ | 67–72° |
| 2.4 | 0 | NO₂ | i-C₃H₇ | |
| 2.5 | 0 | NO₂ | n-C₄H₉ | |
| 2.6 | 0 | NO₂ | t-C₄H₉ | |
| 2.7 | 0 | NO₂ | cyclo-C₃H₅ | |
| 2.8 | 0 | NO₂ | cyclo-C₆H₁₁ | 109–110° |
| 2.9 | 0 | NO₂ | CH₂C₆H₅ | 140–145° (decomp.) |
| 2.10 | 0 | NO₂ | CH₂C₆H₄-4-CH₃ | |
| 2.11 | 0 | NO₂ | CH₂C₆H₄-4-OCH₃ | |
| 2.12 | 0 | NO₂ | CH₂C₆H₄-4-Cl | |
| 2.13 | 0 | NO₂ | CH₂C₆H₄-4-NO₂ | |
| 2.14 | 0 | NO₂ | CH₂-2-furyl | |
| 2.15 | 0 | NO₂ | CH₂-2-thienyl | |
| 2.16 | 0 | NO₂ | C₆H₅ | 147° |
| 2.17 | 0 | NO₂ | C₆H₄-4-CH₃ | 160–162° |
| 2.18 | 0 | NO₂ | C₆H₄-4-OCH₃ | |
| 2.19 | 0 | NO₂ | C₆H₄-4-Cl | |
| 2.20 | 0 | NO₂ | C₆H₄-4-NO₂ | |
| 2.21 | 0 | CN | CH₂SCH₂C≡CC₆H₅ | |
| 2.22 | 0 | NO₂ | CH₂CH=CH₂ | |
| 2.23 | 0 | NO₂ | CH₂C≡CH | |
| 2.24 | 0 | NO₂ | CH₂CH=CHC₆H₅ | |
| 2.25 | 0 | NO₂ | CH₂C≡CC₆H₅ | |
| 2.26 | 0 | NO₂ | CH₂—CH₂—CH₂—CH₂—CH₂—SH | 57–60° |
| 2.27 | 0 | NO₂ | CH₂CO₂C₂H₅ | |
| 2.28 | 0 | NO₂ | CH₂CO₂Na | 130–138° (decomp.) |
| 2.29 | 0 | NO₂ | SCH₃ | |
| 2.30 | 0 | NO₂ | SC₂H₅ | |
| 2.31 | 0 | NO₂ | S-n-C₃H₇ | |
| 2.32 | 0 | NO₂ | S-i-C₃H₇ | |
| 2.33 | 0 | NO₂ | S-n-C₄H₉ | |
| 2.34 | 0 | NO₂ | S-t-C₄H₉ | |
| 2.35 | 0 | NO₂ | S-cyclo-C₃H₅ | |
| 2.36 | 0 | NO₂ | SCH₂C₆H₅ | |
| 2.37 | 0 | NO₂ | SCH₂C₆H₄-4-CH₃ | |
| 2.38 | 0 | NO₂ | SCH₂C₆H₄-4-OCH₃ | |
| 2.39 | 0 | NO₂ | SCH₂C₆H₄-4-Cl | |
| 2.40 | 0 | NO₂ | SCH₂C₆H₄-4-NO₂ | |
| 2.41 | 0 | NO₂ | SCH₂-2-furyl | |
| 2.42 | 0 | NO₂ | SCH₂-2-thienyl | |
| 2.43 | 0 | NO₂ | SC₆H₅ | |
| 2.44 | 0 | NO₂ | SC₆H₄-4-CH₃ | |
| 2.45 | 0 | NO₂ | SC₆H₄-4-OCH₃ | |
| 2.46 | 0 | NO₂ | SC₆H₄-4-Cl | |
| 2.47 | 0 | NO₂ | SC₆H₄-4-NO₂ | |
| 2.48 | 0 | NO₂ | SCH₂CH=CH₂ | |
| 2.49 | 0 | NO₂ | SCH₂C≡CH | |
| 2.50 | 0 | NO₂ | SCH₂CH=CHC₆H₅ | |
| 2.51 | 0 | NO₂ | SCH₂C≡CC₆H₅ | |
| 2.52 | 0 | NO₂ | | |
| 2.53 | 1 | NO₂ | CH₃ | |
| 2.54 | 1 | NO₂ | C₂H₅ | |
| 2.55 | 1 | NO₂ | n-C₃H₇ | |
| 2.56 | 1 | NO₂ | i-C₃H₇ | |

TABLE 2-continued

| Compound No. | n | Y | R$_6$ | Physical data |
|---|---|---|---|---|
| 2.57 | 1 | NO$_2$ | n-C$_4$H$_9$ | |
| 2.58 | 1 | NO$_2$ | t-C$_4$H$_9$ | |
| 2.59 | 1 | NO$_2$ | cyclo-C$_3$H$_5$ | |
| 2.60 | 1 | NO$_2$ | CH$_2$C$_6$H$_5$ | 170–180° |
| 2.61 | 1 | NO$_2$ | CH$_2$C$_6$H$_4$-4-CH$_3$ | |
| 2.62 | 1 | NO$_2$ | CH$_2$C$_6$H$_4$-4-OCH$_3$ | |
| 2.63 | 1 | NO$_2$ | CH$_2$C$_6$H$_4$-4-Cl | |
| 2.64 | 1 | NO$_2$ | CH$_2$C$_6$H$_4$-4-NO$_2$ | |
| 2.65 | 1 | NO$_2$ | CH$_2$-2-furyl | |
| 2.66 | 1 | NO$_2$ | CH$_2$-2-thienyl | |
| 2.67 | 1 | NO$_2$ | C$_6$H$_5$ | |
| 2.68 | 1 | NO$_2$ | C$_6$H$_4$-4-CH$_3$ | |
| 2.69 | 1 | NO$_2$ | C$_6$H$_4$-4-OCH$_3$ | |
| 2.70 | 1 | NO$_2$ | C$_6$H$_4$-4-Cl | |
| 2.71 | 1 | NO$_2$ | C$_6$H$_4$-4-NO$_2$ | |
| 2.72 | 1 | NO$_2$ | CH$_2$CH=CH$_2$ | |
| 2.73 | 1 | NO$_2$ | CH$_2$C≡CH | |
| 2.74 | 1 | NO$_2$ | CH$_2$CH=CHC$_6$H$_5$ | |
| 2.75 | 1 | NO$_2$ | CH$_2$C≡CC$_6$H$_5$ | |
| 2.76 | 2 | NO$_2$ | CH$_3$ | 157° |
| 2.77 | 2 | NO$_2$ | C$_2$H$_5$ | |
| 2.78 | 2 | NO$_2$ | n-C$_3$H$_7$ | resin |
| 2.79 | 2 | NO$_2$ | i-C$_3$H$_7$ | |
| 2.80 | 2 | NO$_2$ | n-C$_4$H$_9$ | |
| 2.81 | 2 | NO$_2$ | t-C$_4$H$_9$ | |
| 2.82 | 2 | NO$_2$ | cyclo-C$_3$H$_5$ | |
| 2.83 | 2 | NO$_2$ | CH$_2$C$_6$H$_5$ | 160–175° |
| 2.84 | 2 | NO$_2$ | CH$_2$C$_6$H$_4$-4-CH$_3$ | |
| 2.85 | 2 | NO$_2$ | CH$_2$C$_6$H$_4$-4-OCH$_3$ | |
| 2.86 | 2 | NO$_2$ | CH$_2$C$_6$H$_4$-4-Cl | |
| 2.87 | 2 | NO$_2$ | CH$_2$C$_6$H$_4$-4-NO$_2$ | |
| 2.88 | 2 | NO$_2$ | CH$_2$-2-furyl | |
| 2.89 | 2 | NO$_2$ | CH$_2$-2-thienyl | |
| 2.90 | 2 | NO$_2$ | C$_6$H$_5$ | 210° |
| 2.91 | 2 | NO$_2$ | C$_6$H$_4$-4-CH$_3$ | |
| 2.92 | 2 | NO$_2$ | C$_6$H$_4$-4-OCH$_3$ | |
| 2.93 | 2 | NO$_2$ | C$_6$H$_4$-4-Cl | |
| 2.94 | 2 | NO$_2$ | C$_6$H$_4$-4-NO$_2$ | |
| 2.95 | 2 | NO$_2$ | CH$_2$CH=CH$_2$ | |
| 2.96 | 2 | NO$_2$ | CH$_2$C≡CH | |
| 2.97 | 2 | NO$_2$ | CH$_2$CH=CHC$_6$H$_5$ | |
| 2.98 | 2 | NO$_2$ | CH$_2$C≡CC$_6$H$_5$ | |
| 2.99 | 0 | NO$_2$ | CH$_2$SCH$_3$ | |
| 2.100 | 0 | NO$_2$ | CH$_2$SC$_2$H$_5$ | |
| 2.101 | 0 | NO$_2$ | CH$_2$S-n-C$_3$H$_7$ | |
| 2.102 | 0 | NO$_2$ | CH$_2$S-i-C$_3$H$_7$ | |
| 2.103 | 0 | NO$_2$ | CH$_2$S-n-C$_4$H$_9$ | |
| 2.104 | 0 | NO$_2$ | CH$_2$S-t-C$_4$H$_9$ | |
| 2.105 | 0 | NO$_2$ | CH$_2$S-cyclo-C$_3$H$_5$ | |
| 2.106 | 0 | NO$_2$ | CH$_2$SCH$_2$C$_6$H$_5$ | |
| 2.107 | 0 | NO$_2$ | CH$_2$SCH$_2$C$_6$H$_4$-4-CH$_3$ | |
| 2.108 | 0 | NO$_2$ | CH$_2$SCH$_2$C$_6$H$_4$-4-OCH$_3$ | |
| 2.109 | 0 | NO$_2$ | CH$_2$SCH$_2$C$_6$H$_4$-4-Cl | |
| 2.110 | 0 | NO$_2$ | CH$_2$SCH$_2$C$_6$H$_4$-4-NO$_2$ | |
| 2.111 | 0 | NO$_2$ | CH$_2$SCH$_2$-2-furyl | |
| 2.112 | 0 | NO$_2$ | CH$_2$SCH$_2$-2-thienyl | |
| 2.113 | 0 | NO$_2$ | CH$_2$SC$_6$H$_5$ | |
| 2.114 | 0 | NO$_2$ | CH$_2$SC$_6$H$_4$-4-CH$_3$ | |
| 2.115 | 0 | NO$_2$ | CH$_2$SC$_6$H$_4$-4-OCH$_3$ | |
| 2.116 | 0 | NO$_2$ | CH$_2$SC$_6$H$_4$-4-Cl | |
| 2.117 | 0 | NO$_2$ | CH$_2$SC$_6$H$_4$-4-NO$_2$ | |
| 2.118 | 0 | NO$_2$ | CH$_2$SCH$_2$CH=CH$_2$ | |
| 2.119 | 0 | NO$_2$ | CH$_2$SCH$_2$C≡CH | |
| 2.120 | 0 | NO$_2$ | CH$_2$SCH$_2$CH=CHC$_6$H$_5$ | |
| 2.121 | 0 | NO$_2$ | CH$_2$SCH$_2$C≡CC$_6$H$_5$ | |

TABLE 2-continued

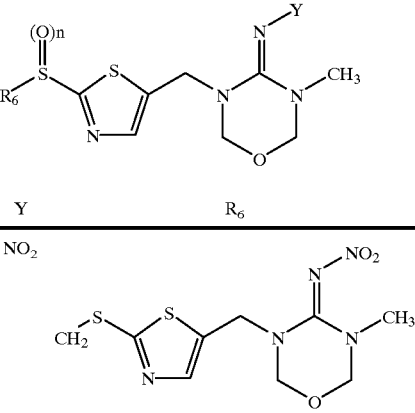

| Compound No. | n | Y | R$_6$ | Physical data |
|---|---|---|---|---|
| 2.122 | 0 | NO$_2$ | | |

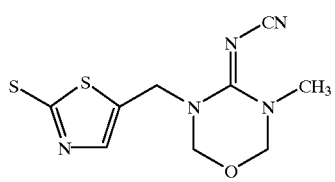

| Compound No. | n | Y | R$_6$ | Physical data |
|---|---|---|---|---|
| 2.123 | 0 | CN | CH$_3$ | |
| 2.124 | 0 | CN | C$_2$H$_5$ | |
| 2.125 | 0 | CN | n-C$_3$H$_7$ | |
| 2.126 | 0 | CN | i-C$_3$H$_7$ | |
| 2.127 | 0 | CN | n-C$_4$H$_9$ | |
| 2.128 | 0 | CN | t-C$_4$H$_9$ | |
| 2.129 | 0 | CN | cyclo-C$_3$H$_5$ | |
| 2.130 | 0 | CN | CH$_2$C$_6$H$_5$ | |
| 2.131 | 0 | CN | CH$_2$C$_6$H$_4$-4-CH$_3$ | |
| 2.132 | 0 | CN | CH$_2$C$_6$H$_4$-4-OCH$_3$ | |
| 2.133 | 0 | CN | CH$_2$C$_6$H$_4$-4-Cl | |
| 2.134 | 0 | CN | CH$_2$C$_6$H$_4$-4-NO$_2$ | |
| 2.135 | 0 | CN | CH$_2$-2-furyl | |
| 2.136 | 0 | CN | CH$_2$-2-thienyl | |
| 2.137 | 0 | CN | C$_6$H$_5$ | |
| 2.138 | 0 | CN | C$_6$H$_4$-4-CH$_3$ | |
| 2.139 | 0 | CN | C$_6$H$_4$-4-OCH$_3$ | |
| 2.140 | 0 | CN | C$_6$H$_4$-4-Cl | |
| 2.141 | 0 | CN | C$_6$H$_4$-4-NO$_2$ | |
| 2.142 | 0 | CN | CH$_2$CH=CH$_2$ | |
| 2.143 | 0 | CN | CH$_2$C≡CH | |
| 2.144 | 0 | CN | CH$_2$CH=CHC$_6$H$_5$ | |
| 2.145 | 0 | CN | CH$_2$C≡CC$_6$H$_5$ | |
| 2.146 | 0 | CN | SCH$_3$ | |
| 2.147 | 0 | CN | SC$_2$H$_5$ | |
| 2.148 | 0 | CN | S-n-C$_3$H$_7$ | |
| 2.149 | 0 | CN | S-i-C$_3$H$_7$ | |
| 2.150 | 0 | CN | S-n-C$_4$H$_9$ | |
| 2.151 | 0 | CN | S-t-C$_4$H$_9$ | |
| 2.152 | 0 | CN | S-cyclo-C$_3$H$_5$ | |
| 2.153 | 0 | CN | SCH$_2$C$_6$H$_5$ | |
| 2.154 | 0 | CN | SCH$_2$C$_6$H$_4$-4-CH$_3$ | |
| 2.155 | 0 | CN | SCH$_2$C$_6$H$_4$-4-OCH$_3$ | |
| 2.156 | 0 | CN | SCH$_2$C$_6$H$_4$-4-Cl | |
| 2.157 | 0 | CN | SCH$_2$C$_6$H$_4$-4-NO$_2$ | |
| 2.158 | 0 | CN | SCH$_2$-2-furyl | |
| 2.159 | 0 | CN | SCH$_2$-2-thienyl | |
| 2.160 | 0 | CN | SC$_6$H$_5$ | |
| 2.161 | 0 | CN | SC$_6$H$_4$-4-CH$_3$ | |
| 2.162 | 0 | CN | SC$_6$H$_4$-4-OCH$_3$ | |
| 2.163 | 0 | CN | SC$_6$H$_4$-4-Cl | |
| 2.164 | 0 | CN | SC$_6$H$_4$-4-NO$_2$ | |
| 2.165 | 0 | CN | SCH$_2$CH=CH$_2$ | |
| 2.166 | 0 | CN | SCH$_2$C≡CH | |
| 2.167 | 0 | CN | SCH$_2$CH=CHC$_6$H$_5$ | |
| 2.168 | 0 | CN | SCH$_2$C≡CC$_6$H$_5$ | |
| 2.169 | 0 | CN | | |
| 2.170 | 1 | CN | CH$_3$ | |

TABLE 2-continued

| Compound No. | n | Y | R₆ | Physical data |
|---|---|---|---|---|
| 2.171 | 1 | CN | $C_2H_5$ | |
| 2.172 | 1 | CN | $n\text{-}C_3H_7$ | |
| 2.173 | 1 | CN | $i\text{-}C_3H_7$ | |
| 2.174 | 1 | CN | $n\text{-}C_4H_9$ | |
| 2.175 | 1 | CN | $t\text{-}C_4H_9$ | |
| 2.176 | 1 | CN | $cyclo\text{-}C_3H_5$ | |
| 2.177 | 1 | CN | $CH_2C_6H_5$ | |
| 2.178 | 1 | CN | $CH_2C_6H_4\text{-}4\text{-}CH_3$ | |
| 2.179 | 1 | CN | $CH_2C_6H_4\text{-}4\text{-}OCH_3$ | |
| 2.180 | 1 | CN | $CH_2C_6H_4\text{-}4\text{-}Cl$ | |
| 2.181 | 1 | CN | $CH_2C_6H_4\text{-}4\text{-}NO_2$ | |
| 2.182 | 1 | CN | $CH_2\text{-}2\text{-}furyl$ | |
| 2.183 | 1 | CN | $CH_2\text{-}2\text{-}thienyl$ | |
| 2.184 | 1 | CN | $C_6H_5$ | |
| 2.185 | 1 | CN | $C_6H_4\text{-}4\text{-}CH_3$ | |
| 2.186 | 1 | CN | $C_6H_4\text{-}4\text{-}OCH_3$ | |
| 2.187 | 1 | CN | $C_6H_4\text{-}4\text{-}Cl$ | |
| 2.188 | 1 | CN | $C_6H_4\text{-}4\text{-}NO_2$ | |
| 2.189 | 1 | CN | $CH_2CH=CH_2$ | |
| 2.190 | 1 | CN | $CH_2C\equiv CH$ | |
| 2.191 | 1 | CN | $CH_2CH=CHC_6H_5$ | |
| 2.192 | 1 | CN | $CH_2C\equiv CC_6H_5$ | |
| 2.193 | 2 | CN | $CH_3$ | |
| 2.194 | 2 | CN | $C_2H_5$ | |
| 2.195 | 2 | CN | $n\text{-}C_3H_7$ | |
| 2.196 | 2 | CN | $i\text{-}C_3H_7$ | |
| 2.197 | 2 | CN | $n\text{-}C_4H_9$ | |
| 2.198 | 2 | CN | $t\text{-}C_4H_9$ | |
| 2.199 | 2 | CN | $cyclo\text{-}C_3H_5$ | |
| 2.200 | 2 | CN | $CH_2C_6H_5$ | |
| 2.201 | 2 | CN | $CH_2C_6H_4\text{-}4\text{-}CH_3$ | |
| 2.202 | 2 | CN | $CH_2C_6H_4\text{-}4\text{-}OCH_3$ | |
| 2.203 | 2 | CN | $CH_2C_6H_4\text{-}4\text{-}Cl$ | |
| 2.204 | 2 | CN | $CH_2C_6H_4\text{-}4\text{-}NO_2$ | |
| 2.205 | 2 | CN | $CH_2\text{-}2\text{-}furyl$ | |
| 2.206 | 2 | CN | $CH_2\text{-}2\text{-}thienyl$ | |
| 2.207 | 2 | CN | $C_6H_5$ | |
| 2.208 | 2 | CN | $C_6H_4\text{-}4\text{-}CH_3$ | |
| 2.209 | 2 | CN | $C_6H_4\text{-}4\text{-}OCH_3$ | |
| 2.210 | 2 | CN | $C_6H_4\text{-}4\text{-}Cl$ | |
| 2.211 | 2 | CN | $C_6H_4\text{-}4\text{-}NO_2$ | |
| 2.212 | 2 | CN | $CH_2CH=CH_2$ | |
| 2.213 | 2 | CN | $CH_2C\equiv CH$ | |
| 2.214 | 2 | CN | $CH_2CH=CHC_6H_5$ | |
| 2.215 | 2 | CN | $CH_2C\equiv CC_6H_5$ | |
| 2.216 | 0 | CN | $CH_2SCH_3$ | |
| 2.217 | 0 | CN | $CH_2SC_2H_5$ | |
| 2.218 | 0 | CN | $CH_2S\text{-}n\text{-}C_3H_7$ | |
| 2.219 | 0 | CN | $CH_2S\text{-}i\text{-}C_3H_7$ | |
| 2.220 | 0 | CN | $CH_2S\text{-}n\text{-}C_4H_9$ | |
| 2.221 | 0 | CN | $CH_2S\text{-}t\text{-}C_4H_9$ | |
| 2.222 | 0 | CN | $CH_2S\text{-}cyclo\text{-}C_3H_5$ | |
| 2.223 | 0 | CN | $CH_2SCH_2C_6H_5$ | |
| 2.224 | 0 | CN | $CH_2SCH_2C_6H_4\text{-}4\text{-}CH_3$ | |
| 2.225 | 0 | CN | $CH_2SCH_2C_6H_4\text{-}4\text{-}OCH_3$ | |
| 2.226 | 0 | CN | $CH_2SCH_2C_6H_4\text{-}4\text{-}Cl$ | |
| 2.227 | 0 | CN | $CH_2SCH_2C_6H_4\text{-}4\text{-}NO_2$ | |
| 2.228 | 0 | CN | $CH_2SCH_2\text{-}2\text{-}furyl$ | |
| 2.229 | 0 | CN | $CH_2SCH_2\text{-}2\text{-}thienyl$ | |
| 2.230 | 0 | CN | $CH_2SC_6H_5$ | |
| 2.231 | 0 | CN | $CH_2SC_6H_4\text{-}4\text{-}CH_3$ | |
| 2.232 | 0 | CN | $CH_2SC_6H_4\text{-}4\text{-}OCH_3$ | |
| 2.233 | 0 | CN | $CH_2SC_6H_4\text{-}4\text{-}Cl$ | |
| 2.234 | 0 | CN | $CH_2SC_6H_4\text{-}4\text{-}NO_2$ | |
| 2.235 | 0 | CN | $CH_2SCH_2CH=CH_2$ | |
| 2.236 | 0 | CN | $CH_2SCH_2C\equiv CH$ | |
| 2.237 | 0 | CN | $CH_2SCH_2CH=CHC_6H_5$ | |

TABLE 2-continued

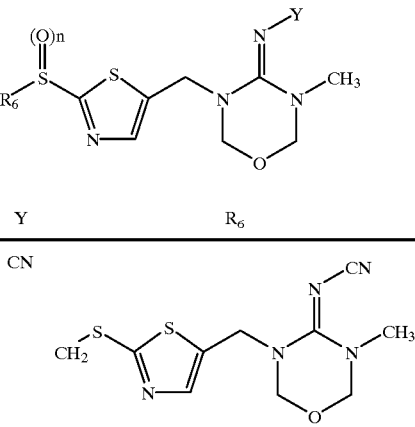

| Compound No. | n | Y | R$_6$ | Physical data |
|---|---|---|---|---|
| 2.238 | 0 | CN | | |

[Structure shown for compound 2.238]

TABLE 3

| Compound No. | n | Y | R$_6$ | Physical data |
|---|---|---|---|---|
| 3.1 | 0 | NO$_2$ | CH$_3$ | |
| 3.2 | 0 | NO$_2$ | C$_2$H$_5$ | |
| 3.3 | 0 | NO$_2$ | n-C$_3$H$_7$ | |
| 3.4 | 0 | NO$_2$ | i-C$_3$H$_7$ | |
| 3.5 | 0 | NO$_2$ | n-C$_4$H$_9$ | |
| 3.6 | 0 | NO$_2$ | t-C$_4$H$_9$ | |
| 3.7 | 0 | NO$_2$ | cyclo-C$_3$H$_5$ | |
| 3.8 | 0 | NO$_2$ | CH$_2$C$_6$H$_5$ | |
| 3.9 | 0 | NO$_2$ | CH$_2$C$_6$H$_4$-4-CH$_3$ | |
| 3.10 | 0 | NO$_2$ | CH$_2$C$_6$H$_4$-4-OCH$_3$ | |
| 3.11 | 0 | NO$_2$ | CH$_2$C$_6$H$_4$-4-Cl | |
| 3.12 | 0 | NO$_2$ | CH$_2$C$_6$H$_4$-4-NO$_2$ | |
| 3.13 | 0 | NO$_2$ | CH$_2$-2-furyl | |
| 3.14 | 0 | NO$_2$ | CH$_2$-2-thienyl | |
| 3.15 | 0 | NO$_2$ | C$_6$H$_5$ | |
| 3.16 | 0 | NO$_2$ | C$_6$H$_4$-4-CH$_3$ | |
| 3.17 | 0 | NO$_2$ | C$_6$H$_4$-4-OCH$_3$ | |
| 3.18 | 0 | NO$_2$ | C$_6$H$_4$-4-Cl | |
| 3.19 | 0 | NO$_2$ | C$_6$H$_4$-4-NO$_2$ | |
| 3.20 | 0 | NO$_2$ | CH$_2$CH=CH$_2$ | |
| 3.21 | 0 | NO$_2$ | CH$_2$C≡CH | |
| 3.22 | 0 | NO$_2$ | CH$_2$CH=CHC$_6$H$_5$ | |
| 3.23 | 0 | NO$_2$ | CH$_2$C≡CC$_6$H$_5$ | |
| 3.24 | 0 | NO$_2$ | SCH$_3$ | |
| 3.25 | 0 | NO$_2$ | SC$_2$H$_5$ | |
| 3.26 | 0 | NO$_2$ | S-n-C$_3$H$_7$ | |
| 3.27 | 0 | NO$_2$ | S-i-C$_3$H$_7$ | |
| 3.28 | 0 | NO$_2$ | S-n-C$_4$H$_9$ | |
| 3.29 | 0 | NO$_2$ | S-t-C$_4$H$_9$ | |
| 3.30 | 0 | NO$_2$ | S-cyclo-C$_3$H$_5$ | |
| 3.31 | 0 | NO$_2$ | SCH$_2$C$_6$H$_5$ | |
| 3.32 | 0 | NO$_2$ | SCH$_2$C$_6$H$_4$-4-CH$_3$ | |
| 3.33 | 0 | NO$_2$ | SCH$_2$C$_6$H$_4$-4-OCH$_3$ | |
| 3.34 | 0 | NO$_2$ | SCH$_2$C$_6$H$_4$-4-Cl | |
| 3.35 | 0 | NO$_2$ | SCH$_2$C$_6$H$_4$-4-NO$_2$ | |
| 3.36 | 0 | NO$_2$ | SCH$_2$-2-furyl | |
| 3.37 | 0 | NO$_2$ | SCH$_2$-2-thienyl | |
| 3.38 | 0 | NO$_2$ | SC$_6$H$_5$ | |
| 3.39 | 0 | NO$_2$ | SC$_6$H$_4$-4-CH$_3$ | |
| 3.40 | 0 | NO$_2$ | SC$_6$H$_4$-4-OCH$_3$ | |
| 3.41 | 0 | NO$_2$ | SC$_6$H$_4$-4-Cl | |
| 3.42 | 0 | NO$_2$ | SC$_6$H$_4$-4-NO$_2$ | |

TABLE 3-continued

Structure: thiazole ring with $R_6-S(O)_n-$ substituent at 2-position and $-CH_2-$ linker at 5-position connecting to a tetrahydropyrimidine with $=N-Y$ and N-$CH_3$ groups.

| Compound No. | n | Y | $R_6$ | Physical data |
|---|---|---|---|---|
| 3.43 | 0 | $NO_2$ | $SCH_2CH=CH_2$ | |
| 3.44 | 0 | $NO_2$ | $SCH_2C\equiv CH$ | |
| 3.45 | 0 | $NO_2$ | $SCH_2CH=CHC_6H_5$ | |
| 3.46 | 0 | $NO_2$ | $SCH_2C\equiv CC_6H_5$ | |
| 3.47 | 0 | $NO_2$ | (structure shown) | |
| 3.48 | 1 | $NO_2$ | $CH_3$ | |
| 3.49 | 1 | $NO_2$ | $C_2H_5$ | |
| 3.50 | 1 | $NO_2$ | n-$C_3H_7$ | |
| 3.51 | 1 | $NO_2$ | i-$C_3H_7$ | |
| 3.52 | 1 | $NO_2$ | n-$C_4H_9$ | |
| 3.53 | 1 | $NO_2$ | t-$C_4H_9$ | |
| 3.54 | 1 | $NO_2$ | cyclo-$C_3H_5$ | |
| 3.55 | 1 | $NO_2$ | $CH_2C_6H_5$ | |
| 3.56 | 1 | $NO_2$ | $CH_2C_6H_4$-4-$CH_3$ | |
| 3.57 | 1 | $NO_2$ | $CH_2C_6H_4$-4-$OCH_3$ | |
| 3.58 | 1 | $NO_2$ | $CH_2C_6H_4$-4-Cl | |
| 3.59 | 1 | $NO_2$ | $CH_2C_6H_4$-4-$NO_2$ | |
| 3.60 | 1 | $NO_2$ | $CH_2$-2-furyl | |
| 3.61 | 1 | $NO_2$ | $CH_2$-2-thienyl | |
| 3.62 | 1 | $NO_2$ | $C_6H_5$ | |
| 3.63 | 1 | $NO_2$ | $C_6H_4$-4-$CH_3$ | |
| 3.64 | 1 | $NO_2$ | $C_6H_4$-4-$OCH_3$ | |
| 3.65 | 1 | $NO_2$ | $C_6H_4$-4-Cl | |
| 3.66 | 1 | $NO_2$ | $C_6H_4$-4-$NO_2$ | |
| 3.67 | 1 | $NO_2$ | $CH_2CH=CH_2$ | |
| 3.68 | 1 | $NO_2$ | $CH_2C\equiv CH$ | |
| 3.69 | 1 | $NO_2$ | $CH_2CH=CHC_6H_5$ | |
| 3.70 | 1 | $NO_2$ | $CH_2C\equiv CC_6H_5$ | |
| 3.71 | 2 | $NO_2$ | $CH_3$ | |
| 3.72 | 2 | $NO_2$ | $C_2H_5$ | |
| 3.73 | 2 | $NO_2$ | n-$C_3H_7$ | |
| 3.74 | 2 | $NO_2$ | i-$C_3H_7$ | |
| 3.75 | 2 | $NO_2$ | n-$C_4H_9$ | |
| 3.76 | 2 | $NO_2$ | t-$C_4H_9$ | |
| 3.77 | 2 | $NO_2$ | cyclo-$C_3H_5$ | |
| 3.78 | 2 | $NO_2$ | $CH_2C_6H_5$ | |
| 3.79 | 2 | $NO_2$ | $CH_2C_6H_4$-4-$CH_3$ | |
| 3.80 | 2 | $NO_2$ | $CH_2C_6H_4$-4-$OCH_3$ | |
| 3.81 | 2 | $NO_2$ | $CH_2C_6H_4$-4-Cl | |
| 3.82 | 2 | $NO_2$ | $CH_2C_6H_4$-4-$NO_2$ | |
| 3.83 | 2 | $NO_2$ | $CH_2$-2-furyl | |
| 3.84 | 2 | $NO_2$ | $CH_2$-2-thienyl | |
| 3.85 | 2 | $NO_2$ | $C_6H_5$ | |
| 3.86 | 2 | $NO_2$ | $C_6H_4$-4-$CH_3$ | |
| 3.87 | 2 | $NO_2$ | $C_6H_4$-4-$OCH_3$ | |
| 3.88 | 2 | $NO_2$ | $C_6H_4$-4-Cl | |
| 3.89 | 2 | $NO_2$ | $C_6H_4$-4-$NO_2$ | |
| 3.90 | 2 | $NO_2$ | $CH_2CH=CH_2$ | |
| 3.91 | 2 | $NO_2$ | $CH_2C\equiv CH$ | |
| 3.92 | 2 | $NO_2$ | $CH_2CH=CHC_6H_5$ | |
| 3.93 | 2 | $NO_2$ | $CH_2C\equiv CC_6H_5$ | |
| 3.94 | 0 | $NO_2$ | $CH_2SCH_3$ | |
| 3.95 | 0 | $NO_2$ | $CH_2SC_2H_5$ | |
| 3.96 | 0 | $NO_2$ | $CH_2S$-n-$C_3H_7$ | |
| 3.97 | 0 | $NO_2$ | $CH_2S$-i-$C_3H_7$ | |
| 3.98 | 0 | $NO_2$ | $CH_2S$-n-$C_4H_9$ | |
| 3.99 | 0 | $NO_2$ | $CH_2S$-t-$C_4H_9$ | |
| 3.100 | 0 | $NO_2$ | $CH_2S$-cyclo-$C_3H_5$ | |

TABLE 3-continued

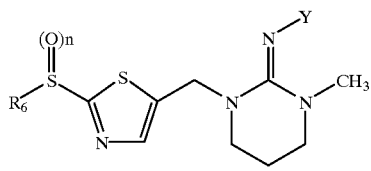

| Compound No. | n | Y | $R_6$ | Physical data |
|---|---|---|---|---|
| 3.101 | 0 | $NO_2$ | $CH_2SCH_2C_6H_5$ | |
| 3.102 | 0 | $NO_2$ | $CH_2SCH_2C_6H_4$-4-$CH_3$ | |
| 3.103 | 0 | $NO_2$ | $CH_2SCH_2C_6H_4$-4-$OCH_3$ | |
| 3.104 | 0 | $NO_2$ | $CH_2SCH_2C_6H_4$-4-Cl | |
| 3.105 | 0 | $NO_2$ | $CH_2SCH_2C_6H_4$-4-$NO_2$ | |
| 3.106 | 0 | $NO_2$ | $CH_2SCH_2$-2-furyl | |
| 3.107 | 0 | $NO_2$ | $CH_2SCH_2$-2-thienyl | |
| 3.108 | 0 | $NO_2$ | $CH_2SC_6H_5$ | |
| 3.109 | 0 | $NO_2$ | $CH_2SC_6H_4$-4-$CH_3$ | |
| 3.110 | 0 | $NO_2$ | $CH_2SC_6H_4$-4-$OCH_3$ | |
| 3.111 | 0 | $NO_2$ | $CH_2SC_6H_4$-4-Cl | |
| 3.112 | 0 | $NO_2$ | $CH_2SC_6H_4$-4-$NO_2$ | |
| 3.113 | 0 | $NO_2$ | $CH_2SCH_2CH=CH_2$ | |
| 3.114 | 0 | $NO_2$ | $CH_2SCH_2C\equiv CH$ | |
| 3.115 | 0 | $NO_2$ | $CH_2SCH_2CH=CHC_6H_5$ | |
| 3.116 | 0 | $NO_2$ | $CH_2SCH_2C\equiv CC_6H_5$ | |
| 3.117 | 0 | $NO_2$ | | |

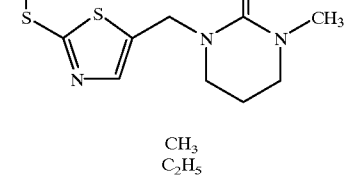

| Compound No. | n | Y | $R_6$ | Physical data |
|---|---|---|---|---|
| 3.118 | 0 | CN | $CH_3$ | |
| 3.119 | 0 | CN | $C_2H_5$ | |
| 3.120 | 0 | CN | n-$C_3H_7$ | |
| 3.121 | 0 | CN | i-$C_3H_7$ | |
| 3.122 | 0 | CN | n-$C_4H_9$ | |
| 3.123 | 0 | CN | t-$C_4H_9$ | |
| 3.124 | 0 | CN | cyclo-$C_3H_5$ | |
| 3.125 | 0 | CN | $CH_2C_6H_5$ | |
| 3.126 | 0 | CN | $CH_2C_6H_4$-4-$CH_3$ | |
| 3.127 | 0 | CN | $CH_2C_6H_4$-4-$OCH_3$ | |
| 3.128 | 0 | CN | $CH_2C_6H_4$-4-Cl | |
| 3.129 | 0 | CN | $CH_2C_6H_4$-4-$NO_2$ | |
| 3.130 | 0 | CN | $CH_2$-2-furyl | |
| 3.131 | 0 | CN | $CH_2$-2-thienyl | |
| 3.132 | 0 | CN | $C_6H_5$ | |
| 3.133 | 0 | CN | $C_6H_4$-4-$CH_3$ | |
| 3.134 | 0 | CN | $C_6H_4$-4-$OCH_3$ | |
| 3.135 | 0 | CN | $C_6H_4$-4-Cl | |
| 3.136 | 0 | CN | $C_6H_4$-4-$NO_2$ | |
| 3.137 | 0 | CN | $CH_2CH=CH_2$ | |
| 3.138 | 0 | CN | $CH_2C\equiv CH$ | |
| 3.139 | 0 | CN | $CH_2CH=CHC_6H_5$ | |
| 3.140 | 0 | CN | $CH_2C\equiv CC_6H_5$ | |
| 3.141 | 0 | CN | $SCH_3$ | |
| 3.142 | 0 | CN | $SC_2H_5$ | |
| 3.143 | 0 | CN | S-n-$C_3H_7$ | |
| 3.144 | 0 | CN | S-i-$C_3H_7$ | |
| 3.145 | 0 | CN | S-n-$C_4H_9$ | |
| 3.146 | 0 | CN | S-t-$C_4H_9$ | |
| 3.147 | 0 | CN | S-cyclo-$C_3H_5$ | |
| 3.148 | 0 | CN | $SCH_2C_6H_5$ | |
| 3.149 | 0 | CN | $SCH_2C_6H_4$-4-$CH_3$ | |
| 3.150 | 0 | CN | $SCH_2C_6H_4$-4-$OCH_3$ | |
| 3.151 | 0 | CN | $SCH_2C_6H_4$-4-Cl | |
| 3.152 | 0 | CN | $SCH_2C_6H_4$-4-$NO_2$ | |
| 3.153 | 0 | CN | $SCH_2$-2-furyl | |
| 3.154 | 0 | CN | $SCH_2$-2-thienyl | |
| 3.155 | 0 | CN | $SC_6H_5$ | |
| 3.156 | 0 | CN | $SC_6H_4$-4-$CH_3$ | |
| 3.157 | 0 | CN | $SC_6H_4$-4-$OCH_3$ | |
| 3.158 | 0 | CN | $SC_6H_4$-4-Cl | |

TABLE 3-continued

| Compound No. | n | Y | R$_6$ | Physical data |
|---|---|---|---|---|
| 3.159 | 0 | CN | SC$_6$H$_4$-4-NO$_2$ | |
| 3.160 | 0 | CN | SCH$_2$CH=CH$_2$ | |
| 3.161 | 0 | CN | SCH$_2$C≡CH | |
| 3.162 | 0 | CN | SCH$_2$CH=CHC$_6$H$_5$ | |
| 3.163 | 0 | CN | SCH$_2$C≡CC$_6$H$_5$ | |
| 3.164 | 0 | CN | | |
| 3.165 | 1 | CN | CH$_3$ | |
| 3.166 | 1 | CN | C$_2$H$_5$ | |
| 3.167 | 1 | CN | n-C$_3$H$_7$ | |
| 3.168 | 1 | CN | i-C$_3$H$_7$ | |
| 3.169 | 1 | CN | n-C$_4$H$_9$ | |
| 3.170 | 1 | CN | t-C$_4$H$_9$ | |
| 3.171 | 1 | CN | cyclo-C$_3$H$_5$ | |
| 3.172 | 1 | CN | CH$_2$C$_6$H$_5$ | |
| 3.173 | 1 | CN | CH$_2$C$_6$H$_4$-4-CH$_3$ | |
| 3.174 | 1 | CN | CH$_2$C$_6$H$_4$-4-OCH$_3$ | |
| 3.175 | 1 | CN | CH$_2$C$_6$H$_4$-4-Cl | |
| 3.176 | 1 | CN | CH$_2$C$_6$H$_4$-4-NO$_2$ | |
| 3.177 | 1 | CN | CH$_2$-2-furyl | |
| 3.178 | 1 | CN | CH$_2$-2-thienyl | |
| 3.179 | 1 | CN | C$_6$H$_5$ | |
| 3.180 | 1 | CN | C$_6$H$_4$-4-CH$_3$ | |
| 3.181 | 1 | CN | C$_6$H$_4$-4-OCH$_3$ | |
| 3.182 | 1 | CN | C$_6$H$_4$-4-Cl | |
| 3.183 | 1 | CN | C$_6$H$_4$-4-NO$_2$ | |
| 3.184 | 1 | CN | CH$_2$CH=CH$_2$ | |
| 3.185 | 1 | CN | CH$_2$C≡CH | |
| 3.186 | 1 | CN | CH$_2$CH=CHC$_6$H$_5$ | |
| 3.187 | 1 | CN | CH$_2$C≡CC$_6$H$_5$ | |
| 3.188 | 2 | CN | CH$_3$ | |
| 3.189 | 2 | CN | C$_2$H$_5$ | |
| 3.190 | 2 | CN | n-C$_3$H$_7$ | |
| 3.191 | 2 | CN | i-C$_3$H$_7$ | |
| 3.192 | 2 | CN | n-C$_4$H$_9$ | |
| 3.193 | 2 | CN | t-C$_4$H$_9$ | |
| 3.194 | 2 | CN | cyclo-C$_3$H$_5$ | |
| 3.195 | 2 | CN | CH$_2$C$_6$H$_5$ | |
| 3.196 | 2 | CN | CH$_2$C$_6$H$_4$-4-CH$_3$ | |
| 3.197 | 2 | CN | CH$_2$C$_6$H$_4$-4-OCH$_3$ | |
| 3.198 | 2 | CN | CH$_2$C$_6$H$_4$-4-Cl | |
| 3.199 | 2 | CN | CH$_2$C$_6$H$_4$-4-NO$_2$ | |
| 3.200 | 2 | CN | CH$_2$-2-furyl | |
| 3.201 | 2 | CN | CH$_2$-2-thienyl | |
| 3.202 | 2 | CN | C$_6$H$_5$ | |
| 3.203 | 2 | CN | C$_6$H$_4$-4-CH$_3$ | |
| 3.204 | 2 | CN | C$_6$H$_4$-4-OCH$_3$ | |
| 3.205 | 2 | CN | C$_6$H$_4$-4-Cl | |
| 3.206 | 2 | CN | C$_6$H$_4$-4-NO$_2$ | |
| 3.207 | 2 | CN | CH$_2$CH=CH$_2$ | |
| 3.208 | 2 | CN | CH$_2$C≡CH | |
| 3.209 | 2 | CN | CH$_2$CH=CHC$_6$H$_5$ | |
| 3.210 | 2 | CN | CH$_2$C≡CC$_6$H$_5$ | |
| 3.211 | 0 | CN | CH$_2$SCH$_3$ | |
| 3.212 | 0 | CN | CH$_2$SC$_2$H$_5$ | |
| 3.213 | 0 | CN | CH$_2$S-n-C$_3$H$_7$ | |
| 3.214 | 0 | CN | CH$_2$S-i-C$_3$H$_7$ | |
| 3.215 | 0 | CN | CH$_2$S-n-C$_4$H$_9$ | |
| 3.216 | 0 | CN | CH$_2$S-t-C$_4$H$_9$ | |

TABLE 3-continued

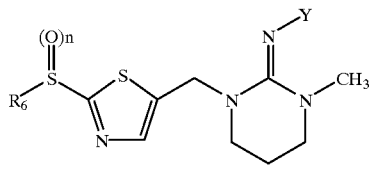

| Compound No. | n | Y | R6 | Physical data |
|---|---|---|---|---|
| 3.217 | 0 | CN | $CH_2S$-cyclo-$C_3H_5$ | |
| 3.218 | 0 | CN | $CH_2SCH_2C_6H_5$ | |
| 3.219 | 0 | CN | $CH_2SCH_2C_6H_4$-4-$CH_3$ | |
| 3.220 | 0 | CN | $CH_2SCH_2C_6H_4$-4-$OCH_3$ | |
| 3.221 | 0 | CN | $CH_2SCH_2C_6H_4$-4-Cl | |
| 3.222 | 0 | CN | $CH_2SCH_2C_6H_4$-4-$NO_2$ | |
| 3.223 | 0 | CN | $CH_2SCH_2$-2-furyl | |
| 3.224 | 0 | CN | $CH_2SCH_2$-2-thienyl | |
| 3.225 | 0 | CN | $CH_2SC_6H_5$ | |
| 3.226 | 0 | CN | $CH_2SC_6H_4$-4-$CH_3$ | |
| 3.227 | 0 | CN | $CH_2SC_6H_4$-4-$OCH_3$ | |
| 3.228 | 0 | CN | $CH_2SC_6H_4$-4-Cl | |
| 3.229 | 0 | CN | $CH_2SC_6H_4$-4-$NO_2$ | |
| 3.230 | 0 | CN | $CH_2SCH_2CH=CH_2$ | |
| 3.231 | 0 | CN | $CH_2SCH_2C\equiv CH$ | |
| 3.232 | 0 | CN | $CH_2SCH_2CH=CHC_6H_5$ | |
| 3.233 | 0 | CN | $CH_2SCH_2\equiv CC_6H_5$ | |
| 3.234 | 0 | CN | | |

TABLE 4

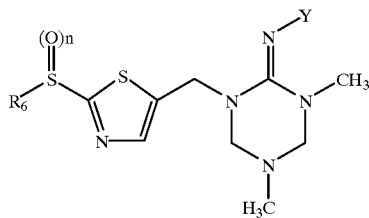

| Compound No. | n | Y | R6 | Physical data |
|---|---|---|---|---|
| 4.1 | 0 | $NO_2$ | $CH_3$ | |
| 4.2 | 0 | $NO_2$ | $C_2H_5$ | |
| 4.3 | 0 | $NO_2$ | n-$C_3H_7$ | |
| 4.4 | 0 | $NO_2$ | i-$C_3H_7$ | |
| 4.5 | 0 | $NO_2$ | n-$C_4H_9$ | |
| 4.6 | 0 | $NO_2$ | t-$C_4H_9$ | |
| 4.7 | 0 | $NO_2$ | cyclo-$C_3H_5$ | |
| 4.8 | 0 | $NO_2$ | $CH_2C_6H_5$ | |
| 4.9 | 0 | $NO_2$ | $CH_2C_6H_4$-4-$CH_3$ | |
| 4.10 | 0 | $NO_2$ | $CH_2C_6H_4$-4-$OCH_3$ | |
| 4.11 | 0 | $NO_2$ | $CH_2C_6H_4$-4-Cl | |
| 4.12 | 0 | $NO_2$ | $CH_2C_6H_4$-4-$NO_2$ | |
| 4.13 | 0 | $NO_2$ | $CH_2$-2-furyl | |
| 4.14 | 0 | $NO_2$ | $CH_2$-2-thienyl | |
| 4.15 | 0 | $NO_2$ | $C_6H_5$ | |
| 4.16 | 0 | $NO_2$ | $C_6H_4$-4-$CH_3$ | |
| 4.17 | 0 | $NO_2$ | $C_6H_4$-4-$OCH_3$ | |
| 4.18 | 0 | $NO_2$ | $C_6H_4$-4-Cl | |
| 4.19 | 0 | $NO_2$ | $C_6H_4$-4-$NO_2$ | |
| 4.20 | 0 | $NO_2$ | $CH_2CH=CH_2$ | |
| 4.21 | 0 | $NO_2$ | $CH_2C\equiv CH$ | |
| 4.22 | 0 | $NO_2$ | $CH_2CH=CHC_6H_5$ | |

TABLE 4-continued

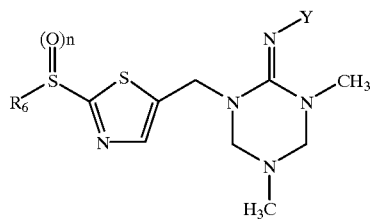

| Compound No. | n | Y | R$_6$ | Physical data |
|---|---|---|---|---|
| 4.23 | 0 | NO$_2$ | CH$_2$C≡C$_6$H$_5$ | |
| 4.24 | 0 | NO$_2$ | SCH$_3$ | |
| 4.25 | 0 | NO$_2$ | SC$_2$H$_5$ | |
| 4.26 | 0 | NO$_2$ | S-n-C$_3$H$_7$ | |
| 4.27 | 0 | NO$_2$ | S-i-C$_3$H$_7$ | |
| 4.28 | 0 | NO$_2$ | S-n-C$_4$H$_9$ | |
| 4.29 | 0 | NO$_2$ | S-t-C$_4$H$_9$ | |
| 4.30 | 0 | NO$_2$ | S-cyclo-C$_3$H$_5$ | |
| 4.31 | 0 | NO$_2$ | SCH$_2$C$_6$H$_5$ | |
| 4.32 | 0 | NO$_2$ | SCH$_2$C$_6$H$_4$-4-CH$_3$ | |
| 4.33 | 0 | NO$_2$ | SCH$_2$C$_6$H$_4$-4-OCH$_3$ | |
| 4.34 | 0 | NO$_2$ | SCH$_2$C$_6$H$_4$-4-Cl | |
| 4.35 | 0 | NO$_2$ | SCH$_2$C$_6$H$_4$-4-NO$_2$ | |
| 4.36 | 0 | NO$_2$ | SCH$_2$-2-furyl | |
| 4.37 | 0 | NO$_2$ | SCH$_2$-2-thienyl | |
| 4.38 | 0 | NO$_2$ | SC$_6$H$_5$ | |
| 4.39 | 0 | NO$_2$ | SC$_6$H$_4$-4-CH$_3$ | |
| 4.40 | 0 | NO$_2$ | SC$_6$H$_4$-4-OCH$_3$ | |
| 4.41 | 0 | NO$_2$ | SC$_6$H$_4$-4-Cl | |
| 4.42 | 0 | NO$_2$ | SC$_6$H$_4$-4-NO$_2$ | |
| 4.43 | 0 | NO$_2$ | SCH$_2$CH=CH$_2$ | |
| 4.44 | 0 | NO$_2$ | SCH$_2$≡CH | |
| 4.45 | 0 | NO$_2$ | SCH$_2$CH=CHC$_6$H$_5$ | |
| 4.46 | 0 | NO$_2$ | SCH$_2$≡CC$_6$H$_5$ | |
| 4.47 | 0 | NO$_2$ | | |
| 4.48 | 1 | NO$_2$ | CH$_3$ | |
| 4.49 | 1 | NO$_2$ | C$_2$H$_5$ | |
| 4.50 | 1 | NO$_2$ | n-C$_3$H$_7$ | |
| 4.51 | 1 | NO$_2$ | i-C$_3$H$_7$ | |
| 4.52 | 1 | NO$_2$ | n-C$_4$H$_9$ | |
| 4.53 | 1 | NO$_2$ | t-C$_4$H$_9$ | |
| 4.54 | 1 | NO$_2$ | cyclo-C$_3$H$_5$ | |
| 4.55 | 1 | NO$_2$ | CH$_2$C$_6$H$_5$ | |
| 4.56 | 1 | NO$_2$ | CH$_2$C$_6$H$_4$-4-CH$_3$ | |
| 4.57 | 1 | NO$_2$ | CH$_2$C$_6$H$_4$-4-OCH$_3$ | |
| 4.58 | 1 | NO$_2$ | CH$_2$C$_6$H$_4$-4-Cl | |
| 4.59 | 1 | NO$_2$ | CH$_2$C$_6$H$_4$-4-NO$_2$ | |
| 4.60 | 1 | NO$_2$ | CH$_2$-2-furyl | |
| 4.61 | 1 | NO$_2$ | CH$_2$-2-thienyl | |
| 4.62 | 1 | NO$_2$ | C$_6$H$_5$ | |
| 4.63 | 1 | NO$_2$ | C$_6$H$_4$-4-CH$_3$ | |
| 4.64 | 1 | NO$_2$ | C$_6$H$_4$-4-OCH$_3$ | |
| 4.65 | 1 | NO$_2$ | C$_6$H$_4$-4-Cl | |
| 4.66 | 1 | NO$_2$ | C$_6$H$_4$-4-NO$_2$ | |
| 4.67 | 1 | NO$_2$ | CH$_2$CH=CH$_2$ | |
| 4.68 | 1 | NO$_2$ | CH$_2$C≡CH | |
| 4.69 | 1 | NO$_2$ | CH$_2$CH=CHC$_6$H$_5$ | |
| 4.70 | 1 | NO$_2$ | CH$_2$C≡CC$_6$H$_5$ | |
| 4.71 | 2 | NO$_2$ | CH$_3$ | |
| 4.72 | 2 | NO$_2$ | C$_2$H$_5$ | |
| 4.73 | 2 | NO$_2$ | n-C$_3$H$_7$ | |
| 4.74 | 2 | NO$_2$ | i-C$_3$H$_7$ | |
| 4.75 | 2 | NO$_2$ | n-C$_4$H$_9$ | |

TABLE 4-continued

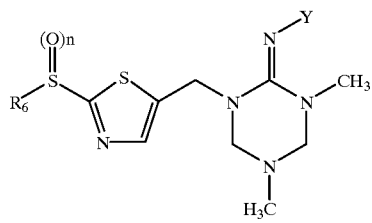

| Compound No. | n | Y | R$_6$ | Physical data |
|---|---|---|---|---|
| 4.76 | 2 | NO$_2$ | t-C$_4$H$_9$ | |
| 4.77 | 2 | NO$_2$ | cyclo-C$_3$H$_5$ | |
| 4.78 | 2 | NO$_2$ | CH$_2$C$_6$H$_5$ | |
| 4.79 | 2 | NO$_2$ | CH$_2$C$_6$H$_4$-4-CH$_3$ | |
| 4.80 | 2 | NO$_2$ | CH$_2$C$_6$H$_4$-4-OCH$_3$ | |
| 4.81 | 2 | NO$_2$ | CH$_2$C$_6$H$_4$-4-Cl | |
| 4.82 | 2 | NO$_2$ | CH$_2$C$_6$H$_4$-4-NO$_2$ | |
| 4.83 | 2 | NO$_2$ | CH$_2$-2-furyl | |
| 4.84 | 2 | NO$_2$ | CH$_2$-2-thienyl | |
| 4.85 | 2 | NO$_2$ | C$_6$H$_5$ | |
| 4.86 | 2 | NO$_2$ | C$_6$H$_4$-4-CH$_3$ | |
| 4.87 | 2 | NO$_2$ | C$_6$H$_4$-4-OCH$_3$ | |
| 4.88 | 2 | NO$_2$ | C$_6$H$_4$-4-Cl | |
| 4.89 | 2 | NO$_2$ | C$_6$H$_4$-4-NO$_2$ | |
| 4.90 | 2 | NO$_2$ | CH$_2$CH=CH$_2$ | |
| 4.91 | 2 | NO$_2$ | CH$_2$C≡CH | |
| 4.92 | 2 | NO$_2$ | CH$_2$CH=CHC$_6$H$_5$ | |
| 4.93 | 2 | NO$_2$ | CH$_2$C≡CC$_6$H$_5$ | |
| 4.94 | 0 | NO$_2$ | CH$_2$SCH$_3$ | |
| 4.95 | 0 | NO$_2$ | CH$_2$SC$_2$H$_5$ | |
| 4.96 | 0 | NO$_2$ | CH$_2$S-n-C$_3$H$_7$ | |
| 4.97 | 0 | NO$_2$ | CH$_2$S-i-C$_3$H$_7$ | |
| 4.98 | 0 | NO$_2$ | CH$_2$S-n-C$_4$H$_9$ | |
| 4.99 | 0 | NO$_2$ | CH$_2$S-t-C$_4$H$_9$ | |
| 4.100 | 0 | NO$_2$ | CH$_2$S-cyclo-C$_3$H$_5$ | |
| 4.101 | 0 | NO$_2$ | CH$_2$SCH$_2$C$_6$H$_5$ | |
| 4.102 | 0 | NO$_2$ | CH$_2$SCH$_2$C$_6$H$_4$-4-CH$_3$ | |
| 4.103 | 0 | NO$_2$ | CH$_2$SCH$_2$C$_6$H$_4$-4-OCH$_3$ | |
| 4.104 | 0 | NO$_2$ | CH$_2$SCH$_2$C$_6$H$_4$-4-Cl | |
| 4.105 | 0 | NO$_2$ | CH$_2$SCH$_2$C$_6$H$_4$-4-NO$_2$ | |
| 4.106 | 0 | NO$_2$ | CH$_2$SCH$_2$-2-furyl | |
| 4.107 | 0 | NO$_2$ | CH$_2$SCH$_2$-2-thienyl | |
| 4.108 | 0 | NO$_2$ | CH$_2$SC$_6$H$_5$ | |
| 4.109 | 0 | NO$_2$ | CH$_2$SC$_6$H$_4$-4-CH$_3$ | |
| 4.110 | 0 | NO$_2$ | CH$_2$SC$_6$H$_4$-4-OCH$_3$ | |
| 4.111 | 0 | NO$_2$ | CH$_2$SC$_6$H$_4$-4-Cl | |
| 4.112 | 0 | NO$_2$ | CH$_2$SC$_6$H$_4$-4-NO$_2$ | |
| 4.113 | 0 | NO$_2$ | CH$_2$SCH$_2$CH=CH$_2$ | |
| 4.114 | 0 | NO$_2$ | CH$_2$SCH$_2$C≡CH | |
| 4.115 | 0 | NO$_2$ | CH$_2$SCH$_2$CH=CHC$_6$H$_5$ | |
| 4.116 | 0 | NO$_2$ | CH$_2$SCH$_2$C≡CC$_6$H$_5$ | |
| 4.117 | 0 | NO$_2$ | | |
| 4.118 | 0 | CN | CH$_3$ | |
| 4.119 | 0 | CN | C$_2$H$_5$ | |
| 4.120 | 0 | CN | n-C$_3$H$_7$ | |
| 4.121 | 0 | CN | i-C$_3$H$_7$ | |
| 4.122 | 0 | CN | n-C$_4$H$_9$ | |
| 4.123 | 0 | CN | t-C$_4$H$_9$ | |
| 4.124 | 0 | CN | cyclo-C$_3$H$_5$ | |
| 4.125 | 0 | CN | CH$_2$C$_6$H$_5$ | |
| 4.126 | 0 | CN | CH$_2$C$_6$H$_4$-4-CH$_3$ | |
| 4.127 | 0 | CN | CH$_2$C$_6$H$_4$-4-OCH$_3$ | |
| 4.128 | 0 | CN | CH$_2$C$_6$H$_4$-4-Cl | |

TABLE 4-continued

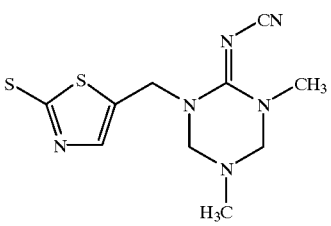

| Compound No. | n | Y | R<sub>6</sub> | Physical data |
|---|---|---|---|---|
| 4.129 | 0 | CN | $CH_2C_6H_4$-4-$NO_2$ | |
| 4.130 | 0 | CN | $CH_2$-2-furyl | |
| 4.131 | 0 | CN | $CH_2$-2-thienyl | |
| 4.132 | 0 | CN | $C_6H_5$ | |
| 4.133 | 0 | CN | $C_6H_4$-4-$CH_3$ | |
| 4.134 | 0 | CN | $C_6H_4$-4-$OCH_3$ | |
| 4.135 | 0 | CN | $C_6H_4$-4-Cl | |
| 4.136 | 0 | CN | $C_6H_4$-4-$NO_2$ | |
| 4.137 | 0 | CN | $CH_2CH{=}CH_2$ | |
| 4.138 | 0 | CN | $CH_2C{\equiv}CH$ | |
| 4.139 | 0 | CN | $CH_2CH{=}CHC_6H_5$ | |
| 4.140 | 0 | CN | $CH_2C{\equiv}CC_6H_5$ | |
| 4.141 | 0 | CN | $SCH_3$ | |
| 4.142 | 0 | CN | $SC_2H_5$ | |
| 4.143 | 0 | CN | S-n-$C_3H_7$ | |
| 4.144 | 0 | CN | S-i-$C_3H_7$ | |
| 4.145 | 0 | CN | S-n-$C_4H_9$ | |
| 4.146 | 0 | CN | S-t-$C_4H_9$ | |
| 4.147 | 0 | CN | S-cyclo-$C_3H_5$ | |
| 4.148 | 0 | CN | $SCH_2C_6H_5$ | |
| 4.149 | 0 | CN | $SCH_2C_6H_4$-4-$CH_3$ | |
| 4.150 | 0 | CN | $SCH_2C_6H_4$-4-$OCH_3$ | |
| 4.151 | 0 | CN | $SCH_2C_6H_4$-4-Cl | |
| 4.152 | 0 | CN | $SCH_2C_6H_4$-4-$NO_2$ | |
| 4.153 | 0 | CN | $SCH_2$-2-furyl | |
| 4.154 | 0 | CN | $SCH_2$-2-thienyl | |
| 4.155 | 0 | CN | $SC_6H_5$ | |
| 4.156 | 0 | CN | $SC_6H_4$-4-$CH_3$ | |
| 4.157 | 0 | CN | $SC_6H_4$-4-$OCH_3$ | |
| 4.158 | 0 | CN | $SC_6H_4$-4-Cl | |
| 4.159 | 0 | CN | $SC_6H_4$-4-$NO_2$ | |
| 4.160 | 0 | CN | $SCH_2CH{=}CH_2$ | |
| 4.161 | 0 | CN | $SCH_2C{\equiv}CH$ | |
| 4.162 | 0 | CN | $SCH_2CH{=}CHC_6H_5$ | |
| 4.163 | 0 | CN | $SCH_2C{\equiv}CC_6H_5$ | |
| 4.164 | 0 | CN | | |
| 4.165 | 1 | CN | $CH_3$ | |
| 4.166 | 1 | CN | $C_2H_5$ | |
| 4.167 | 1 | CN | n-$C_3H_7$ | |
| 4.168 | 1 | CN | i-$C_3H_7$ | |
| 4.169 | 1 | CN | n-$C_4H_9$ | |
| 4.170 | 1 | CN | t-$C_4H_9$ | |
| 4.171 | 1 | CN | cyclo-$C_3H_5$ | |
| 4.172 | 1 | CN | $CH_2C_6H_5$ | |
| 4.173 | 1 | CN | $CH_2C_6H_4$-4-$CH_3$ | |
| 4.174 | 1 | CN | $CH_2C_6H_4$-4-$OCH_3$ | |
| 4.175 | 1 | CN | $CH_2C_6H_4$-4-Cl | |
| 4.176 | 1 | CN | $CH_2C_6H_4$-4-$NO_2$ | |
| 4.177 | 1 | CN | $CH_2$-2-furyl | |
| 4.178 | 1 | CN | $CH_2$-2-thienyl | |
| 4.179 | 1 | CN | $C_6H_5$ | |
| 4.180 | 1 | CN | $C_6H_4$-4-$CH_3$ | |
| 4.181 | 1 | CN | $C_6H_4$-4-$OCH_3$ | |

TABLE 4-continued

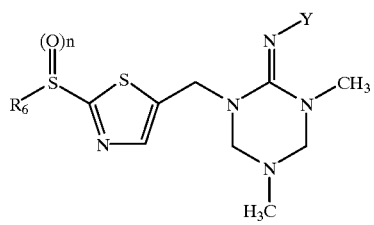

| Compound No. | n | Y | R$_6$ | Physical data |
|---|---|---|---|---|
| 4.182 | 1 | CN | C$_6$H$_4$-4-Cl | |
| 4.183 | 1 | CN | C$_6$H$_4$-4-NO$_2$ | |
| 4.184 | 1 | CN | CH$_2$CH=CH$_2$ | |
| 4.185 | 1 | CN | CH$_2$C≡CH | |
| 4.186 | 1 | CN | CH$_2$CH=CHC$_6$H$_5$ | |
| 4.187 | 1 | CN | CH$_2$C≡CC$_6$H$_5$ | |
| 4.188 | 2 | CN | CH$_3$ | |
| 4.189 | 2 | CN | C$_2$H$_5$ | |
| 4.190 | 2 | CN | n-C$_3$H$_7$ | |
| 4.191 | 2 | CN | i-C$_3$H$_7$ | |
| 4.192 | 2 | CN | n-C$_4$H$_9$ | |
| 4.193 | 2 | CN | t-C$_4$H$_9$ | |
| 4.194 | 2 | CN | cyclo-C$_3$H$_5$ | |
| 4.195 | 2 | CN | CH$_2$C$_6$H$_5$ | |
| 4.196 | 2 | CN | CH$_2$C$_6$H$_4$-4-CH$_3$ | |
| 4.197 | 2 | CN | CH$_2$C$_6$H$_4$-4-OCH$_3$ | |
| 4.198 | 2 | CN | CH$_2$C$_6$H$_4$-4-Cl | |
| 4.199 | 2 | CN | CH$_2$C$_6$H$_4$-4-NO$_2$ | |
| 4.200 | 2 | CN | CH$_2$-2-furyl | |
| 4.201 | 2 | CN | CH$_2$-2-thienyl | |
| 4.202 | 2 | CN | C$_6$H$_5$ | |
| 4.203 | 2 | CN | C$_6$H$_4$-4-CH$_3$ | |
| 4.204 | 2 | CN | C$_6$H$_4$-4-OCH$_3$ | |
| 4.205 | 2 | CN | C$_6$H$_4$-4-Cl | |
| 4.206 | 2 | CN | C$_6$H$_4$-4-NO$_2$ | |
| 4.207 | 2 | CN | CH$_2$CH=CH$_2$ | |
| 4.208 | 2 | CN | CH$_2$C≡CH | |
| 4.209 | 2 | CN | CH$_2$CH=CHC$_6$H$_5$ | |
| 4.210 | 2 | CN | CH$_2$C≡CC$_6$H$_5$ | |
| 4.211 | 0 | CN | CH$_2$SCH$_3$ | |
| 4.212 | 0 | CN | CH$_2$SC$_2$H$_5$ | |
| 4.213 | 0 | CN | CH$_2$S-n-C$_3$H$_7$ | |
| 4.214 | 0 | CN | CH$_2$S-i-C$_3$H$_7$ | |
| 4.215 | 0 | CN | CH$_2$S-n-C$_4$H$_9$ | |
| 4.216 | 0 | CN | CH$_2$S-t-C$_4$H$_9$ | |
| 4.217 | 0 | CN | CH$_2$S-cyclo-C$_3$H$_5$ | |
| 4.218 | 0 | CN | CH$_2$SCH$_2$C$_6$H$_5$ | |
| 4.219 | 0 | CN | CH$_2$SCH$_2$C$_6$H$_4$-4-CH$_3$ | |
| 4.220 | 0 | CN | CH$_2$SCH$_2$C$_6$H$_4$-4-OCH$_3$ | |
| 4.221 | 0 | CN | CH$_2$SCH$_2$C$_6$H$_4$-4-Cl | |
| 4.222 | 0 | CN | CH$_2$SCH$_2$C$_6$H$_4$-4-NO$_2$ | |
| 4.223 | 0 | CN | CH$_2$SCH$_2$-2-furyl | |
| 4.224 | 0 | CN | CH$_2$SCH$_2$-2-thienyl | |
| 4.225 | 0 | CN | CH$_2$SC$_6$H$_5$ | |
| 4.226 | 0 | CN | CH$_2$SC$_6$H$_4$-4-CH$_3$ | |
| 4.227 | 0 | CN | CH$_2$SC$_6$H$_4$-4-OCH$_3$ | |
| 4.228 | 0 | CN | CH$_2$SC$_6$H$_4$-4-Cl | |
| 4.229 | 0 | CN | CH$_2$SC$_6$H$_4$-4-NO$_2$ | |
| 4.230 | 0 | CN | CH$_2$SCH$_2$CH=CH$_2$ | |
| 4.231 | 0 | CN | CH$_2$SCH$_2$C≡CH | |
| 4.232 | 0 | CN | CH$_2$SCH$_2$CH=CHC$_6$H$_5$ | |
| 4.233 | 0 | CN | CH$_2$SCH$_2$C≡CC$_6$H$_5$ | |
| 4.234 | 0 | CN | | |

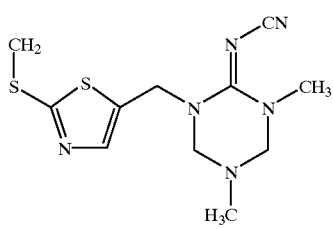

TABLE 5

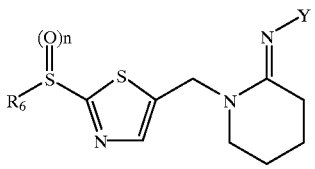

| Compound No. | n | Y | R$_6$ | Phys. data |
|---|---|---|---|---|
| 5.1 | 0 | NO$_2$ | CH$_3$ | |
| 5.2 | 0 | NO$_2$ | C$_2$H$_5$ | |
| 5.3 | 0 | NO$_2$ | n-C$_3$H$_7$ | |
| 5.4 | 0 | NO$_2$ | i-C$_3$H$_7$ | |
| 5.5 | 0 | NO$_2$ | n-C$_4$H$_9$ | |
| 5.6 | 0 | NO$_2$ | t-C$_4$H$_9$ | |
| 5.7 | 0 | NO$_2$ | cyclo-C$_3$H$_5$ | |
| 5.8 | 0 | NO$_2$ | CH$_2$C$_6$H$_5$ | |
| 5.9 | 0 | NO$_2$ | CH$_2$C$_6$H$_4$-4-CH$_3$ | |
| 5.10 | 0 | NO$_2$ | CH$_2$C$_6$H$_4$-4-OCH$_3$ | |
| 5.11 | 0 | NO$_2$ | CH$_2$C$_6$H$_4$-4-Cl | |
| 5.12 | 0 | NO$_2$ | CH$_2$C$_6$H$_4$-4-NO$_2$ | |
| 5.13 | 0 | NO$_2$ | CH$_2$-2-furyl | |
| 5.14 | 0 | NO$_2$ | CH$_2$-2-thienyl | |
| 5.15 | 0 | NO$_2$ | C$_6$H$_5$ | |
| 5.16 | 0 | NO$_2$ | C$_6$H$_4$-4-CH$_3$ | |
| 5.17 | 0 | NO$_2$ | C$_6$H$_4$-4-OCH$_3$ | |
| 5.18 | 0 | NO$_2$ | C$_6$H$_4$-4-Cl | |
| 5.19 | 0 | NO$_2$ | C$_6$H$_4$-4-NO$_2$ | |
| 5.20 | 0 | NO$_2$ | CH$_2$CH=CH$_2$ | |
| 5.21 | 0 | NO$_2$ | CH$_2$C≡CH | |
| 5.22 | 0 | NO$_2$ | CH$_2$CH=CHC$_6$H$_5$ | |
| 5.23 | 0 | NO$_2$ | CH$_2$C≡CC$_6$H$_5$ | |
| 5.24 | 0 | NO$_2$ | SCH$_3$ | |
| 5.25 | 0 | NO$_2$ | SC$_2$H$_5$ | |
| 5.26 | 0 | NO$_2$ | S-n-C$_3$H$_7$ | |
| 5.27 | 0 | NO$_2$ | S-i-C$_3$H$_7$ | |
| 5.28 | 0 | NO$_2$ | S-n-C$_4$H$_9$ | |
| 5.29 | 0 | NO$_2$ | S-t-C$_4$H$_9$ | |
| 5.30 | 0 | NO$_2$ | S-cyclo-C$_3$H$_5$ | |
| 5.31 | 0 | NO$_2$ | SCH$_2$C$_6$H$_5$ | |
| 5.32 | 0 | NO$_2$ | SCH$_2$C$_6$H$_4$-4-CH$_3$ | |
| 5.33 | 0 | NO$_2$ | SCH$_2$C$_6$H$_4$-4-OCH$_3$ | |
| 5.34 | 0 | NO$_2$ | SCH$_2$C$_6$H$_4$-4-Cl | |
| 5.35 | 0 | NO$_2$ | SCH$_2$C$_6$H$_4$-4-NO$_2$ | |
| 5.36 | 0 | NO$_2$ | SCH$_2$-2-furyl | |
| 5.37 | 0 | NO$_2$ | SCH$_2$-2-thienyl | |
| 5.38 | 0 | NO$_2$ | SC$_6$H$_5$ | |
| 5.39 | 0 | NO$_2$ | SC$_6$H$_4$-4-CH$_3$ | |
| 5.40 | 0 | NO$_2$ | SC$_6$H$_4$-4-OCH$_3$ | |
| 5.41 | 0 | NO$_2$ | SC$_6$H$_4$-4-Cl | |
| 5.42 | 0 | NO$_2$ | SC$_6$H$_4$-4-NO$_2$ | |
| 5.43 | 0 | NO$_2$ | SCH$_2$CH=CH$_2$ | |
| 5.44 | 0 | NO$_2$ | SCH$_2$C≡CH | |
| 5.45 | 0 | NO$_2$ | SCH$_2$CH=CHC$_6$H$_5$ | |
| 5.46 | 0 | NO$_2$ | SCH$_2$C≡CC$_6$H$_5$ | |
| 5.47 | 0 | NO$_2$ | | |
| 5.48 | 1 | NO$_2$ | CH$_3$ | |
| 5.49 | 1 | NO$_2$ | C$_2$H$_5$ | |
| 5.50 | 1 | NO$_2$ | n-C$_3$H$_7$ | |
| 5.51 | 1 | NO$_2$ | i-C$_3$H$_7$ | |
| 5.52 | 1 | NO$_2$ | n-C$_4$H$_9$ | |
| 5.53 | 1 | NO$_2$ | t-C$_4$H$_9$ | |
| 5.54 | 1 | NO$_2$ | cyclo-C$_3$H$_5$ | |
| 5.55 | 1 | NO$_2$ | CH$_2$C$_6$H$_5$ | |
| 5.56 | 1 | NO$_2$ | CH$_2$C$_6$H$_4$-4-CH$_3$ | |
| 5.57 | 1 | NO$_2$ | CH$_2$C$_6$H$_4$-4-OCH$_3$ | |
| 5.58 | 1 | NO$_2$ | CH$_2$C$_6$H$_4$-4-Cl | |
| 5.59 | 1 | NO$_2$ | CH$_2$C$_6$H$_4$-4-NO$_2$ | |
| 5.60 | 1 | NO$_2$ | CH$_2$-2-furyl | |
| 5.61 | 1 | NO$_2$ | CH$_2$-2-thienyl | |
| 5.62 | 1 | NO$_2$ | C$_6$H$_5$ | |
| 5.63 | 1 | NO$_2$ | C$_6$H$_4$-4-CH$_3$ | |
| 5.64 | 1 | NO$_2$ | C$_6$H$_4$-4-OCH$_3$ | |
| 5.65 | 1 | NO$_2$ | C$_6$H$_4$-4-Cl | |
| 5.66 | 1 | NO$_2$ | C$_6$H$_4$-4-NO$_2$ | |
| 5.67 | 1 | NO$_2$ | CH$_2$CH=CH$_2$ | |
| 5.68 | 1 | NO$_2$ | CH$_2$C≡CH | |
| 5.69 | 1 | NO$_2$ | CH$_2$CH=CHC$_6$H$_5$ | |
| 5.70 | 1 | NO$_2$ | CH$_2$C≡CC$_6$H$_5$ | |
| 5.71 | 2 | NO$_2$ | CH$_3$ | |
| 5.72 | 2 | NO$_2$ | C$_2$H$_5$ | |
| 5.73 | 2 | NO$_2$ | n-C$_3$H$_7$ | |
| 5.74 | 2 | NO$_2$ | i-C$_3$H$_7$ | |
| 5.75 | 2 | NO$_2$ | n-C$_4$H$_9$ | |
| 5.76 | 2 | NO$_2$ | t-C$_4$H$_9$ | |
| 5.77 | 2 | NO$_2$ | cyclo-C$_3$H$_5$ | |
| 5.78 | 2 | NO$_2$ | CH$_2$C$_6$H$_5$ | |
| 5.79 | 2 | NO$_2$ | CH$_2$C$_6$H$_4$-4-CH$_3$ | |
| 5.80 | 2 | NO$_2$ | CH$_2$C$_6$H$_4$-4-OCH$_3$ | |
| 5.81 | 2 | NO$_2$ | CH$_2$C$_6$H$_4$-4-Cl | |
| 5.82 | 2 | NO$_2$ | CH$_2$C$_6$H$_4$-4-NO$_2$ | |
| 5.83 | 2 | NO$_2$ | CH$_2$-2-furyl | |
| 5.84 | 2 | NO$_2$ | CH$_2$-2-thienyl | |
| 5.85 | 2 | NO$_2$ | C$_6$H$_5$ | |
| 5.86 | 2 | NO$_2$ | C$_6$H$_4$-4-CH$_3$ | |
| 5.87 | 2 | NO$_2$ | C$_6$H$_4$-4-OCH$_3$ | |
| 5.88 | 2 | NO$_2$ | C$_6$H$_4$-4-Cl | |
| 5.89 | 2 | NO$_2$ | C$_6$H$_4$-4-NO$_2$ | |
| 5.90 | 2 | NO$_2$ | CH$_2$CH=CH$_2$ | |
| 5.91 | 2 | NO$_2$ | CH$_2$C≡CH | |
| 5.92 | 2 | NO$_2$ | CH$_2$CH=CHC$_6$H$_5$ | |
| 5.93 | 2 | NO$_2$ | CH$_2$C≡CC$_6$H$_5$ | |
| 5.94 | 0 | NO$_2$ | CH$_2$SCH$_3$ | |
| 5.95 | 0 | NO$_2$ | CH$_2$SC$_2$H$_5$ | |
| 5.96 | 0 | NO$_2$ | CH$_2$S-n-C$_3$H$_7$ | |
| 5.97 | 0 | NO$_2$ | CH$_2$S-i-C$_3$H$_7$ | |
| 5.98 | 0 | NO$_2$ | CH$_2$S-n-C$_4$H$_9$ | |
| 5.99 | 0 | NO$_2$ | CH$_2$S-t-C$_4$H$_9$ | |
| 5.100 | 0 | NO$_2$ | CH$_2$S-cyclo-C$_3$H$_5$ | |
| 5.101 | 0 | NO$_2$ | CH$_2$SCH$_2$C$_6$H$_5$ | |
| 5.102 | 0 | NO$_2$ | CH$_2$SCH$_2$C$_6$H$_4$-4-CH$_3$ | |
| 5.103 | 0 | NO$_2$ | CH$_2$SCH$_2$C$_6$H$_4$-4-OCH$_3$ | |
| 5.104 | 0 | NO$_2$ | CH$_2$SCH$_2$C$_6$H$_4$-4-Cl | |
| 5.105 | 0 | NO$_2$ | CH$_2$SCH$_2$C$_6$H$_4$-4-NO$_2$ | |
| 5.106 | 0 | NO$_2$ | CH$_2$SCH$_2$-2-furyl | |
| 5.107 | 0 | NO$_2$ | CH$_2$SCH$_2$-2-thienyl | |
| 5.108 | 0 | NO$_2$ | CH$_2$SC$_6$H$_5$ | |
| 5.109 | 0 | NO$_2$ | CH$_2$SC$_6$H$_4$-4-CH$_3$ | |
| 5.110 | 0 | NO$_2$ | CH$_2$SC$_6$H$_4$-4-OCH$_3$ | |
| 5.111 | 0 | NO$_2$ | CH$_2$SC$_6$H$_4$-4-Cl | |
| 5.112 | 0 | NO$_2$ | CH$_2$SC$_6$H$_4$-4-NO$_2$ | |
| 5.113 | 0 | NO$_2$ | CH$_2$SCH$_2$CH=CH$_2$ | |
| 5.114 | 0 | NO$_2$ | CH$_2$SCH$_2$≡CH | |
| 5.115 | 0 | NO$_2$ | CH$_2$SCH$_2$CH=CHC$_6$H$_5$ | |
| 5.116 | 0 | NO$_2$ | CH$_2$SCH$_2$C≡C$_6$H$_5$ | |

TABLE 5-continued

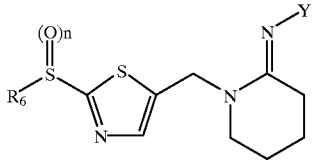

| Compound No. | n | Y | R₆ | Phys. data |
|---|---|---|---|---|
| 5.117 | 0 | $NO_2$ | | |

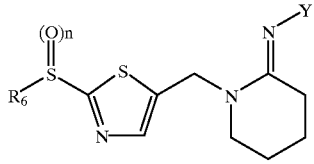

| 5.118 | 0 | CN | $CH_3$ | |
| 5.119 | 0 | CN | $C_2H_5$ | |
| 5.120 | 0 | CN | $n-C_3H_7$ | |
| 5.121 | 0 | CN | $i-C_3H_7$ | |
| 5.122 | 0 | CN | $n-C_4H_9$ | |
| 5.123 | 0 | CN | $t-C_4H_9$ | |
| 5.124 | 0 | CN | $cyclo-C_3H_5$ | |
| 5.125 | 0 | CN | $CH_2C_6H_5$ | |
| 5.126 | 0 | CN | $CH_2C_6H_4$-4-$CH_3$ | |
| 5.127 | 0 | CN | $CH_2C_6H_4$-4-$OCH_3$ | |
| 5.128 | 0 | CN | $CH_2C_6H_4$-4-Cl | |
| 5.129 | 0 | CN | $CH_2C_6H_4$-4-$NO_2$ | |
| 5.130 | 0 | CN | $CH_2$-2-furyl | |
| 5.131 | 0 | CN | $CH_2$-2-thienyl | |
| 5.132 | 0 | CN | $C_6H_5$ | |
| 5.133 | 0 | CN | $C_6H_4$-4-$CH_3$ | |
| 5.134 | 0 | CN | $C_6H_4$-4-$OCH_3$ | |
| 5.135 | 0 | CN | $C_6H_4$-4-Cl | |
| 5.136 | 0 | CN | $C_6H_4$-4-$NO_2$ | |
| 5.137 | 0 | CN | $CH_2CH=CH_2$ | |
| 5.138 | 0 | CN | $CH_2C\equiv CH$ | |
| 5.139 | 0 | CN | $CH_2CH=CHC_6H_5$ | |
| 5.140 | 0 | CN | $CH_2C\equiv CC_6H_5$ | |
| 5.141 | 0 | CN | $SCH_3$ | |
| 5.142 | 0 | CN | $SC_2H_5$ | |
| 5.143 | 0 | CN | $S-n-C_3H_7$ | |
| 5.144 | 0 | CN | $S-i-C_3H_7$ | |
| 5.145 | 0 | CN | $S-n-C_4H_9$ | |
| 5.146 | 0 | CN | $S-t-C_4H_9$ | |
| 5.147 | 0 | CN | $S-cyclo-C_3H_5$ | |
| 5.148 | 0 | CN | $SCH_2C_6H_5$ | |
| 5.149 | 0 | CN | $SCH_2C_6H_4$-4-$CH_3$ | |
| 5.150 | 0 | CN | $SCH_2C_6H_4$-4-$OCH_3$ | |
| 5.151 | 0 | CN | $SCH_2C_6H_4$-4-Cl | |
| 5.152 | 0 | CN | $SCH_2C_6H_4$-4-$NO_2$ | |
| 5.153 | 0 | CN | $SCH_2$-2-furyl | |
| 5.154 | 0 | CN | $SCH_2$-2-thienyl | |
| 5.155 | 0 | CN | $SC_6H_5$ | |
| 5.156 | 0 | CN | $SC_6H_4$-4-$CH_3$ | |
| 5.157 | 0 | CN | $SC_6H_4$-4-$OCH_3$ | |
| 5.158 | 0 | CN | $SC_6H_4$-4-Cl | |
| 5.159 | 0 | CN | $SC_6H_4$-4-$NO_2$ | |
| 5.160 | 0 | CN | $SCH_2CH=CH_2$ | |
| 5.161 | 0 | CN | $SCH_2C\equiv CH$ | |
| 5.162 | 0 | CN | $SCH_2CH=CHC_6H_5$ | |
| 5.163 | 0 | CN | $SCH_2C\equiv CC_6H_5$ | |
| 5.164 | 0 | CN | | |
| 5.165 | 1 | CN | $CH_3$ | |
| 5.166 | 1 | CN | $C_2H_5$ | |
| 5.167 | 1 | CN | $n-C_3H_7$ | |
| 5.168 | 1 | CN | $i-C_3H_7$ | |
| 5.169 | 1 | CN | $n-C_4H_9$ | |
| 5.170 | 1 | CN | $t-C_4H_9$ | |
| 5.171 | 1 | CN | $cyclo-C_3H_5$ | |
| 5.172 | 1 | CN | $CH_2C_6H_5$ | |
| 5.173 | 1 | CN | $CH_2C_6H_4$-4-$CH_3$ | |
| 5.174 | 1 | CN | $CH_2C_6H_4$-4-$OCH_3$ | |
| 5.175 | 1 | CN | $CH_2C_6H_4$-4-Cl | |
| 5.176 | 1 | CN | $CH_2C_6H_4$-4-$NO_2$ | |
| 5.177 | 1 | CN | $CH_2$-2-furyl | |
| 5.178 | 1 | CN | $CH_2$-2-thienyl | |
| 5.179 | 1 | CN | $C_6H_5$ | |
| 5.180 | 1 | CN | $C_6H_4$-4-$CH_3$ | |
| 5.181 | 1 | CN | $C_6H_4$-4-$OCH_3$ | |
| 5.182 | 1 | CN | $C_6H_4$-4-Cl | |
| 5.183 | 1 | CN | $C_6H_4$-4-$NO_2$ | |
| 5.184 | 1 | CN | $CH_2CH=CH_2$ | |
| 5.185 | 1 | CN | $CH_2C\equiv CH$ | |
| 5.186 | 1 | CN | $CH_2CH=CHC_6H_5$ | |
| 5.187 | 1 | CN | $CH_2C\equiv CC_6H_5$ | |
| 5.188 | 2 | CN | $CH_3$ | |
| 5.189 | 2 | CN | $C_2H_5$ | |
| 5.190 | 2 | CN | $n-C_3H_7$ | |
| 5.191 | 2 | CN | $i-C_3H_7$ | |
| 5.192 | 2 | CN | $n-C_4H_9$ | |
| 5.193 | 2 | CN | $t-C_4H_9$ | |
| 5.194 | 2 | CN | $cyclo-C_3H_5$ | |
| 5.195 | 2 | CN | $CH_2C_6H_5$ | |
| 5.196 | 2 | CN | $CH_2C_6H_4$-4-$CH_3$ | |
| 5.197 | 2 | CN | $CH_2C_6H_4$-4-$OCH_3$ | |
| 5.198 | 2 | CN | $CH_2C_6H_4$-4-Cl | |
| 5.199 | 2 | CN | $CH_2C_6H_4$-4-$NO_2$ | |
| 5.200 | 2 | CN | $CH_2$-2-furyl | |
| 5.201 | 2 | CN | $CH_2$-2-thienyl | |
| 5.202 | 2 | CN | $C_6H_5$ | |
| 5.203 | 2 | CN | $C_6H_4$-4-$CH_3$ | |
| 5.204 | 2 | CN | $C_6H_4$-4-$OCH_3$ | |
| 5.205 | 2 | CN | $C_6H_4$-4-Cl | |
| 5.206 | 2 | CN | $C_6H_4$-4-$NO_2$ | |
| 5.207 | 2 | CN | $CH_2CH=CH_2$ | |
| 5.208 | 2 | CN | $CH_2C\equiv CH$ | |
| 5.209 | 2 | CN | $CH_2CH=CHC_6H_5$ | |
| 5.210 | 2 | CN | $CH_2C\equiv CC_6H_5$ | |
| 5.211 | 0 | CN | $CH_2SCH_3$ | |
| 5.212 | 0 | CN | $CH_2SC_2H_5$ | |
| 5.213 | 0 | CN | $CH_2S-n-C_3H_7$ | |
| 5.214 | 0 | CN | $CH_2S-i-C_3H_7$ | |
| 5.215 | 0 | CN | $CH_2S-n-C_4H_9$ | |
| 5.216 | 0 | CN | $CH_2S-t-C_4H_9$ | |
| 5.217 | 0 | CN | $CH_2S-cyclo-C_3H_5$ | |
| 5.218 | 0 | CN | $CH_2SCH_2C_6H_5$ | |
| 5.219 | 0 | CN | $CH_2SCH_2C_6H_4$-4-$CH_3$ | |
| 5.220 | 0 | CN | $CH_2SCH_2C_6H_4$-4-$OCH_3$ | |
| 5.221 | 0 | CN | $CH_2SCH_2C_6H_4$-4-Cl | |
| 5.222 | 0 | CN | $CH_2SCH_2C_6H_4$-4-$NO_2$ | |
| 5.223 | 0 | CN | $CH_2SCH_2$-2-furyl | |
| 5.224 | 0 | CN | $CH_2SCH_2$-2-thienyl | |
| 5.225 | 0 | CN | $CH_2SC_6H_5$ | |
| 5.226 | 0 | CN | $CH_2SC_6H_4$-4-$CH_3$ | |
| 5.227 | 0 | CN | $CH_2SC_6H_4$-4-$OCH_3$ | |
| 5.228 | 0 | CN | $CH_2SC_6H_4$-4-Cl | |
| 5.229 | 0 | CN | $CH_2SC_6H_4$-4-$NO_2$ | |

TABLE 5-continued

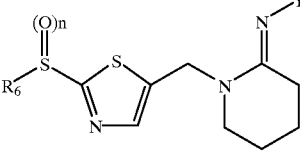

| Compound No. | n | Y | R$_6$ | Phys. data |
|---|---|---|---|---|
| 5.230 | 0 | CN | CH$_2$SCH$_2$CH=CH$_2$ | |
| 5.231 | 0 | CN | CH$_2$SCH$_2$C≡CH | |
| 5.232 | 0 | CN | CH$_2$SCH$_2$CH=CHC$_6$H$_5$ | |
| 5.233 | 0 | CN | CH$_2$SCH$_2$C≡CC$_6$H$_5$ | |
| 5.234 | 0 | CN | 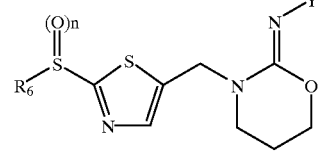 | |

TABLE 6

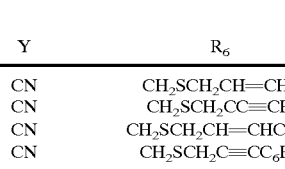

| Compound No. | n | Y | R$_6$ | Phys. data |
|---|---|---|---|---|
| 6.1 | 0 | NO$_2$ | CH$_3$ | |
| 6.2 | 0 | NO$_2$ | C$_2$H$_5$ | |
| 6.3 | 0 | NO$_2$ | n-C$_3$H$_7$ | |
| 6.4 | 0 | NO$_2$ | i-C$_3$H$_7$ | |
| 6.5 | 0 | NO$_2$ | n-C$_4$H$_9$ | |
| 6.6 | 0 | NO$_2$ | t-C$_4$H$_9$ | |
| 6.7 | 0 | NO$_2$ | cyclo-C$_3$H$_5$ | |
| 6.8 | 0 | NO$_2$ | CH$_2$C$_6$H$_5$ | |
| 6.9 | 0 | NO$_2$ | CH$_2$C$_6$H$_4$-4-CH$_3$ | |
| 6.10 | 0 | NO$_2$ | CH$_2$C$_6$H$_4$-4-OCH$_3$ | |
| 6.11 | 0 | NO$_2$ | CH$_2$C$_6$H$_4$-4-Cl | |
| 6.12 | 0 | NO$_2$ | CH$_2$C$_6$H$_4$-4-NO$_2$ | |
| 6.13 | 0 | NO$_2$ | CH$_2$-2-furyl | |
| 6.14 | 0 | NO$_2$ | CH$_2$-2-thienyl | |
| 6.15 | 0 | NO$_2$ | C$_6$H$_5$ | |
| 6.16 | 0 | NO$_2$ | C$_6$H$_4$-4-CH$_3$ | |
| 6.17 | 0 | NO$_2$ | C$_6$H$_4$-4-OCH$_3$ | |
| 6.18 | 0 | NO$_2$ | C$_6$H$_4$-4-Cl | |
| 6.19 | 0 | NO$_2$ | C$_6$H$_4$-4-NO$_2$ | |
| 6.20 | 0 | NO$_2$ | CH$_2$CH=CH$_2$ | |
| 6.21 | 0 | NO$_2$ | CH$_2$C≡CH | |
| 6.22 | 0 | NO$_2$ | CH$_2$CH=CHC$_6$H$_5$ | |
| 6.23 | 0 | NO$_2$ | CH$_2$C≡CC$_6$H$_5$ | |
| 6.24 | 0 | NO$_2$ | SCH$_3$ | |
| 6.25 | 0 | NO$_2$ | SC$_2$H$_5$ | |
| 6.26 | 0 | NO$_2$ | S-n-C$_3$H$_7$ | |
| 6.27 | 0 | NO$_2$ | S-i-C$_3$H$_7$ | |
| 6.28 | 0 | NO$_2$ | S-n-C$_4$H$_9$ | |
| 6.29 | 0 | NO$_2$ | S-t-C$_4$H$_9$ | |
| 6.30 | 0 | NO$_2$ | S-cyclo-C$_3$H$_5$ | |
| 6.31 | 0 | NO$_2$ | SCH$_2$C$_6$H$_5$ | |
| 6.32 | 0 | NO$_2$ | SCH$_2$C$_6$H$_4$-4-CH$_3$ | |
| 6.33 | 0 | NO$_2$ | SCH$_2$C$_6$H$_4$-4-OCH$_3$ | |
| 6.34 | 0 | NO$_2$ | SCH$_2$C$_6$H$_4$-4-Cl | |

TABLE 6-continued

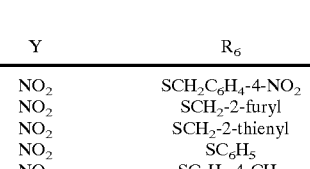

| Compound No. | n | Y | R$_6$ | Phys. data |
|---|---|---|---|---|
| 6.35 | 0 | NO$_2$ | SCH$_2$C$_6$H$_4$-4-NO$_2$ | |
| 6.36 | 0 | NO$_2$ | SCH$_2$-2-furyl | |
| 6.37 | 0 | NO$_2$ | SCH$_2$-2-thienyl | |
| 6.38 | 0 | NO$_2$ | SC$_6$H$_5$ | |
| 6.39 | 0 | NO$_2$ | SC$_6$H$_4$-4-CH$_3$ | |
| 6.40 | 0 | NO$_2$ | SC$_6$H$_4$-4-OCH$_3$ | |
| 6.41 | 0 | NO$_2$ | SC$_6$H$_4$-4-Cl | |
| 6.42 | 0 | NO$_2$ | SC$_6$H$_4$-4-NO$_2$ | |
| 6.43 | 0 | NO$_2$ | SCH$_2$CH=CH$_2$ | |
| 6.44 | 0 | NO$_2$ | SCH$_2$C≡CH | |
| 6.45 | 0 | NO$_2$ | SCH$_2$CH=CHC$_6$H$_5$ | |
| 6.46 | 0 | NO$_2$ | SCH$_2$C≡C$_6$H$_5$ | |
| 6.47 | 0 | NO$_2$ | 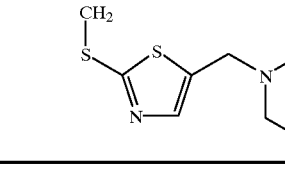 | |
| 6.48 | 1 | NO$_2$ | CH$_3$ | |
| 6.49 | 1 | NO$_2$ | C$_2$H$_5$ | |
| 6.50 | 1 | NO$_2$ | n-C$_3$H$_7$ | |
| 6.51 | 1 | NO$_2$ | i-C$_3$H$_7$ | |
| 6.52 | 1 | NO$_2$ | n-C$_4$H$_9$ | |
| 6.53 | 1 | NO$_2$ | t-C$_4$H$_9$ | |
| 6.54 | 1 | NO$_2$ | cyclo-C$_3$H$_5$ | |
| 6.55 | 1 | NO$_2$ | CH$_2$C$_6$H$_5$ | |
| 6.56 | 1 | NO$_2$ | CH$_2$C$_6$H$_4$-4-CH$_3$ | |
| 6.57 | 1 | NO$_2$ | CH$_2$C$_6$H$_4$-4-OCH$_3$ | |
| 6.58 | 1 | NO$_2$ | CH$_2$C$_6$H$_4$-4-Cl | |
| 6.59 | 1 | NO$_2$ | CH$_2$C$_6$H$_4$-4-NO$_2$ | |
| 6.60 | 1 | NO$_2$ | CH$_2$-2-furyl | |
| 6.61 | 1 | NO$_2$ | CH$_2$-2-thienyl | |
| 6.62 | 1 | NO$_2$ | C$_6$H$_5$ | |
| 6.63 | 1 | NO$_2$ | C$_6$H$_4$-4-CH$_3$ | |
| 6.64 | 1 | NO$_2$ | C$_6$H$_4$-4-OCH$_3$ | |
| 6.65 | 1 | NO$_2$ | C$_6$H$_4$-4-Cl | |
| 6.66 | 1 | NO$_2$ | C$_6$H$_4$-4-NO$_2$ | |
| 6.67 | 1 | NO$_2$ | CH$_2$CH=CH$_2$ | |
| 6.68 | 1 | NO$_2$ | CH$_2$=CH | |
| 6.69 | 1 | NO$_2$ | CH$_2$CH=CHC$_6$H$_5$ | |
| 6.70 | 1 | NO$_2$ | CH$_2$C≡CC$_6$H$_5$ | |
| 6.71 | 2 | NO$_2$ | CH$_3$ | |
| 6.72 | 2 | NO$_2$ | C$_2$H$_5$ | |
| 6.73 | 2 | NO$_2$ | n-C$_3$H$_7$ | |
| 6.74 | 2 | NO$_2$ | i-C$_3$H$_7$ | |
| 6.75 | 2 | NO$_2$ | n-C$_4$H$_9$ | |
| 6.76 | 2 | NO$_2$ | t-C$_4$H$_9$ | |
| 6.77 | 2 | NO$_2$ | cyclo-C$_3$H$_5$ | |
| 6.78 | 2 | NO$_2$ | CH$_2$C$_6$H$_5$ | |
| 6.79 | 2 | NO$_2$ | CH$_2$C$_6$H$_4$-4-CH$_3$ | |
| 6.80 | 2 | NO$_2$ | CH$_2$C$_6$H$_4$-4-OCH$_3$ | |
| 6.81 | 2 | NO$_2$ | CH$_2$C$_6$H$_4$-4-Cl | |
| 6.82 | 2 | NO$_2$ | CH$_2$C$_6$H$_4$-4-NO$_2$ | |
| 6.83 | 2 | NO$_2$ | CH$_2$-2-furyl | |
| 6.84 | 2 | NO$_2$ | CH$_2$-2-thienyl | |
| 6.85 | 2 | NO$_2$ | C$_6$H$_5$ | |
| 6.86 | 2 | NO$_2$ | C$_6$H$_4$-4-CH$_3$ | |
| 6.87 | 2 | NO$_2$ | C$_6$H$_4$-4-OCH$_3$ | |
| 6.88 | 2 | NO$_2$ | C$_6$H$_4$-4-Cl | |
| 6.89 | 2 | NO$_2$ | C$_6$H$_4$-4-NO$_2$ | |
| 6.90 | 2 | NO$_2$ | CH$_2$CH=CH$_2$ | |

TABLE 6-continued

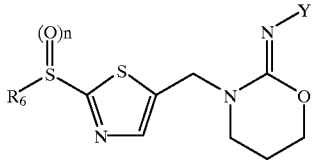

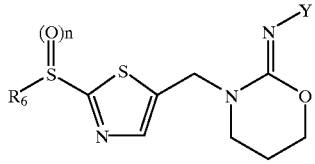

| Compound No. | n | Y | R_6 | Phys. data |
|---|---|---|---|---|
| 6.91 | 2 | $NO_2$ | $CH_2C\equiv CH$ | |
| 6.92 | 2 | $NO_2$ | $CH_2CH=CHC_6H_5$ | |
| 6.93 | 2 | $NO_2$ | $CH_2C\equiv CC_6H_5$ | |
| 6.94 | 0 | $NO_2$ | $CH_2SCH_3$ | |
| 6.95 | 0 | $NO_2$ | $CH_2SC_2H_5$ | |
| 6.96 | 0 | $NO_2$ | $CH_2S$-n-$C_3H_7$ | |
| 6.97 | 0 | $NO_2$ | $CH_2S$-i-$C_3H_7$ | |
| 6.98 | 0 | $NO_2$ | $CH_2S$-n-$C_4H_9$ | |
| 6.99 | 0 | $NO_2$ | $CH_2S$-t-$C_4H_9$ | |
| 6.100 | 0 | $NO_2$ | $CH_2S$-cyclo-$C_3H_5$ | |
| 6.101 | 0 | $NO_2$ | $CH_2SCH_2C_6H_5$ | |
| 6.102 | 0 | $NO_2$ | $CH_2SCH_2C_6H_4$-4-$CH_3$ | |
| 6.103 | 0 | $NO_2$ | $CH_2SCH_2C_6H_4$-4-$OCH_3$ | |
| 6.104 | 0 | $NO_2$ | $CH_2SCH_2C_6H_4$-4-Cl | |
| 6.105 | 0 | $NO_2$ | $CH_2SCH_2C_6H_4$-4-$NO_2$ | |
| 6.106 | 0 | $NO_2$ | $CH_2SCH_2$-2-furyl | |
| 6.107 | 0 | $NO_2$ | $CH_2SCH_2$-2-thienyl | |
| 6.108 | 0 | $NO_2$ | $CH_2SC_6H_5$ | |
| 6.109 | 0 | $NO_2$ | $CH_2SC_6H_4$-4-$CH_3$ | |
| 6.110 | 0 | $NO_2$ | $CH_2SC_6H_4$-4-$OCH_3$ | |
| 6.111 | 0 | $NO_2$ | $CH_2SC_6H_4$-4-Cl | |
| 6.112 | 0 | $NO_2$ | $CH_2SC_6H_4$-4-$NO_2$ | |
| 6.113 | 0 | $NO_2$ | $CH_2SCH_2CH=CH_2$ | |
| 6.114 | 0 | $NO_2$ | $CH_2SCH_2C\equiv CH$ | |
| 6.115 | 0 | $NO_2$ | $CH_2SCH_2CH=CHC_6H_5$ | |
| 6.116 | 0 | $NO_2$ | $CH_2SCH_2C\equiv CC_6H_5$ | |

6.117  0  $NO_2$

| 6.118 | 0 | CN | $CH_3$ | |
| 6.119 | 0 | CN | $C_2H_5$ | |
| 6.120 | 0 | CN | n-$C_3H_7$ | |
| 6.121 | 0 | CN | i-$C_3H_7$ | |
| 6.122 | 0 | CN | n-$C_4H_9$ | |
| 6.123 | 0 | CN | t-$C_4H_9$ | |
| 6.124 | 0 | CN | cyclo-$C_3H_5$ | |
| 6.125 | 0 | CN | $CH_2C_6H_5$ | |
| 6.126 | 0 | CN | $CH_2C_6H_4$-4-$CH_3$ | |
| 6.127 | 0 | CN | $CH_2C_6H_4$-4-$OCH_3$ | |
| 6.128 | 0 | CN | $CH_2C_6H_4$-4-Cl | |
| 6.129 | 0 | CN | $CH_2C_6H_4$-4-$NO_2$ | |
| 6.130 | 0 | CN | $CH_2$-2-furyl | |
| 6.131 | 0 | CN | $CH_2$-2-thienyl | |
| 6.132 | 0 | CN | $C_6H_5$ | |
| 6.133 | 0 | CN | $C_6H_4$-4-$CH_3$ | |
| 6.134 | 0 | CN | $C_6H_4$-4-$OCH_3$ | |
| 6.135 | 0 | CN | $C_6H_4$-4-Cl | |
| 6.136 | 0 | CN | $C_6H_4$-4-$NO_2$ | |
| 6.137 | 0 | CN | $CH_2CH=CH_2$ | |
| 6.138 | 0 | CN | $CH_2C\equiv CH$ | |
| 6.139 | 0 | CN | $CH_2CH=CHC_6H_5$ | |
| 6.140 | 0 | CN | $CH_2C\equiv CC_6H_5$ | |
| 6.141 | 0 | CN | $SCH_3$ | |
| 6.142 | 0 | CN | $SC_2H_5$ | |
| 6.143 | 0 | CN | S-n-$C_3H_7$ | |
| 6.144 | 0 | CN | S-i-$C_3H_7$ | |
| 6.145 | 0 | CN | S-n-$C_4H_9$ | |
| 6.146 | 0 | CN | S-t-$C_4H_9$ | |
| 6.147 | 0 | CN | S-cyclo-$C_3H_5$ | |
| 6.148 | 0 | CN | $SCH_2C_6H_5$ | |
| 6.149 | 0 | CN | $SCH_2C_6H_4$-4-$CH_3$ | |
| 6.150 | 0 | CN | $SCH_2C_6H_4$-4-$OCH_3$ | |
| 6.151 | 0 | CN | $SCH_2C_6H_4$-4-Cl | |
| 6.152 | 0 | CN | $SCH_2C_6H_4$-4-$NO_2$ | |
| 6.153 | 0 | CN | $SCH_2$-2-furyl | |
| 6.154 | 0 | CN | $SCH_2$-2-thienyl | |
| 6.155 | 0 | CN | $SC_6H_5$ | |
| 6.156 | 0 | CN | $SC_6H_4$-4-$CH_3$ | |
| 6.157 | 0 | CN | $SC_6H_4$-4-$OCH_3$ | |
| 6.158 | 0 | CN | $SC_6H_4$-4-Cl | |
| 6.159 | 0 | CN | $SC_6H_4$-4-$NO_2$ | |
| 6.160 | 0 | CN | $SCH_2CH=CH_2$ | |
| 6.161 | 0 | CN | $SCH_2C\equiv CH$ | |
| 6.162 | 0 | CN | $SCH_2CH=CHC_6H_5$ | |
| 6.163 | 0 | CN | $SCH_2C\equiv CC_6H_5$ | |

6.164  0  CN

| 6.165 | 1 | CN | $CH_3$ | |
| 6.166 | 1 | CN | $C_2H_5$ | |
| 6.167 | 1 | CN | n-$C_3H_7$ | |
| 6.168 | 1 | CN | i-$C_3H_7$ | |
| 6.169 | 1 | CN | n-$C_4H_9$ | |
| 6.170 | 1 | CN | t-$C_4H_9$ | |
| 6.171 | 1 | CN | cyclo-$C_3H_5$ | |
| 6.172 | 1 | CN | $CH_2C_6H_5$ | |
| 6.173 | 1 | CN | $CH_2C_6H_4$-4-$CH_3$ | |
| 6.174 | 1 | CN | $CH_2C_6H_4$-4-$OCH_3$ | |
| 6.175 | 1 | CN | $CH_2C_6H_4$-4-Cl | |
| 6.176 | 1 | CN | $CH_2C_6H_4$-4-$NO_2$ | |
| 6.177 | 1 | CN | $CH_2$-2-furyl | |
| 6.178 | 1 | CN | $CH_2$-2-thienyl | |
| 6.179 | 1 | CN | $C_6H_5$ | |
| 6.180 | 1 | CN | $C_6H_4$-4-$CH_3$ | |
| 6.181 | 1 | CN | $C_6H_4$-4-$OCH_3$ | |
| 6.182 | 1 | CN | $C_6H_4$-4-Cl | |
| 6.183 | 1 | CN | $C_6H_4$-4-$NO_2$ | |
| 6.184 | 1 | CN | $CH_2CH=CH_2$ | |
| 6.185 | 1 | CN | $CH_2C\equiv CH$ | |
| 6.186 | 1 | CN | $CH_2CH=CHC_6H_5$ | |
| 6.187 | 1 | CN | $CH_2C\equiv CC_6H_5$ | |
| 6.188 | 2 | CN | $CH_3$ | |
| 6.189 | 2 | CN | $C_2H_5$ | |
| 6.190 | 2 | CN | n-$C_3H_7$ | |
| 6.191 | 2 | CN | i-$C_3H_7$ | |
| 6.192 | 2 | CN | n-$C_4H_9$ | |
| 6.193 | 2 | CN | t-$C_4H_9$ | |
| 6.194 | 2 | CN | cyclo-$C_3H_5$ | |
| 6.195 | 2 | CN | $CH_2C_6H_5$ | |
| 6.196 | 2 | CN | $CH_2C_6H_4$-4-$CH_3$ | |
| 6.197 | 2 | CN | $CH_2C_6H_4$-4-$OCH_3$ | |
| 6.198 | 2 | CN | $CH_2C_6H_4$-4-Cl | |
| 6.199 | 2 | CN | $CH_2C_6H_4$-4-$NO_2$ | |
| 6.200 | 2 | CN | $CH_2$-2-furyl | |
| 6.201 | 2 | CN | $CH_2$-2-thienyl | |
| 6.202 | 2 | CN | $C_6H_5$ | |

TABLE 6-continued

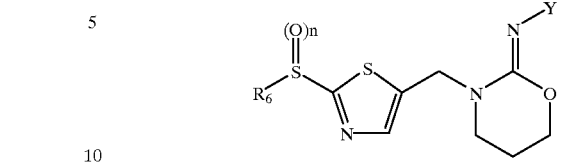

| Compound No. | n | Y | $R_6$ | Phys. data |
|---|---|---|---|---|
| 6.203 | 2 | CN | $C_6H_4$-4-$CH_3$ | |
| 6.204 | 2 | CN | $C_6H_4$-4-$OCH_3$ | |
| 6.205 | 2 | CN | $C_6H_4$-4-Cl | |
| 6.206 | 2 | CN | $C_6H_4$-4-$NO_2$ | |
| 6.207 | 2 | CN | $CH_2CH=CH_2$ | |
| 6.208 | 2 | CN | $CH_2C\equiv CH$ | |
| 6.209 | 2 | CN | $CH_2CH=CHC_6H_5$ | |
| 6.210 | 2 | CN | $CH_2C\equiv CC_6H_5$ | |
| 6.211 | 0 | CN | $CH_2SCH_3$ | |
| 6.212 | 0 | CN | $CH_2SC_2H_5$ | |
| 6.213 | 0 | CN | $CH_2S$-n-$C_3H_7$ | |
| 6.214 | 0 | CN | $CH_2S$-i-$C_3H_7$ | |
| 6.215 | 0 | CN | $CH_2S$-n-$C_4H_9$ | |
| 6.216 | 0 | CN | $CH_2S$-t-$C_4H_9$ | |
| 6.217 | 0 | CN | $CH_2S$-cyclo-$C_3H_5$ | |
| 6.218 | 0 | CN | $CH_2SCH_2C_6H_5$ | |
| 6.219 | 0 | CN | $CH_2SCH_2C_6H_4$-4-$CH_3$ | |
| 6.220 | 0 | CN | $CH_2SCH_2C_6H_4$-4-$OCH_3$ | |
| 6.221 | 0 | CN | $CH_2SCH_2C_6H_4$-4-Cl | |

TABLE 6-continued

| Compound No. | n | Y | $R_6$ | Phys. data |
|---|---|---|---|---|
| 6.222 | 0 | CN | $CH_2SCH_2C_6H_4$-4-$NO_2$ | |
| 6.223 | 0 | CN | $CH_2SCH_2$-2-furyl | |
| 6.224 | 0 | CN | $CH_2SCH_2$-2-thienyl | |
| 6.225 | 0 | CN | $CH_2SC_6H_5$ | |
| 6.226 | 0 | CN | $CH_2SC_6H_4$-4-$CH_3$ | |
| 6.227 | 0 | CN | $CH_2SC_6H_4$-4-$OCH_3$ | |
| 6.228 | 0 | CN | $CH_2SC_6H_4$-4-Cl | |
| 6.229 | 0 | CN | $CH_2SC_6H_4$-4-$NO_2$ | |
| 6.230 | 0 | CN | $CH_2SCH_2CH=CH_2$ | |
| 6.231 | 0 | CN | $CH_2SCH_2C\equiv CH$ | |
| 6.232 | 0 | CN | $CH_2SCH_2CH=CHC_6H_5$ | |
| 6.233 | 0 | CN | $CH_2SCH_2C\equiv CC_6H_5$ | |
| 6.234 | 0 | CN | 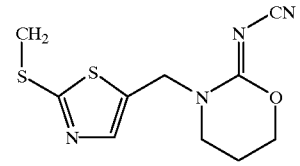 | |

TABLE 7

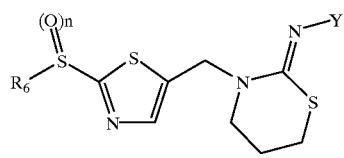

| Compound No. | n | Y | $R_6$ | Phys. data |
|---|---|---|---|---|
| 7.1 | 0 | $NO_2$ | $CH_3$ | |
| 7.2 | 0 | $NO_2$ | $C_2H_5$ | |
| 7.3 | 0 | $NO_2$ | n-$C_3H_7$ | |
| 7.4 | 0 | $NO_2$ | i-$C_3H_7$ | |
| 7.5 | 0 | $NO_2$ | n-$C_4H_9$ | |
| 7.6 | 0 | $NO_2$ | t-$C_4H_9$ | |
| 7.7 | 0 | $NO_2$ | cyclo-$C_3H_5$ | |
| 7.8 | 0 | $NO_2$ | $CH_2C_6H_5$ | |
| 7.9 | 0 | $NO_2$ | $CH_2C_6H_4$-4-$CH_3$ | |
| 7.10 | 0 | $NO_2$ | $CH_2CH_4$-4-$OCH_3$ | |
| 7.11 | 0 | $NO_2$ | $CH_2C_6H_4$-4-Cl | |
| 7.12 | 0 | $NO_2$ | $CH_2C_6H_4$-4-$NO_2$ | |
| 7.13 | 0 | $NO_2$ | $CH_2$-2-furyl | |
| 7.14 | 0 | $NO_2$ | $CH_2$-2-thienyl | |
| 7.15 | 0 | $NO_2$ | $C_6H_5$ | |
| 7.16 | 0 | $NO_2$ | $C_6H_4$-4-$CH_3$ | |
| 7.17 | 0 | $NO_2$ | $C_6H_4$-4-$OCH_3$ | |

TABLE 7-continued

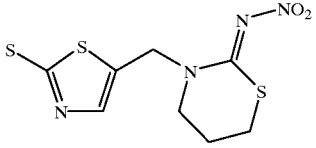

| Compound No. | n | Y | $R_6$ | Phys. data |
|---|---|---|---|---|
| 7.18 | 0 | $NO_2$ | $C_6H_4$-4-Cl | |
| 7.19 | 0 | $NO_2$ | $C_6H_4$-4-$NO_2$ | |
| 7.20 | 0 | $NO_2$ | $CH_2CH=CH_2$ | |
| 7.21 | 0 | $NO_2$ | $CH_2C\equiv CH$ | |
| 7.22 | 0 | $NO_2$ | $CH_2CH=CHC_6H_5$ | |
| 7.23 | 0 | $NO_2$ | $CH_2C\equiv CC_6H_5$ | |
| 7.24 | 0 | $NO_2$ | $SCH_3$ | |
| 7.25 | 0 | $NO_2$ | $SC_2H_5$ | |
| 7.26 | 0 | $NO_2$ | S-n-$C_3H_7$ | |
| 7.27 | 0 | $NO_2$ | S-i-$C_3H_7$ | |
| 7.28 | 0 | $NO_2$ | S-n-$C_4H_9$ | |
| 7.29 | 0 | $NO_2$ | S-t-$C_4H_9$ | |
| 7.30 | 0 | $NO_2$ | S-cyclo-$C_3H_5$ | |
| 7.31 | 0 | $NO_2$ | $SCH_2C_6H_5$ | |
| 7.32 | 0 | $NO_2$ | $SCH_2C_6H_4$-4-$CH_3$ | |
| 7.33 | 0 | $NO_2$ | $SCH_2C_6H_4$-4-$OCH_3$ | |
| 7.34 | 0 | $NO_2$ | $SCH_2C_6H_4$-4-Cl | |
| 7.35 | 0 | $NO_2$ | $SCH_2C_6H_4$-4-$NO_2$ | |
| 7.36 | 0 | $NO_2$ | $SCH_2$-2-furyl | |
| 7.37 | 0 | $NO_2$ | $SCH_2$-2-thienyl | |
| 7.38 | 0 | $NO_2$ | $SC_6H_5$ | |
| 7.39 | 0 | $NO_2$ | $SC_6H_4$-4-$CH_3$ | |
| 7.40 | 0 | $NO_2$ | $SC_6H_4$-4-$OCH_3$ | |
| 7.41 | 0 | $NO_2$ | $SC_6H_4$-4-Cl | |
| 7.42 | 0 | $NO_2$ | $SC_6H_4$-4-$NO_2$ | |
| 7.43 | 0 | $NO_2$ | $SCH_2CH=CH_2$ | |
| 7.44 | 0 | $NO_2$ | $SCH_2C\equiv CH$ | |
| 7.45 | 0 | $NO_2$ | $SCH_2CH=CHC_6H_5$ | |
| 7.46 | 0 | $NO_2$ | $SCH_2C\equiv CC_6H_5$ | |
| 7.47 | 0 | $NO_2$ | | |
| 7.48 | 1 | $NO_2$ | $CH_3$ | |
| 7.49 | 1 | $NO_2$ | $C_2H_5$ | |
| 7.50 | 1 | $NO_2$ | n-$C_3H_7$ | |
| 7.51 | 1 | $NO_2$ | i-$C_3H_7$ | |
| 7.52 | 1 | $NO_2$ | n-$C_4H_9$ | |
| 7.53 | 1 | $NO_2$ | t-$C_4H_9$ | |
| 7.54 | 1 | $NO_2$ | cyclo-$C_3H_5$ | |
| 7.55 | 1 | $NO_2$ | $CH_2C_6H_5$ | |
| 7.56 | 1 | $NO_2$ | $CH_2C_6H_4$-4-$CH_3$ | |
| 7.57 | 1 | $NO_2$ | $CH_2C_6H_4$-4-$OCH_3$ | |
| 7.58 | 1 | $NO_2$ | $CH_2C_6H_4$-4-Cl | |
| 7.59 | 1 | $NO_2$ | $CH_2C_6H_4$-4-$NO_2$ | |
| 7.60 | 1 | $NO_2$ | $CH_2$-2-furyl | |
| 7.61 | 1 | $NO_2$ | $CH_2$-2-thienyl | |
| 7.62 | 1 | $NO_2$ | $C_6H_5$ | |
| 7.63 | 1 | $NO_2$ | $C_6H_4$-4-$CH_3$ | |
| 7.64 | 1 | $NO_2$ | $C_6H_4$-4-$OCH_3$ | |
| 7.65 | 1 | $NO_2$ | $C_6H_4$-4-Cl | |
| 7.66 | 1 | $NO_2$ | $C_6H_4$-4-$NO_2$ | |
| 7.67 | 1 | $NO_2$ | $CH_2CH=CH_2$ | |
| 7.68 | 1 | $NO_2$ | $CH_2C\equiv CH$ | |
| 7.69 | 1 | $NO_2$ | $CH_2CH=CHC_6H_5$ | |
| 7.70 | 1 | $NO_2$ | $CH_2C\equiv CC_6H_5$ | |
| 7.71 | 2 | $NO_2$ | $CH_3$ | |
| 7.72 | 2 | $NO_2$ | $C_2H_5$ | |
| 7.73 | 2 | $NO_2$ | n-$C_3H_7$ | |
| 7.74 | 2 | $NO_2$ | i-$C_3H_7$ | |
| 7.75 | 2 | $NO_2$ | n-$C_4H_9$ | |
| 7.76 | 2 | $NO_2$ | t-$C_4H_9$ | |

TABLE 7-continued

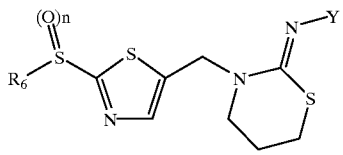

| Compound No. | n | Y | $R_6$ | Phys. data |
|---|---|---|---|---|
| 7.77 | 2 | $NO_2$ | cyclo-$C_3H_5$ | |
| 7.78 | 2 | $NO_2$ | $CH_2C_6H_5$ | |
| 7.79 | 2 | $NO_2$ | $CH_2C_6H_4$-4-$CH_3$ | |
| 7.80 | 2 | $NO_2$ | $CH_2C_6H_4$-4-$OCH_3$ | |
| 7.81 | 2 | $NO_2$ | $CH_2C_6H_4$-4-Cl | |
| 7.82 | 2 | $NO_2$ | $CH_2C_6H_4$-4-$NO_2$ | |
| 7.83 | 2 | $NO_2$ | $CH_2$-2-furyl | |
| 7.84 | 2 | $NO_2$ | $CH_2$-2-thienyl | |
| 7.85 | 2 | $NO_2$ | $C_6H_5$ | |
| 7.86 | 2 | $NO_2$ | $C_6H_4$-4-$CH_3$ | |
| 7.87 | 2 | $NO_2$ | $C_6H_4$-4-$OCH_3$ | |
| 7.88 | 2 | $NO_2$ | $C_6H_4$-4-Cl | |
| 7.89 | 2 | $NO_2$ | $C_6H_4$-4-$NO_2$ | |
| 7.90 | 2 | $NO_2$ | $CH_2CH=CH_2$ | |
| 7.91 | 2 | $NO_2$ | $CH_2C\equiv CH$ | |
| 7.92 | 2 | $NO_2$ | $CH_2CH=CHC_6H_5$ | |
| 7.93 | 2 | $NO_2$ | $CH_2C\equiv CC_6H_5$ | |
| 7.94 | 0 | $NO_2$ | $CH_2SCH_3$ | |
| 7.95 | 0 | $NO_2$ | $CH_2SC_2H_5$ | |
| 7.96 | 0 | $NO_2$ | $CH_2$-S-n-$C_3H_7$ | |
| 7.97 | 0 | $NO_2$ | $CH_2$-S-i-$C_3H_7$ | |
| 7.98 | 0 | $NO_2$ | $CH_2$-S-n-$C_4H_9$ | |
| 7.99 | 0 | $NO_2$ | $CH_2$-S-t-$C_4H_9$ | |
| 7.100 | 0 | $NO_2$ | $CH_2$-S-cyclo-$C_3H_5$ | |
| 7.101 | 0 | $NO_2$ | $CH_2SCH_2C_6H_5$ | |
| 7.102 | 0 | $NO_2$ | $CH_2SCH_2C_6H_4$-4-$CH_3$ | |
| 7.103 | 0 | $NO_2$ | $CH_2SCH_2C_6H_4$-4-$OCH_3$ | |
| 7.104 | 0 | $NO_2$ | $CH_2SCH_2C_6H_4$-4-Cl | |
| 7.105 | 0 | $NO_2$ | $CH_2SCH_2C_6H_4$-4-$NO_2$ | |
| 7.106 | 0 | $NO_2$ | $CH_2SCH_2$-2-furyl | |
| 7.107 | 0 | $NO_2$ | $CH_2SCH_2$-2-thienyl | |
| 7.108 | 0 | $NO_2$ | $CH_2SC_6H_5$ | |
| 7.109 | 0 | $NO_2$ | $CH_2SC_6H_4$-4-$CH_3$ | |
| 7.110 | 0 | $NO_2$ | $CH_2SC_6H_4$-4-$OCH_3$ | |
| 7.111 | 0 | $NO_2$ | $CH_2SC_6H_4$-4-Cl | |
| 7.112 | 0 | $NO_2$ | $CH_2SC_6H_4$-4-$NO_2$ | |
| 7.113 | 0 | $NO_2$ | $CH_2SCH_2CH=CH_2$ | |
| 7.114 | 0 | $NO_2$ | $CH_2SCH_2C\equiv CH$ | |
| 7.115 | 0 | $NO_2$ | $CH_2SCH_2CH=CHC_6H_5$ | |
| 7.116 | 0 | $NO_2$ | $CH_2SCH_2C\equiv CC_6H_5$ | |
| 7.117 | 0 | $NO_2$ | | |
| 7.118 | 0 | CN | $CH_3$ | |
| 7.119 | 0 | CN | $C_2H_5$ | |
| 7.120 | 0 | CN | n-$C_3H_7$ | |
| 7.121 | 0 | CN | i-$C_3H_7$ | |
| 7.122 | 0 | CN | n-$C_4H_9$ | |
| 7.123 | 0 | CN | t-$C_4H_9$ | |
| 7.124 | 0 | CN | cyclo-$C_3H_5$ | |
| 7.125 | 0 | CN | $CH_2C_6H_5$ | |
| 7.126 | 0 | CN | $CH_2C_6H_4$-4-$CH_3$ | |
| 7.127 | 0 | CN | $CH_2C_6H_4$-4-$OCH_3$ | |
| 7.128 | 0 | CN | $CH_2C_6H_4$-4-Cl | |
| 7.129 | 0 | CN | $CH_2C_6H_4$-4-$NO_2$ | |
| 7.130 | 0 | CN | $CH_2$-2-furyl | |
| 7.131 | 0 | CN | $CH_2$-2-thienyl | |
| 7.132 | 0 | CN | $C_6H_5$ | |
| 7.133 | 0 | CN | $C_6H_4$-4-$CH_3$ | |
| 7.134 | 0 | CN | $C_6H_4$-4-$OCH_3$ | |
| 7.135 | 0 | CN | $C_6H_4$-4-Cl | |
| 7.136 | 0 | CN | $C_6H_4$-4-$NO_2$ | |

TABLE 7-continued

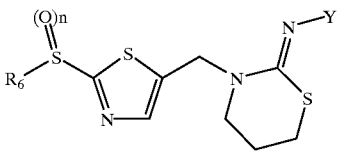

| Compound No. | n | Y | R$_6$ | Phys. data |
|---|---|---|---|---|
| 7.137 | 0 | CN | CH$_2$CH=CH$_2$ | |
| 7.138 | 0 | CN | CH$_2$C≡CH | |
| 7.139 | 0 | CN | CH$_2$CH=CHC$_6$H$_5$ | |
| 7.140 | 0 | CN | CH$_2$C≡CC$_6$H$_5$ | |
| 7.141 | 0 | CN | SCH$_3$ | |
| 7.142 | 0 | CN | SC$_2$H$_5$ | |
| 7.143 | 0 | CN | S-n-C$_3$H$_7$ | |
| 7.144 | 0 | CN | S-i-C$_3$H$_7$ | |
| 7.145 | 0 | CN | S-n-C$_4$H$_9$ | |
| 7.146 | 0 | CN | S-t-C$_4$H$_9$ | |
| 7.147 | 0 | CN | S-cyclo-C$_3$H$_5$ | |
| 7.148 | 0 | CN | SCH$_2$C$_6$H$_5$ | |
| 7.149 | 0 | CN | SCH$_2$C$_6$H$_4$-4-CH$_3$ | |
| 7.150 | 0 | CN | SCH$_2$C$_6$H$_4$-4-OCH$_3$ | |
| 7.151 | 0 | CN | SCH$_2$C$_6$H$_4$-4-Cl | |
| 7.152 | 0 | CN | SCH$_2$C$_6$H$_4$-4-NO$_2$ | |
| 7.153 | 0 | CN | SCH$_2$-2-furyl | |
| 7.154 | 0 | CN | SCH$_2$-2-thienyl | |
| 7.155 | 0 | CN | SC$_6$H$_5$ | |
| 7.156 | 0 | CN | SC$_6$H$_4$-4-CH$_3$ | |
| 7.157 | 0 | CN | SC$_6$H$_4$-4-OCH$_3$ | |
| 7.158 | 0 | CN | SC$_6$H$_4$-4-Cl | |
| 7.159 | 0 | CN | SC$_6$H$_4$-4-NO$_2$ | |
| 7.160 | 0 | CN | SCH$_2$CH=CH$_2$ | |
| 7.161 | 0 | CN | SCH$_2$C≡CH | |
| 7.162 | 0 | CN | SCH$_2$CH=CHC$_6$H$_5$ | |
| 7.163 | 0 | CN | SCH$_2$C≡CC$_6$H$_5$ | |
| 7.164 | 0 | CN | | |
| 7.165 | 1 | CN | CH$_3$ | |
| 7.166 | 1 | CN | C$_2$H$_5$ | |
| 7.167 | 1 | CN | n-C$_3$H$_7$ | |
| 7.168 | 1 | CN | i-C$_3$H$_7$ | |
| 7.169 | 1 | CN | n-C$_4$H$_9$ | |
| 7.170 | 1 | CN | t-C$_4$H$_9$ | |
| 7.171 | 1 | CN | cyclo-C$_3$H$_5$ | |
| 7.172 | 1 | CN | CH$_2$C$_6$H$_5$ | |
| 7.173 | 1 | CN | CH$_2$C$_6$H$_4$-4-CH$_3$ | |
| 7.174 | 1 | CN | CH$_2$C$_6$H$_4$-4-OCH$_3$ | |
| 7.175 | 1 | CN | CH$_2$C$_6$H$_4$-4-Cl | |
| 7.176 | 1 | CN | CH$_2$C$_6$H$_4$-4-NO$_2$ | |
| 7.177 | 1 | CN | CH$_2$-2-furyl | |
| 7.178 | 1 | CN | CH$_2$-2-thienyl | |
| 7.179 | 1 | CN | C$_6$H$_5$ | |
| 7.180 | 1 | CN | C$_6$H$_4$-4-CH$_3$ | |
| 7.181 | 1 | CN | C$_6$H$_4$-4-OCH$_3$ | |
| 7.182 | 1 | CN | C$_6$H$_4$-4-Cl | |
| 7.183 | 1 | CN | C$_6$H$_4$-4-NO$_2$ | |
| 7.184 | 1 | CN | CH$_2$CH=CH$_2$ | |
| 7.185 | 1 | CN | CH$_2$C≡CH | |
| 7.186 | 1 | CN | CH$_2$CH=CHC$_6$H$_5$ | |
| 7.187 | 1 | CN | CH$_2$C≡CC$_6$H$_5$ | |
| 7.188 | 2 | CN | CH$_3$ | |
| 7.189 | 2 | CN | C$_2$H$_5$ | |
| 7.190 | 2 | CN | n-C$_3$H$_7$ | |
| 7.191 | 2 | CN | i-C$_3$H$_7$ | |
| 7.192 | 2 | CN | n-C$_4$H$_9$ | |
| 7.193 | 2 | CN | t-C$_4$H$_9$ | |
| 7.194 | 2 | CN | cyclo-C$_3$H$_5$ | |
| 7.195 | 2 | CN | CH$_2$C$_6$H$_5$ | |
| 7.196 | 2 | CN | CH$_2$C$_6$H$_4$-4-CH$_3$ | |

TABLE 7-continued

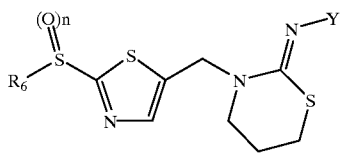

| Compound No. | n | Y | R$_6$ | Phys. data |
|---|---|---|---|---|
| 7.197 | 2 | CN | CH$_2$C$_6$H$_4$-4-OCH$_3$ | |
| 7.198 | 2 | CN | CH$_2$C$_6$H$_4$-4-Cl | |
| 7.199 | 2 | CN | CH$_2$C$_6$H$_4$-4-NO$_2$ | |
| 7.200 | 2 | CN | CH$_2$-2-furyl | |
| 7.201 | 2 | CN | CH$_2$-2-thienyl | |
| 7.202 | 2 | CN | C$_6$H$_5$ | |
| 7.203 | 2 | CN | C$_6$H$_4$-4-CH$_3$ | |
| 7.204 | 2 | CN | C$_6$H$_4$-4-OCH$_3$ | |
| 7.205 | 2 | CN | C$_6$H$_4$-4-Cl | |
| 7.206 | 2 | CN | C$_6$H$_4$-4-NO$_2$ | |
| 7.207 | 2 | CN | CH$_2$CH=CH$_2$ | |
| 7.208 | 2 | CN | CH$_2$C≡CH | |
| 7.209 | 2 | CN | CH$_2$CH=CHC$_6$H$_5$ | |
| 7.210 | 2 | CN | CH$_2$C≡CC$_6$H$_5$ | |
| 7.211 | 0 | CN | CH$_2$SCH$_3$ | |
| 7.212 | 0 | CN | CH$_2$SC$_2$H$_5$ | |
| 7.213 | 0 | CN | CH$_2$S-n-C$_3$H$_7$ | |
| 7.214 | 0 | CN | CH$_2$S-i-C$_3$H$_7$ | |
| 7.215 | 0 | CN | CH$_2$S-n-C$_4$H$_9$ | |
| 7.216 | 0 | CN | CH$_2$S-t-C$_4$H$_9$ | |
| 7.217 | 0 | CN | CH$_2$S-cyclo-C$_3$H$_5$ | |
| 7.218 | 0 | CN | CH$_2$SCH$_2$C$_6$H$_5$ | |
| 7.219 | 0 | CN | CH$_2$SCH$_2$C$_6$H$_4$-4-CH$_3$ | |
| 7.220 | 0 | CN | CH$_2$SCH$_2$C$_6$H$_4$-4-OCH$_3$ | |
| 7.221 | 0 | CN | CH$_2$SCH$_2$C$_6$H$_4$-4-Cl | |
| 7.222 | 0 | CN | CH$_2$SCH$_2$C$_6$H$_4$-4-NO$_2$ | |
| 7.223 | 0 | CN | CH$_2$SCH$_2$-2-furyl | |
| 7.224 | 0 | CN | CH$_2$SCH$_2$-2-thienyl | |
| 7.225 | 0 | CN | CH$_2$SC$_6$H$_5$ | |
| 7.226 | 0 | CN | CH$_2$SC$_6$H$_4$-4-CH$_3$ | |
| 7.227 | 0 | CN | CH$_2$SC$_6$H$_4$-4-OCH$_3$ | |
| 7.228 | 0 | CN | CH$_2$SC$_6$H$_4$-4-Cl | |
| 7.229 | 0 | CN | CH$_2$SC$_6$H$_4$-4-NO$_2$ | |
| 7.230 | 0 | CN | CH$_2$SCH$_2$CH=CH$_2$ | |
| 7.231 | 0 | CN | CH$_2$SCH$_2$C≡CH | |
| 7.232 | 0 | CN | CH$_2$SCH$_2$CH=CHC$_6$H$_5$ | |
| 7.233 | 0 | CN | CH$_2$SCH$_2$C≡CC$_6$H$_5$ | |
| 7.234 | 0 | CN | (structure) | |

TABLE 8

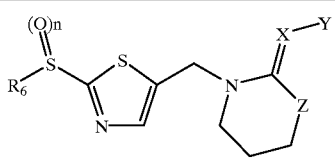

| Compound No. | n | X | Y | Z | R$_6$ | Physical data |
|---|---|---|---|---|---|---|
| 8.1 | 0 | N | NO$_2$ | NH | i-C$_3$H$_7$ | |
| 8.2 | 0 | N | NO$_2$ | NH | CH$_3$ | |
| 8.3 | 0 | N | NO$_2$ | NH | CH$_2$CO$_2$CO$_2$H$_5$ | |
| 8.4 | 0 | N | NO$_2$ | NH | CH$_2$C$_6$H$_5$ | |
| 8.5 | 0 | N | NO$_2$ | NH | CH$_2$C$_6$H$_4$-4-Cl | |

TABLE 8-continued

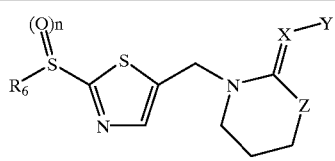

| Compound No. | n | X | Y | Z | R$_6$ | Physical data |
|---|---|---|---|---|---|---|
| 8.6 | 0 | N | NO$_2$ | NH | C$_6$H$_5$ | |
| 8.7 | 0 | N | NO$_2$ | NH | C$_6$H$_4$-4-Cl | |
| 8.8 | 0 | N | NO$_2$ | NH | CH$_2$CH=CH$_2$ | |
| 8.9 | 0 | N | NO$_2$ | NH | CH$_2$C≡CH | |
| 8.10 | 0 | N | NO$_2$ | NH | SCH$_3$ | |

TABLE 8-continued

| Compound No. | n | X | Y | Z | R$_6$ | Physical data |
|---|---|---|---|---|---|---|
| 8.11 | 0 | N | NO$_2$ | NH | SC$_2$H$_5$ | |
| 8.12 | 0 | N | NO$_2$ | NH | S-n-C$_3$H$_7$ | |
| 8.13 | 0 | N | NO$_2$ | NH | S-i-C$_3$H$_7$ | |
| 8.14 | 0 | N | NO$_2$ | NH | SCH$_2$C$_6$H$_5$ | |
| 8.15 | 1 | N | NO$_2$ | NH | i-C$_3$H$_7$ | |
| 8.16 | 1 | N | NO$_2$ | NH | CH$_2$C$_6$H$_5$ | |
| 8.17 | 2 | N | NO$_2$ | NH | i-C$_3$H$_7$ | |
| 8.18 | 2 | N | NO$_2$ | NH | CH$_2$C$_6$H$_5$ | |
| 8.19 | 0 | N | CN | NH | i-C$_3$H$_7$ | |
| 8.20 | 0 | N | CN | NH | CH$_3$ | |
| 8.21 | 0 | N | CN | NH | CH$_2$CO$_2$C$_2$H$_5$ | |
| 8.22 | 0 | N | CN | NH | CH$_2$C$_6$H$_5$ | |
| 8.23 | 0 | N | CN | NH | CH$_2$C$_6$H$_4$-4-Cl | |
| 8.24 | 0 | N | CN | NH | C$_6$H$_5$ | |
| 8.25 | 0 | N | CN | NH | C$_6$H$_4$-4-Cl | |
| 8.26 | 0 | N | CN | NH | CH$_2$CH=CH$_2$ | |
| 8.27 | 0 | N | CN | NH | CH$_2$C≡CH | |
| 8.28 | 0 | N | CN | NH | SCH$_3$ | |
| 8.29 | 0 | N | CN | NH | SC$_2$H$_5$ | |
| 8.30 | 0 | N | CN | NH | S-n-C$_3$H$_7$ | |
| 8.31 | 0 | N | CN | NH | S-i-C$_3$H$_7$ | |
| 8.32 | 0 | N | CN | NH | SCH$_2$C$_6$H$_5$ | |
| 8.33 | 1 | N | CN | NH | i-C$_3$H$_7$ | |
| 8.34 | 1 | N | CN | NH | CH$_2$C$_6$H$_5$ | |
| 8.35 | 2 | N | CN | NH | i-C$_3$H$_7$ | |
| 8.36 | 2 | N | CN | NH | CH$_2$C$_6$H$_5$ | |
| 8.37 | 0 | CH | NO$_2$ | NH | i-C$_3$H$_7$ | |
| 8.38 | 0 | CH | NO$_2$ | NH | CH$_3$ | |
| 8.39 | 0 | CH | NO$_2$ | NH | CH$_2$CO$_2$C$_2$H$_5$ | |
| 8.40 | 0 | CH | NO$_2$ | NH | CH$_2$C$_6$H$_5$ | |
| 8.41 | 0 | CH | NO$_2$ | NH | CH$_2$C$_6$H$_4$-4-Cl | |
| 8.42 | 0 | CH | NO$_2$ | NH | C$_6$H$_5$ | |
| 8.43 | 0 | CH | NO$_2$ | NH | C$_6$H$_4$-4-Cl | |
| 8.44 | 0 | CH | NO$_2$ | NH | CH$_2$CH=CH$_2$ | |
| 8.45 | 0 | CH | NO$_2$ | NH | CH$_2$C≡CH | |
| 8.46 | 0 | CH | NO$_2$ | NH | SCH$_3$ | |
| 8.47 | 0 | CH | NO$_2$ | NH | SC$_2$H$_5$ | |
| 8.48 | 0 | CH | NO$_2$ | NH | S-n-C$_3$H$_7$ | |
| 8.49 | 0 | CH | NO$_2$ | NH | S-i-C$_3$H$_7$ | |
| 8.50 | 0 | CH | NO$_2$ | NH | SCH$_2$C$_6$H$_5$ | |
| 8.51 | 1 | CH | NO$_2$ | NH | i-C$_3$H$_7$ | |
| 8.52 | 1 | CH | NO$_2$ | NH | CH$_2$C$_6$H$_5$ | |
| 8.53 | 2 | CH | NO$_2$ | NH | i-C$_3$H$_7$ | |
| 8.54 | 2 | CH | NO$_2$ | NH | CH$_2$C$_6$H$_5$ | |
| 8.55 | 0 | N | NO$_2$ | N-CH$_3$ | i-C$_3$H$_7$ | |
| 8.56 | 0 | N | NO$_2$ | N-CH$_3$ | CH$_3$ | |
| 8.57 | 0 | N | NO$_2$ | N-CH$_3$ | CH$_2$CO$_2$C$_2$H$_5$ | |
| 8.58 | 0 | N | NO$_2$ | N-CH$_3$ | CH$_2$C$_6$H$_5$ | |
| 8.59 | 0 | N | NO$_2$ | N-CH$_3$ | CH$_2$C$_6$H$_4$-4-Cl | |
| 8.60 | 0 | N | NO$_2$ | N-CH$_3$ | C$_6$H$_5$ | |
| 8.61 | 0 | N | NO$_2$ | N-CH$_3$ | C$_6$H$_4$-4-Cl | |
| 8.62 | 0 | N | NO$_2$ | N-CH$_3$ | CH$_2$CH=CH$_2$ | |
| 8.63 | 0 | N | NO$_2$ | N-CH$_3$ | CH$_2$C≡CH | |
| 8.64 | 0 | N | NO$_2$ | N-CH$_3$ | SCH$_3$ | |
| 8.65 | 0 | N | NO$_2$ | N-CH$_3$ | SC$_2$H$_5$ | |
| 8.66 | 0 | N | NO$_2$ | N-CH$_3$ | S-n-C$_3$H$_7$ | |
| 8.67 | 0 | N | NO$_2$ | N-CH$_3$ | S-i-C$_3$H$_7$ | |
| 8.68 | 0 | N | NO$_2$ | N-CH$_3$ | SCH$_2$C$_6$H$_5$ | |
| 8.69 | 1 | N | NO$_2$ | N-CH$_3$ | i-C$_3$H$_7$ | |
| 8.70 | 1 | N | NO$_2$ | N-CH$_3$ | CH$_2$C$_6$H$_5$ | |
| 8.71 | 2 | N | NO$_2$ | N-CH$_3$ | i-C$_3$H$_7$ | |
| 8.72 | 2 | N | NO$_2$ | N-CH$_3$ | CH$_2$C$_6$H$_5$ | |
| 8.73 | 0 | N | CN | N-CH$_3$ | i-C$_3$H$_7$ | |
| 8.74 | 0 | N | CN | N-CH$_3$ | CH$_3$ | |
| 8.75 | 0 | N | CN | N-CH$_3$ | CH$_2$CO$_2$C$_2$H$_5$ | |
| 8.76 | 0 | N | CN | N-CH$_3$ | CH$_2$C$_6$H$_5$ | |
| 8.77 | 0 | N | CN | N-CH$_3$ | CH$_2$C$_6$H$_4$-4-Cl | |
| 8.78 | 0 | N | CN | N-CH$_3$ | C$_6$H$_5$ | |
| 8.79 | 0 | N | CN | N-CH$_3$ | C$_6$H$_4$-4-Cl | |
| 8.80 | 0 | N | CN | N-CH$_3$ | CH$_2$CH=CH$_2$ | |
| 8.81 | 0 | N | CN | N-CH$_3$ | CH$_2$C≡CH | |
| 8.82 | 0 | N | CN | N-CH$_3$ | SCH$_3$ | |
| 8.83 | 0 | N | CN | N-CH$_3$ | SC$_2$H$_5$ | |
| 8.84 | 0 | N | CN | N-CH$_3$ | S-n-C$_3$H$_7$ | |
| 8.85 | 0 | N | CN | N-CH$_3$ | S-i-C$_3$H$_7$ | |
| 8.86 | 0 | N | CN | N-CH$_3$ | SCH$_2$C$_6$H$_5$ | |
| 8.87 | 1 | N | CN | N-CH$_3$ | i-C$_3$H$_7$ | |
| 8.88 | 1 | N | CN | N-CH$_3$ | CH$_2$C$_6$H$_5$ | |
| 8.89 | 2 | N | CN | N-CH$_3$ | i-C$_3$H$_7$ | |
| 8.90 | 2 | N | CN | N-CH$_3$ | CH$_2$C$_6$H$_5$ | |
| 8.91 | 0 | CH | NO$_2$ | N-CH$_3$ | i-C$_3$H$_7$ | |
| 8.92 | 0 | CH | NO$_2$ | N-CH$_3$ | CH$_3$ | |
| 8.93 | 0 | CH | NO$_2$ | N-CH$_3$ | CH$_2$CO$_2$C$_2$H$_5$ | |
| 8.94 | 0 | CH | NO$_2$ | N-CH$_3$ | CH$_2$C$_6$H$_5$ | |
| 8.95 | 0 | CH | NO$_2$ | N-CH$_3$ | CH$_2$C$_6$H$_4$-4-Cl | |
| 8.96 | 0 | CH | NO$_2$ | N-CH$_3$ | C$_6$H$_5$ | |
| 8.97 | 0 | CH | NO$_2$ | N-CH$_3$ | C$_6$H$_4$-4-Cl | |
| 8.98 | 0 | CH | NO$_2$ | N-CH$_3$ | CH$_2$CH=CH$_2$ | |
| 8.99 | 0 | CH | NO$_2$ | N-CH$_3$ | CH$_2$C≡CH | |
| 8.100 | 0 | CH | NO$_2$ | N-CH$_3$ | SCH$_3$ | |
| 8.101 | 0 | CH | NO$_2$ | N-CH$_3$ | SC$_2$H$_5$ | |
| 8.102 | 0 | CH | NO$_2$ | N-CH$_3$ | S-n-C$_3$H$_7$ | |
| 8.103 | 0 | CH | NO$_2$ | N-CH$_3$ | S-i-C$_3$H$_7$ | |
| 8.104 | 0 | CH | NO$_2$ | N-CH$_3$ | SCH$_2$C$_6$H$_5$ | |
| 8.105 | 1 | CH | NO$_2$ | N-CH$_3$ | i-C$_3$H$_7$ | |
| 8.106 | 1 | CH | NO$_2$ | N-CH$_3$ | CH$_2$C$_6$H$_5$ | |
| 8.107 | 2 | CH | NO$_2$ | N-CH$_3$ | i-C$_3$H$_7$ | |
| 8.108 | 2 | CH | NO$_2$ | N-CH$_3$ | CH$_2$C$_6$H$_5$ | |
| 8.109 | 0 | N | NO$_2$ | CH$_2$ | i-C$_3$H$_7$ | |
| 8.110 | 0 | N | NO$_2$ | CH$_2$ | CH$_3$ | |
| 8.111 | 0 | N | NO$_2$ | CH$_2$ | CH$_2$CO$_2$C$_2$H$_5$ | |
| 8.112 | 0 | N | NO$_2$ | CH$_2$ | CH$_2$C$_6$H$_5$ | |
| 8.113 | 0 | N | NO$_2$ | CH$_2$ | CH$_2$C$_6$H$_4$-4-Cl | |
| 8.114 | 0 | N | NO$_2$ | CH$_2$ | C$_6$H$_5$ | |
| 8.115 | 0 | N | NO$_2$ | CH$_2$ | C$_6$H$_4$-4-Cl | |
| 8.116 | 0 | N | NO$_2$ | CH$_2$ | CH$_2$CH=CH$_2$ | |
| 8.117 | 0 | N | NO$_2$ | CH$_2$ | CH$_2$C≡CH | |
| 8.118 | 0 | N | NO$_2$ | CH$_2$ | SCH$_3$ | |
| 8.119 | 0 | N | NO$_2$ | CH$_2$ | SC$_2$H$_5$ | |
| 8.120 | 0 | N | NO$_2$ | CH$_2$ | S-n-C$_3$H$_7$ | |
| 8.121 | 0 | N | NO$_2$ | CH$_2$ | S-i-C$_3$H$_7$ | |
| 8.122 | 0 | N | NO$_2$ | CH$_2$ | SCH$_2$C$_6$H$_5$ | |
| 8.123 | 1 | N | NO$_2$ | CH$_2$ | i-C$_3$H$_7$ | |
| 8.124 | 1 | N | NO$_2$ | CH$_2$ | CH$_2$C$_6$H$_5$ | |
| 8.125 | 2 | N | NO$_2$ | CH$_2$ | i-C$_3$H$_7$ | |
| 8.126 | 2 | N | NO$_2$ | CH$_2$ | CH$_2$C$_6$H$_5$ | |
| 8.127 | 0 | N | CN | CH$_2$ | i-C$_3$H$_7$ | |
| 8.128 | 0 | N | CN | CH$_2$ | CH$_3$ | |
| 8.129 | 0 | N | CN | CH$_2$ | CH$_2$CO$_2$C$_2$H$_5$ | |
| 8.130 | 0 | N | CN | CH$_2$ | CH$_2$C$_6$H$_5$ | |
| 8.131 | 0 | N | CN | CH$_2$ | CH$_2$C$_6$H$_4$-4-Cl | |
| 8.132 | 0 | N | CN | CH$_2$ | C$_6$H$_5$ | |
| 8.133 | 0 | N | CN | CH$_2$ | C$_6$H$_4$-4-Cl | |
| 8.134 | 0 | N | CN | CH$_2$ | CH$_2$CH=CH$_2$ | |
| 8.135 | 0 | N | CN | CH$_2$ | CH$_2$C≡CH | |
| 8.136 | 0 | N | CN | CH$_2$ | SCH$_3$ | |
| 8.137 | 0 | N | CN | CH$_2$ | SC$_2$H$_5$ | |
| 8.138 | 0 | N | CN | CH$_2$ | S-n-C$_3$H$_7$ | |
| 8.139 | 0 | N | CN | CH$_2$ | S-i-C$_3$H$_7$ | |
| 8.140 | 0 | N | CN | CH$_2$ | SCH$_2$C$_6$H$_5$ | |
| 8.141 | 1 | N | CN | CH$_2$ | i-C$_3$H$_7$ | |
| 8.142 | 1 | N | CN | CH$_2$ | CH$_2$C$_6$H$_5$ | |
| 8.143 | 2 | N | CN | CH$_2$ | i-C$_3$H$_7$ | |
| 8.144 | 2 | N | CN | CH$_2$ | CH$_2$C$_6$H$_5$ | |

TABLE 8-continued

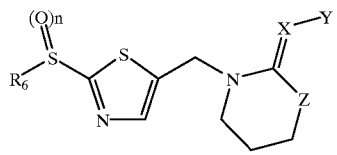

| Compound No. | n | X | Y | Z | R$_6$ | Physical data |
|---|---|---|---|---|---|---|
| 8.145 | 0 | CH | NO$_2$ | CH$_2$ | i-C$_3$H$_7$ | |
| 8.146 | 0 | CH | NO$_2$ | CH$_2$ | CH$_3$ | |
| 8.147 | 0 | CH | NO$_2$ | CH$_2$ | CH$_2$CO$_2$C$_2$H$_5$ | |
| 8.148 | 0 | CH | NO$_2$ | CH$_2$ | CH$_2$C$_6$H$_5$ | |
| 8.149 | 0 | CH | NO$_2$ | CH$_2$ | CH$_2$C$_6$H$_4$-4-Cl | |
| 8.150 | 0 | CH | NO$_2$ | CH$_2$ | C$_6$H$_5$ | |
| 8.151 | 0 | CH | NO$_2$ | CH$_2$ | C$_6$H$_4$-4-Cl | |
| 8.152 | 0 | CH | NO$_2$ | CH$_2$ | CH$_2$CH=CH$_2$ | |
| 8.153 | 0 | CH | NO$_2$ | CH$_2$ | CH$_2$C≡CH | |
| 8.154 | 0 | CH | NO$_2$ | CH$_2$ | SCH$_3$ | |
| 8.155 | 0 | CH | NO$_2$ | CH$_2$ | SC$_2$H$_5$ | |
| 8.156 | 0 | CH | NO$_2$ | CH$_2$ | S-n-C$_3$H$_7$ | |
| 8.157 | 0 | CH | NO$_2$ | CH$_2$ | S-i-C$_3$H$_7$ | |
| 8.158 | 0 | CH | NO$_2$ | CH$_2$ | SCH$_2$C$_6$H$_5$ | |
| 8.159 | 1 | CH | NO$_2$ | CH$_2$ | i-C$_3$H$_7$ | |
| 8.160 | 1 | CH | NO$_2$ | CH$_2$ | CH$_2$C$_6$H$_5$ | |
| 8.161 | 2 | CH | NO$_2$ | CH$_2$ | i-C$_3$H$_7$ | |
| 8.162 | 2 | CH | NO$_2$ | CH$_2$ | CH$_2$C$_6$H$_5$ | |
| 8.163 | 0 | N | NO$_2$ | S | i-C$_3$H$_7$ | |
| 8.164 | 0 | N | NO$_2$ | S | CH$_3$ | |
| 8.165 | 0 | N | NO$_2$ | S | CH$_2$CO$_2$C$_2$H$_5$ | |
| 8.166 | 0 | N | NO$_2$ | S | CH$_2$C$_6$H$_5$ | |
| 8.167 | 0 | N | NO$_2$ | S | CH$_2$C$_6$H$_4$-4-Cl | |
| 8.168 | 0 | N | NO$_2$ | S | C$_6$H$_5$ | |
| 8.169 | 0 | N | NO$_2$ | S | C$_6$H$_4$-4-Cl | |
| 8.170 | 0 | N | NO$_2$ | S | CH$_2$CH=CH$_2$ | |
| 8.171 | 0 | N | NO$_2$ | S | CH$_2$C≡CH | |
| 8.172 | 0 | N | NO$_2$ | S | SCH$_3$ | |
| 8.173 | 0 | N | NO$_2$ | S | SC$_2$H$_5$ | |
| 8.174 | 0 | N | NO$_2$ | S | S-n-C$_3$H$_7$ | |
| 8.175 | 0 | N | NO$_2$ | S | S-i-C$_3$H$_7$ | |
| 8.176 | 0 | N | NO$_2$ | S | SCH$_2$C$_6$H$_5$ | |
| 8.177 | 1 | N | NO$_2$ | S | i-C$_3$H$_7$ | |
| 8.178 | 1 | N | NO$_2$ | S | CH$_2$C$_6$H$_5$ | |
| 8.179 | 2 | N | NO$_2$ | S | i-C$_3$H$_7$ | |
| 8.180 | 2 | N | NO$_2$ | S | CH$_2$C$_6$H$_5$ | |
| 8.181 | 0 | N | CN | S | i-C$_3$H$_7$ | |
| 8.182 | 0 | N | CN | S | CH$_3$ | |
| 8.183 | 0 | N | CN | S | CH$_2$CO$_2$C$_2$H$_5$ | |
| 8.184 | 0 | N | CN | S | CH$_2$C$_6$H$_5$ | |
| 8.185 | 0 | N | CN | S | CH$_2$C$_6$H$_4$-4-Cl | |

TABLE 8-continued

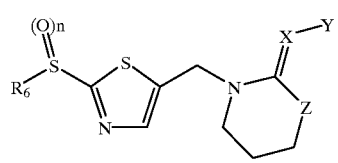

| Compound No. | n | X | Y | Z | R$_6$ | Physical data |
|---|---|---|---|---|---|---|
| 8.186 | 0 | N | CN | S | C$_6$H$_5$ | |
| 8.187 | 0 | N | CN | S | C$_6$H$_4$-4-Cl | |
| 8.188 | 0 | N | CN | S | CH$_2$CH=CH$_2$ | |
| 8.189 | 0 | N | CN | S | CH$_2$C≡CH | |
| 8.190 | 0 | N | CN | S | SCH$_3$ | |
| 8.191 | 0 | N | CN | S | SC$_2$H$_5$ | |
| 8.192 | 0 | N | CN | S | S-n-C$_3$H$_7$ | |
| 8.193 | 0 | N | CN | S | S-i-C$_3$H$_7$ | |
| 8.194 | 0 | N | CN | S | SCH$_2$C$_6$H$_5$ | |
| 8.195 | 1 | N | CN | S | i-C$_3$H$_7$ | |
| 8.196 | 1 | N | CN | S | CH$_2$C$_6$H$_5$ | |
| 8.197 | 2 | N | CN | S | i-C$_3$H$_7$ | |
| 8.198 | 2 | N | CN | S | CH$_2$C$_6$H$_5$ | |
| 8.199 | 0 | CH | NO$_2$ | S | i-C$_3$H$_7$ | |
| 8.200 | 0 | CH | NO$_2$ | S | CH$_3$ | |
| 8.201 | 0 | CH | NO$_2$ | S | CH$_2$CO$_2$C$_2$H$_5$ | |
| 8.202 | 0 | CH | NO$_2$ | S | CH$_2$C$_6$H$_5$ | |
| 8.203 | 0 | CH | NO$_2$ | S | CH$_2$C$_6$H$_4$-4-Cl | |
| 8.204 | 0 | CH | NO$_2$ | S | C$_6$H$_5$ | |
| 8.205 | 0 | CH | NO$_2$ | S | C$_6$H$_4$-4-Cl | |
| 8.206 | 0 | CH | NO$_2$ | S | CH$_2$CH=CH$_2$ | |
| 8.207 | 0 | CH | NO$_2$ | S | CH$_2$C≡CH | |
| 8.208 | 0 | CH | NO$_2$ | S | SCH$_3$ | |
| 8.209 | 0 | CH | NO$_2$ | S | SC$_2$H$_5$ | |
| 8.210 | 0 | CH | NO$_2$ | S | S-n-C$_3$H$_7$ | |
| 8.211 | 0 | CH | NO$_2$ | S | S-i-C$_3$H$_7$ | |
| 8.212 | 0 | CH | NO$_2$ | S | SCH$_2$C$_6$H$_5$ | |
| 8.213 | 1 | CH | NO$_2$ | S | i-C$_3$H$_7$ | |
| 8.214 | 1 | CH | NO$_2$ | S | CH$_2$C$_6$H$_5$ | |
| 8.215 | 2 | CH | NO$_2$ | S | i-C$_3$H$_7$ | |
| 8.216 | 2 | CH | NO$_2$ | S | CH$_2$C$_6$H$_5$ | |

TABLE 9

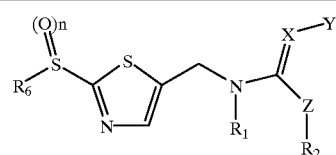

| Compound No. | n | X | Y | Z | R$_1$ | R$_2$ | R$_6$ | Physical data |
|---|---|---|---|---|---|---|---|---|
| 9.1 | 0 | N | NO$_2$ | N-CH$_3$ | CH$_3$ | H | i-C$_3$H$_7$ | |
| 9.2 | 0 | N | NO$_2$ | N-CH$_3$ | CH$_3$ | H | CH$_3$ | |
| 9.3 | 0 | N | NO$_2$ | N-CH$_3$ | CH$_3$ | H | CH$_2$CO$_2$C$_2$H$_5$ | |
| 9.4 | 0 | N | NO$_2$ | N-CH$_3$ | CH$_3$ | H | CH$_2$C$_6$H$_5$ | |
| 9.5 | 0 | N | NO$_2$ | N-CH$_3$ | CH$_3$ | H | C$_6$H$_5$ | |
| 9.6 | 0 | N | NO$_2$ | N-CH$_3$ | CH$_3$ | H | CH$_2$CH=CH$_2$ | |
| 9.7 | 1 | N | NO$_2$ | N-CH$_3$ | CH$_3$ | H | C$_6$H$_5$ | |
| 9.8 | 1 | N | NO$_2$ | N-CH$_3$ | CH$_3$ | H | CH$_2$C$_6$H$_5$ | |
| 9.9 | 2 | N | NO$_2$ | N-CH$_3$ | CH$_3$ | H | C$_6$H$_5$ | |
| 9.10 | 2 | N | NO$_2$ | N-CH$_3$ | CH$_3$ | H | CH$_2$C$_6$H$_5$ | |

TABLE 9-continued

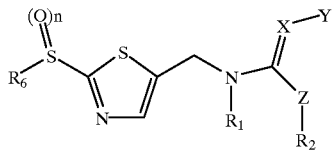

| Compound No. | n | X | Y | Z | R₁ | R₂ | R₆ | Physical data |
|---|---|---|---|---|---|---|---|---|
| 9.11 | 0 | N | CN | N-CH₃ | CH₃ | H | i-C₃H₇ | |
| 9.12 | 0 | N | CN | N-CH₃ | CH₃ | H | CH₃ | |
| 9.13 | 0 | N | CN | N-CH₃ | CH₃ | H | CH₂CO₂C₂H₅ | |
| 9.14 | 0 | N | CN | N-CH₃ | CH₃ | H | CH₂C₆H₅ | |
| 9.15 | 0 | N | CN | N-CH₃ | CH₃ | H | C₆H₅ | |
| 9.16 | 0 | N | CN | N-CH₃ | CH₃ | H | CH₂CH=CH₂ | |
| 9.17 | 1 | N | CN | N-CH₃ | CH₃ | H | C₆H₅ | |
| 9.18 | 1 | N | CN | N-CH₃ | CH₃ | H | CH₂C₆H₅ | |
| 9.19 | 2 | N | CN | N-CH₃ | CH₃ | H | C₆H₅ | |
| 9.20 | 2 | N | CN | N-CH₃ | CH₃ | H | CH₂C₆H₅ | |
| 9.21 | 0 | CH | NO₂ | N-CH₃ | CH₃ | H | i-C₃H₇ | |
| 9.22 | 0 | CH | NO₂ | N-CH₃ | CH₃ | H | CH₃ | |
| 9.23 | 0 | CH | NO₂ | N-CH₃ | CH₃ | H | CH₂CO₂C₂H₅ | |
| 9.24 | 0 | CH | NO₂ | N-CH₃ | CH₃ | H | CH₂C₆H₅ | |
| 9.25 | 0 | CH | NO₂ | N-CH₃ | CH₃ | H | C₆H₅ | |
| 9.26 | 0 | CH | NO₂ | N-CH₃ | CH₃ | H | CH₂CH=CH₂ | |
| 9.27 | 1 | CH | NO₂ | N-CH₃ | CH₃ | H | C₆H₅ | |
| 9.28 | 1 | CH | NO₂ | N-CH₃ | CH₃ | H | CH₂C₆H₅ | |
| 9.29 | 2 | CH | NO₂ | N-CH₃ | CH₃ | H | C₆H₅ | |
| 9.30 | 2 | CH | NO₂ | N-CH₃ | CH₃ | H | CH₂C₆H₅ | |
| 9.31 | 0 | N | NO₂ | N-CH₃ | C₂H₅ | H | i-C₃H₇ | |
| 9.32 | 0 | N | NO₂ | N-CH₃ | C₂H₅ | H | CH₃ | |
| 9.33 | 0 | N | NO₂ | N-CH₃ | C₂H₅ | H | CH₂CO₂C₂H₅ | |
| 9.34 | 0 | N | NO₂ | N-CH₃ | C₂H₅ | H | CH₂C₆H₅ | |
| 9.35 | 0 | N | NO₂ | N-CH₃ | C₂H₅ | H | C₆H₅ | |
| 9.36 | 0 | N | NO₂ | N-CH₃ | C₂H₅ | H | CH₂CH=CH₂ | |
| 9.37 | 1 | N | NO₂ | N-CH₃ | C₂H₅ | H | C₆H₅ | |
| 9.38 | 1 | N | NO₂ | N-CH₃ | C₂H₅ | H | CH₂C₆H₅ | |
| 9.39 | 2 | N | NO₂ | N-CH₃ | C₂H₅ | H | C₆H₅ | |
| 9.40 | 2 | N | NO₂ | N-CH₃ | C₂H₅ | H | CH₂C₆H₅ | |
| 9.41 | 0 | N | CN | N-CH₃ | C₂H₅ | H | i-C₃H₇ | |
| 9.42 | 0 | N | CN | N-CH₃ | C₂H₅ | H | CH₃ | |
| 9.43 | 0 | N | CN | N-CH₃ | C₂H₅ | H | CH₂CO₂C₂H₅ | |
| 9.44 | 0 | N | CN | N-CH₃ | C₂H₅ | H | CH₂C₆H₅ | |
| 9.45 | 0 | N | CN | N-CH₃ | C₂H₅ | H | C₆H₅ | |
| 9.46 | 0 | N | CN | N-CH₃ | C₂H₅ | H | CH₂CH=CH₂ | |
| 9.47 | 1 | N | CN | N-CH₃ | C₂H₅ | H | C₆H₅ | |
| 9.48 | 1 | N | CN | N-CH₃ | C₂H₅ | H | CH₂C₆H₅ | |
| 9.49 | 2 | N | CN | N-CH₃ | C₂H₅ | H | C₆H₅ | |
| 9.50 | 2 | N | CN | N-CH₃ | C₂H₅ | H | CH₂C₆H₅ | |
| 9.51 | 0 | CH | NO₂ | N-CH₃ | C₂H₅ | H | i-C₃H₇ | |
| 9.52 | 0 | CH | NO₂ | N-CH₃ | C₂H₅ | H | CH₃ | |
| 9.53 | 0 | CH | NO₂ | N-CH₃ | C₂H₅ | H | CH₂CO₂C₂H₅ | |
| 9.54 | 0 | CH | NO₂ | N-CH₃ | C₂H₅ | H | CH₂C₆H₅ | |
| 9.55 | 0 | CH | NO₂ | N-CH₃ | C₂H₅ | H | C₆H₅ | |
| 9.56 | 0 | CH | NO₂ | N-CH₃ | C₂H₅ | H | CH₂CH=CH₂ | |
| 9.57 | 1 | CH | NO₂ | N-CH₃ | C₂H₅ | H | C₆H₅ | |
| 9.58 | 1 | CH | NO₂ | N-CH₃ | C₂H₅ | H | CH₂C₆H₅ | |
| 9.59 | 2 | CH | NO₂ | N-CH₃ | C₂H₅ | H | C₆H₅ | |
| 9.60 | 2 | CH | NO₂ | N-CH₃ | C₂H₅ | H | CH₂C₆H₅ | |
| 9.61 | 0 | N | NO₂ | N-CH₃ | H | H | i-C₃H₇ | |
| 9.62 | 0 | N | NO₂ | N-CH₃ | H | H | CH₃ | |
| 9.63 | 0 | N | NO₂ | N-CH₃ | H | H | CH₂CO₂C₂H₅ | |
| 9.64 | 0 | N | NO₂ | N-CH₃ | H | H | CH₂C₆H₅ | |
| 9.65 | 0 | N | NO₂ | N-CH₃ | H | H | C₆H₅ | |
| 9.66 | 0 | N | NO₂ | N-CH₃ | H | H | CH₂CH=CH₂ | |
| 9.67 | 1 | N | NO₂ | N-CH₃ | H | H | C₆H₅ | |
| 9.68 | 1 | N | NO₂ | N-CH₃ | H | H | CH₂C₆H₅ | |
| 9.69 | 2 | N | NO₂ | N-CH₃ | H | H | C₆H₅ | |
| 9.70 | 2 | N | NO₂ | N-CH₃ | H | H | CH₂C₆H₅ | |
| 9.71 | 0 | N | CN | N-CH₃ | H | H | i-C₃H₇ | |
| 9.72 | 0 | N | CN | N-CH₃ | H | H | CH₃ | |
| 9.73 | 0 | N | CN | N-CH₃ | H | H | CH₂CO₂C₂H₅ | |
| 9.74 | 0 | N | CN | N-CH₃ | H | H | CH₂C₆H₅ | |
| 9.75 | 0 | N | CN | N-CH₃ | H | H | C₆H₅ | |
| 9.76 | 0 | N | CN | N-CH₃ | H | H | CH₂CH=CH₂ | |
| 9.77 | 1 | N | CN | N-CH₃ | H | H | C₆H₅ | |
| 9.78 | 1 | N | CN | N-CH₃ | H | H | CH₂C₆H₅ | |

TABLE 9-continued

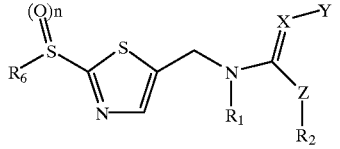

| Compound No. | n | X | Y | Z | $R_1$ | $R_2$ | $R_6$ | Physical data |
|---|---|---|---|---|---|---|---|---|
| 9.79 | 2 | N | CN | N-CH$_3$ | H | H | C$_6$H$_5$ | |
| 9.80 | 2 | N | CN | N-CH$_3$ | H | H | CH$_2$C$_6$H$_5$ | |
| 9.81 | 0 | CH | NO$_2$ | N-CH$_3$ | H | H | i-C$_3$H$_7$ | |
| 9.82 | 0 | CH | NO$_2$ | N-CH$_3$ | H | H | CH$_3$ | |
| 9.83 | 0 | CH | NO$_2$ | N-CH$_3$ | H | H | CH$_2$CO$_2$C$_2$H$_5$ | |
| 9.84 | 0 | CH | NO$_2$ | N-CH$_3$ | H | H | CH$_2$C$_6$H$_5$ | |
| 9.85 | 0 | CH | NO$_2$ | N-CH$_3$ | H | H | C$_6$H$_5$ | |
| 9.86 | 0 | CH | NO$_2$ | N-CH$_3$ | H | H | CH$_2$CH=CH$_2$ | |
| 9.87 | 1 | CH | NO$_2$ | N-CH$_3$ | H | H | C$_6$H$_5$ | |
| 9.88 | 1 | CH | NO$_2$ | N-CH$_3$ | H | H | CH$_2$C$_6$H$_5$ | |
| 9.89 | 2 | CH | NO$_2$ | N-CH$_3$ | H | H | C$_6$H$_5$ | |
| 9.90 | 2 | CH | NO$_2$ | N-CH$_3$ | H | H | CH$_2$C$_6$H$_5$ | |
| 9.91 | 0 | N | NO$_2$ | N-CH$_3$ | CH$_3$ | CH$_3$ | i-C$_3$H$_7$ | |
| 9.92 | 0 | N | NO$_2$ | N-CH$_3$ | CH$_3$ | CH$_3$ | CH$_3$ | |
| 9.93 | 0 | N | NO$_2$ | N-CH$_3$ | CH$_3$ | CH$_3$ | CH$_2$CO$_2$C$_2$H$_5$ | |
| 9.94 | 0 | N | NO$_2$ | N-CH$_3$ | CH$_3$ | CH$_3$ | CH$_2$C$_6$H$_5$ | |
| 9.95 | 0 | N | NO$_2$ | N-CH$_3$ | CH$_3$ | CH$_3$ | C$_6$H$_5$ | |
| 9.96 | 0 | N | NO$_2$ | N-CH$_3$ | CH$_3$ | CH$_3$ | CH$_2$CH=CH$_2$ | |
| 9.97 | 1 | N | NO$_2$ | N-CH$_3$ | CH$_3$ | CH$_3$ | C$_6$H$_5$ | |
| 9.98 | 1 | N | NO$_2$ | N-CH$_3$ | CH$_3$ | CH$_3$ | CH$_2$C$_6$H$_5$ | |
| 9.99 | 2 | N | NO$_2$ | N-CH$_3$ | CH$_3$ | CH$_3$ | C$_6$H$_5$ | |
| 9.100 | 2 | N | NO$_2$ | N-CH$_3$ | CH$_3$ | CH$_3$ | CH$_2$C$_6$H$_5$ | |
| 9.101 | 0 | N | CN | N-CH$_3$ | CH$_3$ | CH$_3$ | i-C$_3$H$_7$ | |
| 9.102 | 0 | N | CN | N-CH$_3$ | CH$_3$ | CH$_3$ | CH$_3$ | |
| 9.103 | 0 | N | CN | N-CH$_3$ | CH$_3$ | CH$_3$ | CH$_2$CO$_2$C$_2$H$_5$ | |
| 9.104 | 0 | N | CN | N-CH$_3$ | CH$_3$ | CH$_3$ | CH$_2$C$_6$H$_5$ | |
| 9.105 | 0 | N | CN | N-CH$_3$ | CH$_3$ | CH$_3$ | C$_6$H$_5$ | |
| 9.106 | 0 | N | CN | N-CH$_3$ | CH$_3$ | CH$_3$ | CH$_2$CH=CH$_2$ | |
| 9.107 | 1 | N | CN | N-CH$_3$ | CH$_3$ | CH$_3$ | C$_6$H$_5$ | |
| 9.108 | 1 | N | CN | N-CH$_3$ | CH$_3$ | CH$_3$ | CH$_2$C$_6$H$_5$ | |
| 9.109 | 2 | N | CN | N-CH$_3$ | CH$_3$ | CH$_3$ | C$_6$H$_5$ | |
| 9.110 | 2 | N | CN | N-CH$_3$ | CH$_3$ | CH$_3$ | CH$_2$C$_6$H$_5$ | |
| 9.111 | 0 | CH | NO$_2$ | N-CH$_3$ | CH$_3$ | CH$_3$ | i-C$_3$H$_7$ | |
| 9.112 | 0 | CH | NO$_2$ | N-CH$_3$ | CH$_3$ | CH$_3$ | CH$_3$ | |
| 9.113 | 0 | CH | NO$_2$ | N-CH$_3$ | CH$_3$ | CH$_3$ | CH$_2$CO$_2$C$_2$H$_5$ | |
| 9.114 | 0 | CH | NO$_2$ | N-CH$_3$ | CH$_3$ | CH$_3$ | CH$_2$C$_6$H$_5$ | |
| 9.115 | 0 | CH | NO$_2$ | N-CH$_3$ | CH$_3$ | CH$_3$ | C$_6$H$_5$ | |
| 9.116 | 0 | CH | NO$_2$ | N-CH$_3$ | CH$_3$ | CH$_3$ | CH$_2$CH=CH$_2$ | |
| 9.117 | 1 | CH | NO$_2$ | N-CH$_3$ | CH$_3$ | CH$_3$ | C$_6$H$_5$ | |
| 9.118 | 1 | CH | NO$_2$ | N-CH$_3$ | CH$_3$ | CH$_3$ | CH$_2$C$_6$H$_5$ | |
| 9.119 | 2 | CH | NO$_2$ | N-CH$_3$ | CH$_3$ | CH$_3$ | C$_6$H$_5$ | |
| 9.120 | 2 | CH | NO$_2$ | N-CH$_3$ | CH$_3$ | CH$_3$ | CH$_2$C$_6$H$_5$ | |
| 9.121 | 0 | N | NO$_2$ | N-CH$_3$ | C$_2$H$_5$ | CH$_3$ | i-C$_3$H$_7$ | |
| 9.122 | 0 | N | NO$_2$ | N-CH$_3$ | C$_2$H$_5$ | CH$_3$ | CH$_3$ | |
| 9.123 | 0 | N | NO$_2$ | N-CH$_3$ | C$_2$H$_5$ | CH$_3$ | CH$_2$CO$_2$C$_2$H$_5$ | |
| 9.124 | 0 | N | NO$_2$ | N-CH$_3$ | C$_2$H$_5$ | CH$_3$ | CH$_2$C$_6$H$_5$ | |
| 9.125 | 0 | N | NO$_2$ | N-CH$_3$ | C$_2$H$_5$ | CH$_3$ | C$_6$H$_5$ | |
| 9.126 | 0 | N | NO$_2$ | N-CH$_3$ | C$_2$H$_5$ | CH$_3$ | CH$_2$CH=CH$_2$ | |
| 9.127 | 1 | N | NO$_2$ | N-CH$_3$ | C$_2$H$_5$ | CH$_3$ | C$_6$H$_5$ | |
| 9.128 | 1 | N | NO$_2$ | N-CH$_3$ | C$_2$H$_5$ | CH$_3$ | CH$_2$C$_6$H$_5$ | |
| 9.129 | 2 | N | NO$_2$ | N-CH$_3$ | C$_2$H$_5$ | CH$_3$ | C$_6$H$_5$ | |
| 9.130 | 2 | N | NO$_2$ | N-CH$_3$ | C$_2$H$_5$ | CH$_3$ | CH$_2$C$_6$H$_5$ | |
| 9.131 | 0 | N | CN | N-CH$_3$ | C$_2$H$_5$ | CH$_3$ | i-C$_3$H$_7$ | |
| 9.132 | 0 | N | CN | N-CH$_3$ | C$_2$H$_5$ | CH$_3$ | CH$_3$ | |
| 9.133 | 0 | N | CN | N-CH$_3$ | C$_2$H$_5$ | CH$_3$ | CH$_2$CO$_2$C$_2$H$_5$ | |
| 9.134 | 0 | N | CN | N-CH$_3$ | C$_2$H$_5$ | CH$_3$ | CH$_2$C$_6$H$_5$ | |
| 9.135 | 0 | N | CN | N-CH$_3$ | C$_2$H$_5$ | CH$_3$ | C$_6$H$_5$ | |
| 9.136 | 0 | N | CN | N-CH$_3$ | C$_2$H$_5$ | CH$_3$ | CH$_2$CH=CH$_2$ | |
| 9.137 | 1 | N | CN | N-CH$_3$ | C$_2$H$_5$ | CH$_3$ | C$_6$H$_5$ | |
| 9.138 | 1 | N | CN | N-CH$_3$ | C$_2$H$_5$ | CH$_3$ | CH$_2$C$_6$H$_5$ | |
| 9.139 | 2 | N | CN | N-CH$_3$ | C$_2$H$_5$ | CH$_3$ | C$_6$H$_5$ | |
| 9.140 | 2 | N | CN | N-CH$_3$ | C$_2$H$_5$ | CH$_3$ | CH$_2$C$_6$H$_5$ | |
| 9.141 | 0 | CH | NO$_2$ | N-CH$_3$ | C$_2$H$_5$ | CH$_3$ | i-C$_3$H$_7$ | |
| 9.142 | 0 | CH | NO$_2$ | N-CH$_3$ | C$_2$H$_5$ | CH$_3$ | CH$_3$ | |
| 9.143 | 0 | CH | NO$_2$ | N-CH$_3$ | C$_2$H$_5$ | CH$_3$ | CH$_2$CO$_2$C$_2$H$_5$ | |
| 9.144 | 0 | CH | NO$_2$ | N-CH$_3$ | C$_2$H$_5$ | CH$_3$ | CH$_2$C$_6$H$_5$ | |
| 9.145 | 0 | CH | NO$_2$ | N-CH$_3$ | C$_2$H$_5$ | CH$_3$ | C$_6$H$_5$ | |
| 9.146 | 0 | CH | NO$_2$ | N-CH$_3$ | C$_2$H$_5$ | CH$_3$ | CH$_2$CH=CH$_2$ | |

TABLE 9-continued

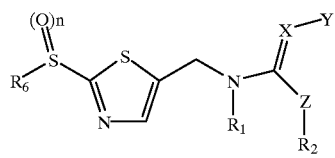

| Compound No. | n | X | Y | Z | R₁ | R₂ | R₆ | Physical data |
|---|---|---|---|---|---|---|---|---|
| 9.147 | 1 | CH | NO₂ | N-CH₃ | C₂H₅ | CH₃ | C₆H₅ | |
| 9.148 | 1 | CH | NO₂ | N-CH₃ | C₂H₅ | CH₃ | CH₂C₆H₅ | |
| 9.149 | 2 | CH | NO₂ | N-CH₃ | C₂H₅ | CH₃ | C₆H₅ | |
| 9.150 | 2 | CH | NO₂ | N-CH₃ | C₂H₅ | CH₃ | CH₂C₆H₅ | |
| 9.151 | 0 | N | NO₂ | N-CH₃ | H | CH₃ | i-C₃H₇ | |
| 9.152 | 0 | N | NO₂ | N-CH₃ | H | CH₃ | CH₃ | |
| 9.153 | 0 | N | NO₂ | N-CH₃ | H | CH₃ | CH₂CO₂C₂H₅ | |
| 9.154 | 0 | N | NO₂ | N-CH₃ | H | CH₃ | CH₂C₆H₅ | |
| 9.155 | 0 | N | NO₂ | N-CH₃ | H | CH₃ | C₆H₅ | |
| 9.156 | 0 | N | NO₂ | N-CH₃ | H | CH₃ | CH₂CH=CH₂ | |
| 9.157 | 1 | N | NO₂ | N-CH₃ | H | CH₃ | C₆H₅ | |
| 9.158 | 1 | N | NO₂ | N-CH₃ | H | CH₃ | CH₂C₆H₅ | |
| 9.159 | 2 | N | NO₂ | N-CH₃ | H | CH₃ | C₆H₅ | |
| 9.160 | 2 | N | NO₂ | N-CH₃ | H | CH₃ | CH₂C₆H₅ | |
| 9.161 | 0 | N | CN | N-CH₃ | H | CH₃ | i-C₃H₇ | |
| 9.162 | 0 | N | CN | N-CH₃ | H | CH₃ | CH₃ | |
| 9.163 | 0 | N | CN | N-CH₃ | H | CH₃ | CH₂CO₂C₂H₅ | |
| 9.164 | 0 | N | CN | N-CH₃ | H | CH₃ | CH₂C₆H₅ | |
| 9.165 | 0 | N | CN | N-CH₃ | H | CH₃ | C₆H₅ | |
| 9.166 | 0 | N | CN | N-CH₃ | H | CH₃ | CH₂CH=CH₂ | |
| 9.167 | 1 | N | CN | N-CH₃ | H | CH₃ | C₆H₅ | |
| 9.168 | 1 | N | CN | N-CH₃ | H | CH₃ | CH₂C₆H₅ | |
| 9.169 | 2 | N | CN | N-CH₃ | H | CH₃ | C₆H₅ | |
| 9.170 | 2 | N | CN | N-CH₃ | H | CH₃ | CH₂C₆H₅ | |
| 9.171 | 0 | CH | NO₂ | N-CH₃ | H | CH₃ | i-C₃H₇ | |
| 9.172 | 0 | CH | NO₂ | N-CH₃ | H | CH₃ | CH₃ | |
| 9.173 | 0 | CH | NO₂ | N-CH₃ | H | CH₃ | CH₂CO₂C₂H₅ | |
| 9.174 | 0 | CH | NO₂ | N-CH₃ | H | CH₃ | CH₂C₆H₅ | |
| 9.175 | 0 | CH | NO₂ | N-CH₃ | H | CH₃ | C₆H₅ | |
| 9.176 | 0 | CH | NO₂ | N-CH₃ | H | CH₃ | CH₂CH=CH₂ | |
| 9.177 | 1 | CH | NO₂ | N-CH₃ | H | CH₃ | C₆H₅ | |
| 9.178 | 1 | CH | NO₂ | N-CH₃ | H | CH₃ | CH₂C₆H₅ | |
| 9.179 | 2 | CH | NO₂ | N-CH₃ | H | CH₃ | C₆H₅ | |
| 9.180 | 2 | CH | NO₂ | N-CH₃ | H | CH₃ | CH₂C₆H₅ | |
| 9.181 | 0 | N | NO₂ | CH₂ | CH₃ | H | i-C₃H₇ | |
| 9.182 | 0 | N | NO₂ | CH₂ | CH₃ | H | CH₃ | |
| 9.183 | 0 | N | NO₂ | CH₂ | CH₃ | H | CH₂CO₂C₂H₅ | |
| 9.184 | 0 | N | NO₂ | CH₂ | CH₃ | H | CH₂C₆H₅ | |
| 9.185 | 0 | N | NO₂ | CH₂ | CH₃ | H | C₆H₅ | |
| 9.186 | 0 | N | NO₂ | CH₂ | CH₃ | H | CH₂CH=CH₂ | |
| 9.187 | 1 | N | NO₂ | CH₂ | CH₃ | H | C₆H₅ | |
| 9.188 | 1 | N | NO₂ | CH₂ | CH₃ | H | CH₂C₆H₅ | |
| 9.189 | 2 | N | NO₂ | CH₂ | CH₃ | H | C₆H₅ | |
| 9.190 | 2 | N | NO₂ | CH₂ | CH₃ | H | CH₂C₆H₅ | |
| 9.191 | 0 | N | CN | CH₂ | CH₃ | H | i-C₃H₇ | |
| 9.192 | 0 | N | CN | CH₂ | CH₃ | H | CH₃ | |
| 9.193 | 0 | N | CN | CH₂ | CH₃ | H | CH₂CO₂C₂H₅ | |
| 9.194 | 0 | N | CN | CH₂ | CH₃ | H | CH₂C₆H₅ | |
| 9.195 | 0 | N | CN | CH₂ | CH₃ | H | C₆H₅ | |
| 9.196 | 0 | N | CN | CH₂ | CH₃ | H | CH₂CH=CH₂ | |
| 9.197 | 1 | N | CN | CH₂ | CH₃ | H | C₆H₅ | |
| 9.198 | 1 | N | CN | CH₂ | CH₃ | H | CH₂C₆H₅ | |
| 9.199 | 2 | N | CN | CH₂ | CH₃ | H | C₆H₅ | |
| 9.200 | 2 | N | CN | CH₂ | CH₃ | H | CH₂C₆H₅ | |
| 9.201 | 0 | CH | NO₂ | CH₂ | CH₃ | H | i-C₃H₇ | |
| 9.202 | 0 | CH | NO₂ | CH₂ | CH₃ | H | CH₃ | |
| 9.203 | 0 | CH | NO₂ | CH₂ | CH₃ | H | CH₂CO₂C₂H₅ | |
| 9.204 | 0 | CH | NO₂ | CH₂ | CH₃ | H | CH₂C₆H₅ | |
| 9.205 | 0 | CH | NO₂ | CH₂ | CH₃ | H | C₆H₅ | |
| 9.206 | 0 | CH | NO₂ | CH₂ | CH₃ | H | CH₂CH=CH₂ | |
| 9.207 | 1 | CH | NO₂ | CH₂ | CH₃ | H | C₆H₅ | |
| 9.208 | 1 | CH | NO₂ | CH₂ | CH₃ | H | CH₂C₆H₅ | |
| 9.209 | 2 | CH | NO₂ | CH₂ | CH₃ | H | C₆H₅ | |
| 9.210 | 2 | CH | NO₂ | CH₂ | CH₃ | H | CH₂C₆H₅ | |
| 9.211 | 0 | N | NO₂ | CH₂ | C₂H₅ | H | i-C₃H₇ | |
| 9.212 | 0 | N | NO₂ | CH₂ | C₂H₅ | H | CH₃ | |
| 9.213 | 0 | N | NO₂ | CH₂ | C₂H₅ | H | CH₂CO₂C₂H₅ | |
| 9.214 | 0 | N | NO₂ | CH₂ | C₂H₅ | H | CH₂C₆H₅ | |

TABLE 9-continued

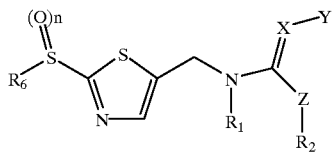

| Compound No. | n | X | Y | Z | $R_1$ | $R_2$ | $R_6$ | Physical data |
|---|---|---|---|---|---|---|---|---|
| 9.215 | 0 | N | $NO_2$ | $CH_2$ | $C_2H_5$ | H | $C_6H_5$ | |
| 9.216 | 0 | N | $NO_2$ | $CH_2$ | $C_2H_5$ | H | $CH_2CH=CH_2$ | |
| 9.217 | 1 | N | $NO_2$ | $CH_2$ | $C_2H_5$ | H | $C_6H_5$ | |
| 9.218 | 1 | N | $NO_2$ | $CH_2$ | $C_2H_5$ | H | $CH_2C_6H_5$ | |
| 9.219 | 2 | N | $NO_2$ | $CH_2$ | $C_2H_5$ | H | $C_6H_5$ | |
| 9.220 | 2 | N | $NO_2$ | $CH_2$ | $C_2H_5$ | H | $CH_2C_6H_5$ | |
| 9.221 | 0 | N | CN | $CH_2$ | $C_2H_5$ | H | $i\text{-}C_3H_7$ | |
| 9.222 | 0 | N | CN | $CH_2$ | $C_2H_5$ | H | $CH_3$ | |
| 9.223 | 0 | N | CN | $CH_2$ | $C_2H_5$ | H | $CH_2CO_2C_2H_5$ | |
| 9.224 | 0 | N | CN | $CH_2$ | $C_2H_5$ | H | $CH_2C_6H_5$ | |
| 9.225 | 0 | N | CN | $CH_2$ | $C_2H_5$ | H | $C_6H_5$ | |
| 9.226 | 0 | N | CN | $CH_2$ | $C_2H_5$ | H | $CH_2CH=CH_2$ | |
| 9.227 | 1 | N | CN | $CH_2$ | $C_2H_5$ | H | $C_6H_5$ | |
| 9.228 | 1 | N | CN | $CH_2$ | $C_2H_5$ | H | $CH_2C_6H_5$ | |
| 9.229 | 2 | N | CN | $CH_2$ | $C_2H_5$ | H | $C_6H_5$ | |
| 9.230 | 2 | N | CN | $CH_2$ | $C_2H_5$ | H | $CH_2C_6H_5$ | |
| 9.231 | 0 | CH | $NO_2$ | $CH_2$ | $C_2H_5$ | H | $i\text{-}C_3H_7$ | |
| 9.232 | 0 | CH | $NO_2$ | $CH_2$ | $C_2H_5$ | H | $CH_3$ | |
| 9.233 | 0 | CH | $NO_2$ | $CH_2$ | $C_2H_5$ | H | $CH_2CO_2C_2H_5$ | |
| 9.234 | 0 | CH | $NO_2$ | $CH_2$ | $C_2H_5$ | H | $CH_2C_6H_5$ | |
| 9.235 | 0 | CH | $NO_2$ | $CH_2$ | $C_2H_5$ | H | $C_6H_5$ | |
| 9.236 | 0 | CH | $NO_2$ | $CH_2$ | $C_2H_5$ | H | $CH_2CH=CH_2$ | |
| 9.237 | 1 | CH | $NO_2$ | $CH_2$ | $C_2H_5$ | H | $C_6H_5$ | |
| 9.238 | 1 | CH | $NO_2$ | $CH_2$ | $C_2H_5$ | H | $CH_2C_6H_5$ | |
| 9.239 | 2 | CH | $NO_2$ | $CH_2$ | $C_2H_5$ | H | $C_6H_5$ | |
| 9.240 | 2 | CH | $NO_2$ | $CH_2$ | $C_2H_5$ | H | $CH_2C_6H_5$ | |
| 9.241 | 0 | N | $NO_2$ | $CH_2$ | H | H | $i\text{-}C_3H_7$ | |
| 9.242 | 0 | N | $NO_2$ | $CH_2$ | H | H | $CH_3$ | |
| 9.243 | 0 | N | $NO_2$ | $CH_2$ | H | H | $CH_2CO_2C_2H_5$ | |
| 9.244 | 0 | N | $NO_2$ | $CH_2$ | H | H | $CH_2C_6H_5$ | |
| 9.245 | 0 | N | $NO_2$ | $CH_2$ | H | H | $C_6H_5$ | |
| 9.246 | 0 | N | $NO_2$ | $CH_2$ | H | H | $CH_2CH=CH_2$ | |
| 9.247 | 1 | N | $NO_2$ | $CH_2$ | H | H | $C_6H_5$ | |
| 9.248 | 1 | N | $NO_2$ | $CH_2$ | H | H | $CH_2C_6H_5$ | |
| 9.249 | 2 | N | $NO_2$ | $CH_2$ | H | H | $C_6H_5$ | |
| 9.250 | 2 | N | $NO_2$ | $CH_2$ | H | H | $CH_2C_6H_5$ | |
| 9.251 | 0 | N | CN | $CH_2$ | H | H | $i\text{-}C_3H_7$ | |
| 9.252 | 0 | N | CN | $CH_2$ | H | H | $CH_3$ | |
| 9.253 | 0 | N | CN | $CH_2$ | H | H | $CH_2CO_2C_2H_5$ | |
| 9.254 | 0 | N | CN | $CH_2$ | H | H | $CH_2C_6H_5$ | |
| 9.255 | 0 | N | CN | $CH_2$ | H | H | $C_6H_5$ | |
| 9.256 | 0 | N | CN | $CH_2$ | H | H | $CH_2CH=CH_2$ | |
| 9.257 | 1 | N | CN | $CH_2$ | H | H | $C_6H_5$ | |
| 9.258 | 1 | N | CN | $CH_2$ | H | H | $CH_2C_6H_5$ | |
| 9.259 | 2 | N | CN | $CH_2$ | H | H | $C_6H_5$ | |
| 9.260 | 2 | N | CN | $CH_2$ | H | H | $CH_2C_6H_5$ | |
| 9.261 | 0 | CH | $NO_2$ | $CH_2$ | H | H | $i\text{-}C_3H_7$ | |
| 9.262 | 0 | CH | $NO_2$ | $CH_2$ | H | H | $CH_3$ | |
| 9.263 | 0 | CH | $NO_2$ | $CH_2$ | H | H | $CH_2CO_2C_2H_5$ | |
| 9.264 | 0 | CH | $NO_2$ | $CH_2$ | H | H | $CH_2C_6H_5$ | |
| 9.265 | 0 | CH | $NO_2$ | $CH_2$ | H | H | $C_6H_5$ | |
| 9.266 | 0 | CH | $NO_2$ | $CH_2$ | H | H | $CH_2CH=CH_2$ | |
| 9.267 | 1 | CH | $NO_2$ | $CH_2$ | H | H | $C_6H_5$ | |
| 9.268 | 1 | CH | $NO_2$ | $CH_2$ | H | H | $CH_2C_6H_5$ | |
| 9.269 | 2 | CH | $NO_2$ | $CH_2$ | H | H | $C_6H_5$ | |
| 9.270 | 2 | CH | $NO_2$ | $CH_2$ | H | H | $CH_2C_6H_5$ | |

TABLE 10

[Structure: R_6-S(O)_n-thiazole-CH_2-N(cyclic)-C(=N-Y)-NH with tetrahydropyrimidine ring]

| Compound No. | n | Y | R_6 | Physical data |
|---|---|---|---|---|
| 10.1 | 0 | NO_2 | CH_3 | |
| 10.2 | 0 | NO_2 | C_2H_5 | |
| 10.3 | 0 | NO_2 | n-C_3H_7 | |
| 10.4 | 0 | NO_2 | i-C_3H_7 | |
| 10.5 | 0 | NO_2 | n-C_4H_9 | |
| 10.6 | 0 | NO_2 | t-C_4H_9 | |
| 10.7 | 0 | NO_2 | cyclo-C_3H_5 | |
| 10.8 | 0 | NO_2 | CH_2C_6H_5 | |
| 10.9 | 0 | NO_2 | CH_2C_6H_4-4-CH_3 | |
| 10.10 | 0 | NO_2 | CH_2C_6H_4-4-OCH_3 | |
| 10.11 | 0 | NO_2 | CH_2C_6H_4-4-Cl | |
| 10.12 | 0 | NO_2 | CH_2C_6H_4-4-NO_2 | |
| 10.13 | 0 | NO_2 | CH_2-2-furyl | |
| 10.14 | 0 | NO_2 | CH_2-2-thienyl | |
| 10.15 | 0 | NO_2 | C_6H_5 | |
| 10.16 | 0 | NO_2 | C_6H_4-4-CH_3 | |
| 10.17 | 0 | NO_2 | C_6H_4-4-OCH_3 | |
| 10.18 | 0 | NO_2 | C_6H_4-4-Cl | |
| 10.19 | 0 | NO_2 | C_6H_4-4-NO_2 | |
| 10.20 | 0 | NO_2 | CH_2CH=CH_2 | |
| 10.21 | 0 | NO_2 | CH_2C≡CH | |
| 10.22 | 0 | NO_2 | CH_2CH=CHC_6H_5 | |
| 10.23 | 0 | NO_2 | CH_2C≡CC_6H_5 | |
| 10.24 | 0 | NO_2 | SCH_3 | |
| 10.25 | 0 | NO_2 | SC_2H_5 | |
| 10.26 | 0 | NO_2 | S-n-C_3H_7 | |
| 10.27 | 0 | NO_2 | S-i-C_3H_7 | |
| 10.28 | 0 | NO_2 | S-n-C_4H_9 | |
| 10.29 | 0 | NO_2 | S-t-C_4H_9 | |
| 10.30 | 0 | NO_2 | S-cyclo-C_3H_5 | |
| 10.31 | 0 | NO_2 | SCH_2C_6H_5 | |
| 10.32 | 0 | NO_2 | SCH_2C_6H_4-4-CH_3 | |
| 10.33 | 0 | NO_2 | SCH_2C_6H_4-4-OCH_3 | |
| 10.34 | 0 | NO_2 | SCH_2C_6H_4-4-Cl | |
| 10.35 | 0 | NO_2 | SCH_2C_6H_4-4-NO_2 | |
| 10.36 | 0 | NO_2 | SCH_2-2-furyl | |
| 10.37 | 0 | NO_2 | SCH_2-2-thienyl | |
| 10.38 | 0 | NO_2 | SC_6H_5 | |
| 10.39 | 0 | NO_2 | SC_6H_4-4-CH_3 | |
| 10.40 | 0 | NO_2 | SC_6H_4-4-OCH_3 | |
| 10.41 | 0 | NO_2 | SC_6H_4-4-Cl | |
| 10.42 | 0 | NO_2 | SC_6H_4-4-NO_2 | |
| 10.43 | 0 | NO_2 | SCH_2CH=CH_2 | |
| 10.44 | 0 | NO_2 | SCH_2C≡CH | |
| 10.45 | 0 | NO_2 | SCH_2CH=CHC_6H_5 | |
| 10.46 | 0 | NO_2 | SCH_2C≡CC_6H_5 | |
| 10.47 | 0 | NO_2 | [structure shown: S-thiazole-CH_2-N(cyclic)-C(=N-NO_2)-NH] | |
| 10.48 | 1 | NO_2 | CH_3 | |
| 10.49 | 1 | NO_2 | C_2H_5 | |
| 10.50 | 1 | NO_2 | n-C_3H_7 | |
| 10.51 | 1 | NO_2 | i-C_3H_7 | |
| 10.52 | 1 | NO_2 | n-C_4H_9 | |
| 10.53 | 1 | NO_2 | t-C_4H_9 | |
| 10.54 | 1 | NO_2 | cyclo-C_3H_5 | |
| 10.55 | 1 | NO_2 | CH_2C_6H_5 | |
| 10.56 | 1 | NO_2 | CH_2C_6H_4-4-CH_3 | |
| 10.57 | 1 | NO_2 | CH_2C_6H_4-4-OCH_3 | |
| 10.58 | 1 | NO_2 | CH_2C_6H_4-4-Cl | |
| 10.59 | 1 | NO_2 | CH_2C_6H_4-4-NO_2 | |
| 10.60 | 1 | NO_2 | CH_2-2-furyl | |

TABLE 10-continued

Structure: $R_6-S(O)_n$-thiazole-$CH_2$-N(tetrahydropyrimidine=N-Y)NH

| Compound No. | n | Y | R₆ | Physical data |
|---|---|---|---|---|
| 10.61 | 1 | NO₂ | CH₂-2-thienyl | |
| 10.62 | 1 | NO₂ | C₆H₅ | |
| 10.63 | 1 | NO₂ | C₆H₄-4-CH₃ | |
| 10.64 | 1 | NO₂ | C₆H₄-4-OCH₃ | |
| 10.65 | 1 | NO₂ | C₆H₄-4-Cl | |
| 10.66 | 1 | NO₂ | C₆H₄-4-NO₂ | |
| 10.67 | 1 | NO₂ | CH₂CH=CH₂ | |
| 10.68 | 1 | NO₂ | CH₂C≡CH | |
| 10.69 | 1 | NO₂ | CH₂CH=CHC₆H₅ | |
| 10.70 | 1 | NO₂ | CH₂C≡CC₆H₅ | |
| 10.71 | 2 | NO₂ | CH₃ | |
| 10.72 | 2 | NO₂ | C₂H₅ | |
| 10.73 | 2 | NO₂ | n-C₃H₇ | |
| 10.74 | 2 | NO₂ | i-C₃H₇ | |
| 10.75 | 2 | NO₂ | n-C₄H₉ | |
| 10.76 | 2 | NO₂ | t-C₄H₉ | |
| 10.77 | 2 | NO₂ | cyclo-C₃H₅ | |
| 10.78 | 2 | NO₂ | CH₂C₆H₅ | |
| 10.79 | 2 | NO₂ | CH₂C₆H₄-4-CH₃ | |
| 10.80 | 2 | NO₂ | CH₂C₆H₄-4-OCH₃ | |
| 10.81 | 2 | NO₂ | CH₂C₆H₄-4-Cl | |
| 10.82 | 2 | NO₂ | CH₂C₆H₄-4-NO₂ | |
| 10.83 | 2 | NO₂ | CH₂-2-furyl | |
| 10.84 | 2 | NO₂ | CH₂-2-thienyl | |
| 10.85 | 2 | NO₂ | C₆H₅ | |
| 10.86 | 2 | NO₂ | C₆H₄-4-CH₃ | |
| 10.87 | 2 | NO₂ | C₆H₄-4-OCH₃ | |
| 10.88 | 2 | NO₂ | C₆H₄-4-Cl | |
| 10.89 | 2 | NO₂ | C₆H₄-4-NO₂ | |
| 10.90 | 2 | NO₂ | CH₂CH=CH₂ | |
| 10.91 | 2 | NO₂ | CH₂C≡CH | |
| 10.92 | 2 | NO₂ | CH₂CH=CHC₆H₅ | |
| 10.93 | 2 | NO₂ | CH₂C≡CC₆H₅ | |
| 10.94 | 0 | NO₂ | CH₂SCH₃ | |
| 10.95 | 0 | NO₂ | CH₂SC₂H₅ | |
| 10.96 | 0 | NO₂ | CH₂S-n-C₃H₇ | |
| 10.97 | 0 | NO₂ | CH₂S-i-C₃H₇ | |
| 10.98 | 0 | NO₂ | CH₂S-n-C₄H₉ | |
| 10.99 | 0 | NO₂ | CH₂S-t-C₄H₉ | |
| 10.100 | 0 | NO₂ | CH₂S-cyclo-C₃H₅ | |
| 10.101 | 0 | NO₂ | CH₂SCH₂C₆H₅ | |
| 10.102 | 0 | NO₂ | CH₂SCH₂C₆H₄-4-CH₃ | |
| 10.103 | 0 | NO₂ | CH₂SCH₂C₆H₄-4-OCH₃ | |
| 10.104 | 0 | NO₂ | CH₂SCH₂C₆H₄-4-Cl | |
| 10.105 | 0 | NO₂ | CH₂SCH₂C₆H₄-4-NO₂ | |
| 10.106 | 0 | NO₂ | CH₂SCH₂-2-furyl | |
| 10.107 | 0 | NO₂ | CH₂SCH₂-2-thienyl | |
| 10.108 | 0 | NO₂ | CH₂SC₆H₅ | |
| 10.109 | 0 | NO₂ | CH₂SC₆H₄-4-CH₃ | |
| 10.110 | 0 | NO₂ | CH₂SC₆H₄-4-OCH₃ | |
| 10.111 | 0 | NO₂ | CH₂SC₆H₄-4-Cl | |
| 10.112 | 0 | NO₂ | CH₂SC₆H₄-4-NO₂ | |
| 10.113 | 0 | NO₂ | CH₂SCH₂CH=CH₂ | |
| 10.114 | 0 | NO₂ | CH₂SCH₂C≡CH | |
| 10.115 | 0 | NO₂ | CH₂SCH₂CH=CHC₆H₅ | |
| 10.116 | 0 | NO₂ | CH₂SCH₂C≡CC₆H₅ | |
| 10.117 | 0 | NO₂ | CH₃S-thiazole-CH₂-N(tetrahydropyrimidine=N-NO₂)NH | |
| 10.118 | 0 | CN | CH₃ | |
| 10.119 | 0 | CN | C₂H₅ | |
| 10.120 | 0 | CN | n-C₃H₇ | |

TABLE 10-continued

Structure: $R_6-S(O)_n-$(thiazole-CH$_2$-)N(tetrahydropyrimidine)=N-Y

| Compound No. | n | Y | R$_6$ | Physical data |
|---|---|---|---|---|
| 10.121 | 0 | CN | i-C$_3$H$_7$ | |
| 10.122 | 0 | CN | n-C$_4$H$_9$ | |
| 10.123 | 0 | CN | t-C$_4$H$_9$ | |
| 10.124 | 0 | CN | cyclo-C$_3$H$_5$ | |
| 10.125 | 0 | CN | CH$_2$C$_6$H$_5$ | |
| 10.126 | 0 | CN | CH$_2$C$_6$H$_4$-4-CH$_3$ | |
| 10.127 | 0 | CN | CH$_2$C$_6$H$_4$-4-OCH$_3$ | |
| 10.128 | 0 | CN | CH$_2$C$_6$H$_4$-4-Cl | |
| 10.129 | 0 | CN | CH$_2$C$_6$H$_4$-4-NO$_2$ | |
| 10.130 | 0 | CN | CH$_2$-2-furyl | |
| 10.131 | 0 | CN | CH$_2$-2-thienyl | |
| 10.132 | 0 | CN | C$_6$H$_5$ | |
| 10.133 | 0 | CN | C$_6$H$_4$-4-CH$_3$ | |
| 10.134 | 0 | CN | C$_6$H$_4$-4-OCH$_3$ | |
| 10.135 | 0 | CN | C$_6$H$_4$-4-Cl | |
| 10.136 | 0 | CN | C$_6$H$_4$-4-NO$_2$ | |
| 10.137 | 0 | CN | CH$_2$CH=CH$_2$ | |
| 10.138 | 0 | CN | CH$_2$C≡CH | |
| 10.139 | 0 | CN | CH$_2$CH=CHC$_6$H$_5$ | |
| 10.140 | 0 | CN | CH$_2$C≡CC$_6$H$_5$ | |
| 10.141 | 0 | CN | SCH$_3$ | |
| 10.142 | 0 | CN | SC$_2$H$_5$ | |
| 10.143 | 0 | CN | S-n-C$_3$H$_7$ | |
| 10.144 | 0 | CN | S-i-C$_3$H$_7$ | |
| 10.145 | 0 | CN | S-n-C$_4$H$_9$ | |
| 10.146 | 0 | CN | S-t-C$_4$H$_9$ | |
| 10.147 | 0 | CN | S-cyclo-C$_3$H$_5$ | |
| 10.148 | 0 | CN | SCH$_2$C$_6$H$_5$ | |
| 10.149 | 0 | CN | SCH$_2$C$_6$H$_4$-4-CH$_3$ | |
| 10.150 | 0 | CN | SCH$_2$C$_6$H$_4$-4-OCH$_3$ | |
| 10.151 | 0 | CN | SCH$_2$C$_6$H$_4$-4-Cl | |
| 10.152 | 0 | CN | SCH$_2$C$_6$H$_4$-4-NO$_2$ | |
| 10.153 | 0 | CN | SCH$_2$-2-furyl | |
| 10.154 | 0 | CN | SCH$_2$-2-thienyl | |
| 10.155 | 0 | CN | SC$_6$H$_5$ | |
| 10.156 | 0 | CN | SC$_6$H$_4$-4-CH$_3$ | |
| 10.157 | 0 | CN | SC$_6$H$_4$-4-OCH$_3$ | |
| 10.158 | 0 | CN | SC$_6$H$_4$-4-Cl | |
| 10.159 | 0 | CN | SC$_6$H$_4$-4-NO$_2$ | |
| 10.160 | 0 | CN | SCH$_2$CH=CH$_2$ | |
| 10.161 | 0 | CN | SCH$_2$C≡CH | |
| 10.162 | 0 | CN | SCH$_2$CH=CHC$_6$H$_5$ | |
| 10.163 | 0 | CN | SCH$_2$C≡CC$_6$H$_5$ | |
| 10.164 | 0 | CN | (structure: 2-mercapto-thiazol-5-ylmethyl-tetrahydropyrimidin-2-ylidene-cyanamide) | |
| 10.165 | 1 | CN | CH$_3$ | |
| 10.166 | 1 | CN | C$_2$H$_5$ | |
| 10.167 | 1 | CN | n-C$_3$H$_7$ | |
| 10.168 | 1 | CN | i-C$_3$H$_7$ | |
| 10.169 | 1 | CN | n-C$_4$H$_9$ | |
| 10.170 | 1 | CN | t-C$_4$H$_9$ | |
| 10.171 | 1 | CN | cyclo-C$_3$H$_5$ | |
| 10.172 | 1 | CN | CH$_2$C$_6$H$_5$ | |
| 10.173 | 1 | CN | CH$_2$C$_6$H$_4$-4-CH$_3$ | |
| 10.174 | 1 | CN | CH$_2$C$_6$H$_4$-4-OCH$_3$ | |
| 10.175 | 1 | CN | CH$_2$C$_6$H$_4$-4-Cl | |
| 10.176 | 1 | CN | CH$_2$C$_6$H$_4$-4-NO$_2$ | |
| 10.177 | 1 | CN | CH$_2$-2-furyl | |
| 10.178 | 1 | CN | CH$_2$-2-thienyl | |
| 10.179 | 1 | CN | C$_6$H$_5$ | |
| 10.180 | 1 | CN | C$_6$H$_4$-4-CH$_3$ | |

TABLE 10-continued

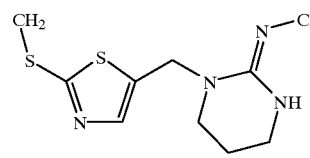

| Compound No. | n | Y | R$_6$ | Physical data |
|---|---|---|---|---|
| 10.181 | 1 | CN | C$_6$H$_4$-4-OCH$_3$ | |
| 10.182 | 1 | CN | C$_6$H$_4$-4-Cl | |
| 10.183 | 1 | CN | C$_6$H$_4$-4-NO$_2$ | |
| 10.184 | 1 | CN | CH$_2$CH=CH$_2$ | |
| 10.185 | 1 | CN | CH$_2$C≡CH | |
| 10.186 | 1 | CN | CH$_2$CH=CHC$_6$H$_5$ | |
| 10.187 | 1 | CN | CH$_2$C≡CC$_6$H$_5$ | |
| 10.188 | 2 | CN | CH$_3$ | |
| 10.189 | 2 | CN | C$_2$H$_5$ | |
| 10.190 | 2 | CN | n-C$_3$H$_7$ | |
| 10.191 | 2 | CN | i-C$_3$H$_7$ | |
| 10.192 | 2 | CN | n-C$_4$H$_9$ | |
| 10.193 | 2 | CN | t-C$_4$H$_9$ | |
| 10.194 | 2 | CN | cyclo-C$_3$H$_5$ | |
| 10.195 | 2 | CN | CH$_2$C$_6$H$_5$ | |
| 10.196 | 2 | CN | CH$_2$C$_6$H$_4$-4-CH$_3$ | |
| 10.197 | 2 | CN | CH$_2$C$_6$H$_4$-4-OCH$_3$ | |
| 10.198 | 2 | CN | CH$_2$C$_6$H$_4$-4-Cl | |
| 10.199 | 2 | CN | CH$_2$C$_6$H$_4$-4-NO$_2$ | |
| 10.200 | 2 | CN | CH$_2$-2-furyl | |
| 10.201 | 2 | CN | CH$_2$-2-thienyl | |
| 10.202 | 2 | CN | C$_6$H$_5$ | |
| 10.203 | 2 | CN | C$_6$H$_4$-4-CH$_3$ | |
| 10.204 | 2 | CN | C$_6$H$_4$-4-OCH$_3$ | |
| 10.205 | 2 | CN | C$_6$H$_4$-4-Cl | |
| 10.206 | 2 | CN | C$_6$H$_4$-4-NO$_2$ | |
| 10.207 | 2 | CN | CH$_2$CH=CH$_2$ | |
| 10.208 | 2 | CN | CH$_2$C≡CH | |
| 10.209 | 2 | CN | CH$_2$CH=CHC$_6$H$_5$ | |
| 10.210 | 2 | CN | CH$_2$C≡CC$_6$H$_5$ | |
| 10.211 | 0 | CN | CH$_2$SCH$_3$ | |
| 10.212 | 0 | CN | CH$_2$SC$_2$H$_5$ | |
| 10.213 | 0 | CN | CH$_2$S-n-C$_3$H$_7$ | |
| 10.214 | 0 | CN | CH$_2$S-i-C$_3$H$_7$ | |
| 10.215 | 0 | CN | CH$_2$S-n-C$_4$H$_9$ | |
| 10.216 | 0 | CN | CH$_2$S-t-C$_4$H$_9$ | |
| 10.217 | 0 | CN | CH$_2$S-cyclo-C$_3$H$_5$ | |
| 10.218 | 0 | CN | CH$_2$SCH$_2$C$_6$H$_5$ | |
| 10.219 | 0 | CN | CH$_2$SCH$_2$C$_6$H$_4$-4-CH$_3$ | |
| 10.220 | 0 | CN | CH$_2$SCH$_2$C$_6$H$_4$-4-OCH$_3$ | |
| 10.221 | 0 | CN | CH$_2$SCH$_2$C$_6$H$_4$-4-Cl | |
| 10.222 | 0 | CN | CH$_2$SCH$_2$C$_6$H$_4$-4-NO$_2$ | |
| 10.223 | 0 | CN | CH$_2$SCH$_2$-2-furyl | |
| 10.224 | 0 | CN | CH$_2$SCH$_2$-2-thienyl | |
| 10.225 | 0 | CN | CH$_2$SC$_6$H$_5$ | |
| 10.226 | 0 | CN | CH$_2$SC$_6$H$_4$-4-CH$_3$ | |
| 10.227 | 0 | CN | CH$_2$SC$_6$H$_4$-4-OCH$_3$ | |
| 10.228 | 0 | CN | CH$_2$SC$_6$H$_4$-4-Cl | |
| 10.229 | 0 | CN | CH$_2$SC$_6$H$_4$-4-NO$_2$ | |
| 10.230 | 0 | CN | CH$_2$SCH$_2$CH=CH$_2$ | |
| 10.231 | 0 | CN | CH$_2$SCH$_2$C≡CH | |
| 10.232 | 0 | CN | CH$_2$SCH$_2$CH=CHC$_6$H$_5$ | |
| 10.233 | 0 | CN | CH$_2$SCH$_2$C≡CC$_6$H$_5$ | |
| 10.234 | 0 | CN | | |

TABLE 11

| Compound No. | Structural formula | Physical data |
|---|---|---|
| 11.1 | | 132–135° |
| 11.2 | | 92–93° |
| 11.3 | | |
| 11.4 | | |
| 11.5 | | |
| 11.6 | | |
| 11.7 | | |
| 11.8 | | |
| 11.9 | | |
| 11.10 | | |
| 11.11 | | |
| 11.12 | | |
| 11.13 | | |
| 11.14 | | |

TABLE 12

| Compound No. | X | Y | Z | Physical data |
|---|---|---|---|---|
| 12.1 | N | NO$_2$ | NH | |
| 12.2 | N | CN | NH | |
| 12.3 | CH | NO$_2$ | NH | |
| 12.4 | N | NO$_2$ | N-CH$_3$ | |
| 12.5 | N | CN | N-CH$_3$ | |
| 12.6 | CH | NO$_2$ | N-CH$_3$ | |
| 12.7 | N | NO$_2$ | CH$_2$ | |
| 12.8 | N | CN | CH$_2$ | |
| 12.9 | CH | NO$_2$ | CH$_2$ | |

TABLE 12-continued

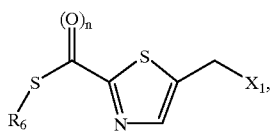

| Compound No. | X | Y | Z | Physical data |
|---|---|---|---|---|
| 12.10 | N | NO$_2$ | S | |
| 12.11 | N | CN | S | |
| 12.12 | CH | NO$_2$ | S | |

TABLE 13

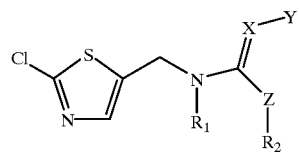

| Compound No. | X | Y | Z | R$_1$ | R$_2$ | Physical data |
|---|---|---|---|---|---|---|
| 13.1 | N | NO$_2$ | N-CH$_3$ | CH$_3$ | H | |
| 13.2 | N | CN | N-CH$_3$ | CH$_3$ | H | |
| 13.3 | CH | NO$_2$ | N-CH$_3$ | CH$_3$ | H | |
| 13.4 | N | NO$_2$ | N-CH$_3$ | C$_2$H$_5$ | H | |
| 13.5 | N | CN | N-CH$_3$ | C$_2$H$_5$ | H | |
| 13.6 | CH | NO$_2$ | N-CH$_3$ | C$_2$H$_5$ | H | |
| 13.7 | N | NO$_2$ | N-CH$_3$ | H | H | |
| 13.8 | N | CN | N-CH$_3$ | H | H | |
| 13.9 | CH | NO$_2$ | N-CH$_3$ | H | H | |
| 13.10 | N | NO$_2$ | N-CH$_3$ | CH$_3$ | CH$_3$ | |
| 13.11 | N | CN | N-CH$_3$ | CH$_3$ | CH$_3$ | |
| 13.12 | CH | NO$_2$ | N-CH$_3$ | CH$_3$ | CH$_3$ | |
| 13.13 | N | NO$_2$ | N-CH$_3$ | C$_2$H$_5$ | CH$_3$ | |
| 13.14 | N | CN | N-CH$_3$ | C$_2$H$_5$ | CH$_3$ | |
| 13.15 | CH | NO$_2$ | N-CH$_3$ | C$_2$H$_5$ | CH$_3$ | |
| 13.16 | N | NO$_2$ | N-CH$_3$ | H | CH$_3$ | |
| 13.17 | N | CN | N-CH$_3$ | H | CH$_3$ | |
| 13.18 | CH | NO$_2$ | N-CH$_3$ | H | CH$_3$ | |
| 13.19 | N | NO$_2$ | CH$_2$ | CH$_3$ | H | |
| 13.20 | N | CN | CH$_2$ | CH$_3$ | H | |
| 13.21 | CH | NO$_2$ | CH$_2$ | CH$_3$ | H | |
| 13.22 | N | NO$_2$ | CH$_2$ | C$_2$H$_5$ | H | |
| 13.23 | N | CN | CH$_2$ | C$_2$H$_5$ | H | |
| 13.24 | CH | NO$_2$ | CH$_2$ | C$_2$H$_5$ | H | |
| 13.25 | N | NO$_2$ | CH$_2$ | H | H | |
| 13.26 | N | CN | CH$_2$ | H | H | |
| 13.27 | CH | NO$_2$ | CH$_2$ | H | H | |

What is claimed is:
1. A compound of the formula IV

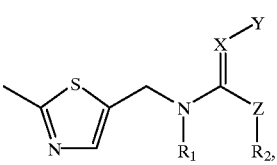

(IV)

in free form or in the form of a salt,
in which
n is 0, 1 or 2,
X$_1$ is a leaving group,
R$_4$ is an unsubstituted or substituted aryl or heteroaryl group,
R$_6$ is unsubstituted or R$_8$-substituted alkyl, unsubstituted or R$_8$-substituted alkenyl, unsubstituted or R$_8$-substituted alkynyl, cycloalkyl, unsubstituted or substituted aryl, heteroaryl, SR$_7$, (alkylene)SH or (alkylene)SR$_7$,
R$_7$ is unsubstituted or R$_4$-substituted alkyl, unsubstituted or R$_4$-substituted alkenyl, unsubstituted or R$_4$-substituted alkynyl, cycloalkyl, unsubstituted or substituted aryl, heteroaryl or a group of the formula (III)

in which
X is CH or N,
Y is NO$_2$ or CN,
Z is CHR$_3$, O, NR$_3$ or S,
R$_1$ and R$_2$ are either each, independently of the other, hydrogen, or unsubstituted or R$_4$-substituted alkyl or together a two- or three-membered alkylene bridge or a two- or three-membered alkylene bridge in which one member is replaced by a hetero member selected from the group consisting of NR$_5$, O and S, and
R$_5$ is H or alkyl, and
R$_8$ is an unsubstituted or substituted aryl or heteroaryl group, —COOH, COOM, wherein M is an alkali metal, or —COO-C$_1$–C$_8$-alkyl.

* * * * *